US012636257B2

(12) United States Patent
Pai et al.

(10) Patent No.: US 12,636,257 B2
(45) Date of Patent: May 26, 2026

(54) POLYPEPTIDE FORMULATIONS COMPRISING CRYSTAL OR AMORPHOUS POLYPEPTIDES AND VITAMIN E

(71) Applicant: Bhami's Research Laboratory, Pvt. Ltd., Karnataka (IN)

(72) Inventors: Suryakanth Motilal Pai, Karnataka (IN); Bhami Shenoy, Karnataka (IN)

(73) Assignee: Bhami's Research Laboratory, Pvt. Ltd., Mangalore (IN)

( * ) Notice: Subject to any disclaimer, the term of this patent is extended or adjusted under 35 U.S.C. 154(b) by 0 days.

(21) Appl. No.: 17/383,324

(22) Filed: Jul. 22, 2021

(65) Prior Publication Data

US 2022/0339114 A1 Oct. 27, 2022

(30) Foreign Application Priority Data

Apr. 17, 2021 (IN) .............................. 202141017881

(51) Int. Cl.

| | |
|---|---|
| *A61K 9/50* | (2006.01) |
| *A61K 9/19* | (2006.01) |
| *A61K 38/26* | (2006.01) |
| *A61K 45/06* | (2006.01) |
| *A61K 47/55* | (2017.01) |
| *C07K 16/30* | (2006.01) |
| *C07K 16/32* | (2006.01) |
| *A61K 39/00* | (2006.01) |

(52) U.S. Cl.
CPC .................. *A61K 9/50* (2013.01); *A61K 9/19* (2013.01); *A61K 38/26* (2013.01); *A61K 45/06* (2013.01); *A61K 47/551* (2017.08); *C07K 16/3015* (2013.01); *C07K 16/32* (2013.01); *A61K 2039/505* (2013.01)

(58) Field of Classification Search
CPC . A61K 9/50; A61K 9/19; A61K 38/26; A61K 45/06; A61K 47/551; A61K 2039/505; A61K 9/10; A61K 39/39591; A61K 9/4858; A61K 9/0053; A61K 9/0095; A61K 47/22; A61K 38/00; C07K 16/3015; C07K 16/32; C07K 2317/24; C07K 2317/90

See application file for complete search history.

(56) References Cited

U.S. PATENT DOCUMENTS

| | | | |
|---|---|---|---|
| 10,213,490 B2 | 2/2019 | Bromley et al. | |
| 10,646,569 B2 | 5/2020 | Shenoy | |
| 2013/0224300 A1* | 8/2013 | Maggio .................. | A61K 47/14 |
| | | | 514/777 |
| 2016/0206703 A1* | 7/2016 | Kidron ................... | A61K 9/485 |

FOREIGN PATENT DOCUMENTS

| | | | | |
|---|---|---|---|---|
| WO | WO-2012034360 A1 * | 3/2012 | ............. | A61K 38/28 |
| WO | WO-2019/226969 A1 | 11/2019 | | |
| WO | WO-2022/219646 A1 | 10/2022 | | |

OTHER PUBLICATIONS

International Search Report for PCT/IN22/50355, 3 pages (mailed Jul. 19, 2022).
Written Opinion for PCT/IN22/50355, 5 pages (mailed Jul. 19, 2022).
Zhang, An update on oral drug delivery via intestinal lymphatic transport, Acta Pharmaceutica Sinica B., 11(8):2449-2468 (2021).
Chiu, Y-Y. et al., Human Jejunal Permeability of Cyclosporin A: Influence of Surfactants on P-Glycoprotein Efflux in Caco-2 Cells, 20(5):749-756 (2003).
Lai, S. K. et al., Rapid transport of large polymeric nanoparticles in fresh undiluted human mucus, PNAS, 104(5):1482-1487 (2007).
Reboul, E. et al., Respective contributions of intestinal Niemann-Pickl C1-like 1 and scavenger receptor class B type I to cholesterol and tocopherol uptake: in vivo v. in vitro studies, Brit. Jrnl. Nutri., 107:1296-1304 (2012).
Wang, X. and Quinn, P. J., The location and function of vitamin E in membranes (Review), Mol. Membrane Biol., 17:143-156 (2000).
Zhang, Y. et al., A comparison of the in vitro permeation of niacinamide in mammalian skin and in the Parallel Artificial Membrane Permeation Assay (PAMPA) model, Inter. Jrnl. Pharm., 556:142-149 (2019).

* cited by examiner

*Primary Examiner* — Sudhakar Katakam
(74) *Attorney, Agent, or Firm* — Choate, Hall & Stewart LLP; Beejan Asady; Brenda Herschbach Jarrell

(57) ABSTRACT

The present disclosure provides, among other things, methods and compositions for the oral administration of polypeptides. Many polypeptides are typically administered in liquid solutions by intravenous or subcutaneous injection. The present disclosure provides methods and compositions that include a polypeptide formulation for oral delivery that includes a core and a pharmaceutically acceptable capsule, where the core includes an amorphous polypeptide composition or a crystallized polypeptide composition and a pharmaceutically acceptable carrier comprising a vitamin E agent.

18 Claims, 26 Drawing Sheets

Microparticles of Trastuzumab – Before and After Drying

POLYPEPTIDE FORMULATIONS COMPRISING CRYSTAL OR AMORPHOUS POLYPEPTIDES AND VITAMIN E

BACKGROUND

Polypeptide therapeutics play an important role in medicine. Many current therapeutics include polypeptides such as enzymes and antibodies. A typical route of administration for polypeptide therapeutics is intravenous or subcutaneous injection. Injection of therapeutic agents is associated with well-known drawbacks. For many years, researchers have sought alternative compositions and methods for administration of polypeptide therapeutics.

SUMMARY

The present disclosure provides, among other things, methods and compositions for the administration (e.g., oral administration) of polypeptides. Many polypeptides are typically formulated as liquid solutions for administration by intravenous or subcutaneous injection. The present disclosure provides, among other things, encapsulated polypeptide formulations and suspensions for oral delivery that include an amorphous polypeptide composition or a crystallized polypeptide composition (e.g., a powder form that includes amorphous polypeptide or crystallized polypeptide) and a pharmaceutically acceptable carrier including a vitamin E agent. The present disclosure includes the surprising discovery that oral delivery of formulations disclosed herein that include a polypeptide and Vitamin E successfully deliver polypeptides to the bloodstream. Without wishing to be bound by any particular scientific theory, the present disclosure further includes the surprising discovery that polypeptides orally administered in a formulation as disclosed herein including a vitamin E agent are efficiently delivered to the bloodstream, lymphatic system, and thoracic duct. In various embodiments, polypeptides orally administered in a formulation as disclosed herein including a vitamin E agent are efficiently delivered to the bloodstream via the lymphatic system, e.g., at least in part via the thoracic duct. The present disclosure includes the realization that formulations provided herein that include polypeptide and vitamin E provide platform are of broad utility with a generalized ability to delivery polypeptides to the bloodstream. Accordingly, those of skill in the art will appreciate from the present disclosure, including the present Examples, that formulations provided herein are advantageous and useful without need to specify the polypeptide included therein. Further still, the present disclosure demonstrates unexpectedly advantageous characteristics of various oral delivery of formulations disclosed herein, including improved pharmacokinetic properties such as rate of delivery into the bloodstream and/or increased half-life.

In at least one aspect, the present disclosure includes a polypeptide formulation for oral delivery including (i) a crystallized polypeptide composition or an amorphous polypeptide composition and (ii) a pharmaceutically acceptable carrier including a vitamin E agent, optionally where (i) the polypeptide formulation is an encapsulated polypeptide formulation including a core and a pharmaceutically acceptable capsule, where the core includes the crystallized polypeptide composition or amorphous polypeptide composition and the pharmaceutically acceptable carrier or (ii) the polypeptide formulation is a suspension formulation.

In at least one aspect, the present disclosure includes a method of delivering a polypeptide to the bloodstream of a subject, the method including orally administering to the subject a polypeptide formulation including (i) a crystallized polypeptide composition or an amorphous polypeptide composition and (ii) a pharmaceutically acceptable carrier including a vitamin E agent, optionally where (i) the polypeptide formulation is an encapsulated polypeptide formulation including a core and a pharmaceutically acceptable capsule, where the core includes the crystallized polypeptide composition or amorphous polypeptide composition and the pharmaceutically acceptable carrier or (ii) the polypeptide formulation is a suspension formulation. In certain embodiments, the polypeptide is delivered to the bloodstream via the lymphatic system, optionally where the polypeptide is delivered to the blood stream via the thoracic duct.

In at least one aspect, the present disclosure includes a method of delivering a polypeptide to the thoracic duct or lymph of a subject, the method including orally administering to the subject a polypeptide formulation including (i) a crystallized polypeptide composition or an amorphous polypeptide composition and (ii) a pharmaceutically acceptable carrier including a vitamin E agent, optionally where (i) the polypeptide formulation is an encapsulated polypeptide formulation including a core and a pharmaceutically acceptable capsule, where the core includes the crystallized polypeptide composition or amorphous polypeptide composition and the pharmaceutically acceptable carrier or (ii) the polypeptide formulation is a suspension formulation.

In at least one aspect, the present disclosure includes a method of producing an encapsulated polypeptide formulation for oral delivery, the method including encapsulating within a capsule a core including (i) an amorphous polypeptide composition or a crystallized polypeptide composition and (ii) a pharmaceutically acceptable carrier including a vitamin E agent. In at least one aspect, the present disclosure includes a method of producing a polypeptide suspension for oral delivery, the method including suspending (i) a crystallized polypeptide composition or an amorphous polypeptide composition in (ii) a pharmaceutically acceptable carrier including a vitamin E agent.

In certain embodiments, the polypeptide includes: (i) a therapeutic polypeptide; (ii) an antibody agent or fragment thereof; (iii) a monoclonal antibody or fragment thereof; (iv) a fusion polypeptide; (v) an immunoglobulin; (vi) an enzyme; or (vii) an analog and/or modified form of any of (i)-(vi), optionally where the polypeptide is modified by one or more of pegylation, acetylation, amidation, lipidation, methylation, phosphorylation, glycosylation, glycation, sulfation, mannosylation, nitrosylation, acylation, palmitoylation, prenylation, fatty acids, or a combinations thereof. In certain embodiments, the polypeptide is selected from an antibody (e.g., an anti-HER2 antibody, e.g., trastuzumab), a GLP-1 receptor agonist, human glucagon-like peptide-1 (GLP-1) or an analog thereof (e.g., a synthetic analog, e.g., liraglutide), parathyroid hormone (e.g., recombinant human parathyroid hormone analog, e.g., teriparatide), insulin (e.g., Humulin®), rituximab, bevacizumab, cetuximab, etanercept, infliximab, agalsidase beta, agalsidase alfa, imiglucerase, aliglucerase alfa, velaglucerase alfa, alglucerase, sebelipase alpha, laronidase, idursulfase, elosulfase alpha, galsulfase, pancrelipase, sapropterin, eliglustat, galsulfase, asfotase alfa, pegvaliase, elapegademase, sacrosidase, Factor I, Factor II, Factor III, Factor IV, Factor V, Factor VI, Factor VII, Factor VIII, Factor IX, Factor X, Factor XI, Factor XII, Factor XIII, von Willebrand factor, etanercept, aflibercept, rilonacept, alefacept, romiplostim, abatacept/belatacept, and/or denileukin-diftitox, or an analog or derivative thereof, optionally where the polypeptide is natural, synthetic, or engineered. In certain embodiments, the polypeptide has a molecular weight between about 50 Da and 25 kDa, optionally where the molecular weight is between about 50 Da and about 1 kDa, about 50 Da and about 2 kDa, about 50 Da and about 3 kDa, about 50 Da and about 4 kDa, about 50 Da and about 5 kDa, about 50 Da and about 10 kDa, about 50 Da and about 15 kDa, or about 50 Da and about 20 kDa. In certain embodiments, the polypeptide has a molecular weight between about 25 kDa and about 1,000 kDa, optionally where the molecular weight is between about 25 kDa and about 500 kDa, about 100 kDa and about 500 kDa, about 120 kDa and about 250 kDa, or about 150 kDa and about 300 kDa. In certain embodiments, the polypeptide formulation includes about 1 µg to about 2,000 mg of the polypeptide, optionally where the polypeptide formulation includes about 1 µg to about 1,000 mg, about 1 µg to about 500 mg, about 1 µg to about 400 mg, about 1 µg to about 300 mg, about 1 µg to about 200 mg, about 1 µg to about 100 mg, about 1 µg to about 50 mg, about 1 µg to about 25 mg, about 1 µg to about 20 mg, about 1 µg to about 15 mg, about 1 µg to about 10 mg, about 1 µg to about 5 mg, about 1 µg to about 1 mg, about 1 µg to about 500 µg, about 1 µg to about 250 µg, about 1 µg to about 200 µg, about 1 µg to about 150 µg, about 1 µg to about 100 µg, about 1 µg to about 50 µg, about 1 mg to about 1,000 mg, about 1 mg to about 500 mg, about 1 mg to about 400 mg, about 1 mg to about 300 mg, about 1 mg to about 200 mg, about 1 mg to about 100 mg, about 1 mg, to about 50 mg, about 1 mg to about 25 mg of the polypeptide.

In certain embodiments, the polypeptide formulation includes about 1 mg to about 2,000 mg of a vitamin E agent, optionally where the polypeptide formulation includes about 1 mg to about 1,000 mg, about 1 mg to about 500 mg, about 1 mg to about 400 mg, about 1 mg to about 300 mg, about 1 mg to about 200 mg, about 1 mg to about 100 mg, about 1 mg to about 50 mg, or about 1 mg to about 25 mg of a vitamin E agent. In certain embodiments, the polypeptide formulation includes a molar excess or excess by weight of a vitamin E agent relative to the amount of polypeptide in the polypeptide formulation, optionally where in the excess is a fold excess of at least 1.1, 1.5, 2, 3, 4, 5, 6, 7, 8, 9, 10, 20, 30, 40, 50, 60, 70, 80, 90, 100, 500, or 1,000 fold.

In certain embodiments, the crystallized polypeptide composition includes crystals of polypeptide having an average particle size of less than 25 microns, e.g., less than 20, 15, 10, 5, 4, 3, 2, 1, or 0.5 microns, optionally where the crystals of polypeptide have an average particle size that is between 0.5 microns and 1, 2, 3, 4, 5, 10, 15, 20, or 25 microns or where the crystals of polypeptide have an average particle size that is between 1 micron and 1, 2, 3, 4, 5, 10, 15, 20, or 25 microns. In certain embodiments, the amorphous polypeptide composition includes particles of polypeptide having an average particle size of less than 25 microns, e.g., less than 20, 15, 10, 5, 4, 3, 2, 1, or 0.5 microns, optionally where the particles of polypeptide have an average particle size that is between 0.5 microns and 1, 2, 3, 4, 5, 10, 15, 20, or 25 microns or where the particles of polypeptide have an average particle size that is between 1 micron and 1, 2, 3, 4, 5, 10, 15, 20, or 25 microns.

In certain embodiments, the polypeptide composition includes lyophilized polypeptide. In certain embodiments, the polypeptide composition includes microcrystals of polypeptide. In certain embodiments, the polypeptide composition includes a powder including crystallized polypeptide.

In certain embodiments, the core is a viscous solution. In certain embodiments, the capsule is a hard-shell capsule or soft-shell capsule, optionally where the capsule is a gelatin capsule or HPMC capsule. In certain embodiments, the capsule is formulated for delivery to the gut, optionally where the capsule is formulated for delivery to stomach and/or intestine. In certain embodiments, the capsule includes an enteric coating.

In certain embodiments, the core further includes one or more excipients or additives selected from the group consisting of aggregation-reducing agents, sugars or sugar alcohols, polysaccharides, stabilizers, hyaluronidase, buffering agents, preservatives, carriers, antioxidants, chelating agents, natural or synthetic polymers, cryoprotectants, lyoprotectants, surfactants, bulking agents, acidifying agents, ingredients to reduce injection site discomfort, antifoaming agents, alkalizing agents, vehicles, aggregation inhibitors, solubilizing agents, tonicity modifiers, and stabilizing agents and combinations thereof. In certain embodiments, the one or more excipients or additives are individually or cumulatively present at a concentration between 0.1 mM and about 1,000 mM, between about 0.1 mM and about 500 mM, between about 0.1 mM and about 200 mM. or between about 0.1 mM and about 100 mM. In certain embodiments, (i) the aggregation-reducing agent(s)s are selected from the group consisting of nicotinic acid, caffeine citrate, caffeine nicotinate, caffeine, octyl-β-D-glucopyranoside, and n-dodecyl-β-D-maltoside and optionally in combination with one or more of arginine, tryptophan, histidine, proline, cysteine, methionine, β-alanine, Potassium Glutamate, Arginine Ethylester, lysine, aspartic acid, glutamic acid, glycine, DTPA (diethylenetriaminepentaacetic acid), EGTA(aminopolycarboxylic acid), EDTA (Ethylenediaminetetraacetic acid), hydroxy propyl beta (HP-Beta) cyclodextrins, hydroxy propyl gamma (HP-Gamma) cyclodextrins, sulfo-butyl ether (SBE) cyclodextrins, TMAO (trimethylamine N-oxide), trehalose, ethylene glycol, betaine, xylitol, sorbitol, 6-(N-(7-nitrobenz-2-oxa-1,3-diazol-4-yl)amino)hexanoic acid (NBD-X), methyl acetyl phosphate (MAP), citraconic anhydride, pyrophosphate, citrate, and combinations thereof; (ii) the tonicity modifier(s) are selected from the group consisting of arginine, cysteine, histidine, glycine, sodium chloride, potassium chloride, sodium citrate, saccharides such as sucrose, glucose, dextrose, glycerin or mannitol, and combinations thereof; (iii) the antioxidant(s) are selected from the group consisting of glycine, lysine, EDTA, DTPA, sorbitol, mannitol, ascorbic acid, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, sodium thiosulfate, sulfur dioxide, tocopherol, and combinations thereof; or (iv) the lyoprotectant(s) are selected from the group consisting of sucrose, lactose, trehalose, dextran, erythritol, arabitol, xylitol, sorbitol, maltose, lactulose, maltulose, glucitol, maltitol, lactitol, isomaltulose and mannitol; amino acids, such as arginine or histidine or proline or glycine; lyotropic salts, such as magnesium sulfate; propylene glycol, glycerol, poly(ethylene glycol), or poly(propylene glycol); gelatin, dextrins, modified starch, carboxymethyl cellulose, and combinations thereof.

Definitions

A, An, The: As used herein, "a", "an", and "the" refer to one or more than one (i.e., to at least one) of the grammatical object of the article. By way of example, "an element" discloses embodiments of exactly one element and embodiments including more than one element.

About: As used herein, term "about", when used in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referenced value.

Administration: As used herein, the term "administration" typically refers to administration of a composition to a subject or system to achieve delivery of an agent that is, or is included in, the composition.

Agent: As used herein, the term "agent" may refer to any chemical entity, including without limitation any of one or more of an atom, molecule, compound, amino acid, polypeptide, nucleotide, nucleic acid, polypeptide complex, liquid, solution, saccharide, polysaccharide, lipid, or combination or complex thereof.

Amino acid: In its broadest sense, as used herein, refers to any compound and/or substance that can be incorporated into a polypeptide chain, e.g., through formation of one or more peptide bonds. In some embodiments, an amino acid has the general structure $H_2N$—C(H)(R)—COOH. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with a typical or canonical amino acid structure. For example, in some embodiments, an amino acid can be modified by methylation, amidation, acetylation, pegylation, glycosylation, phosphorylation, and/or substitution (e.g., of the amino group, the carboxylic acid group, one or more protons, and/or the hydroxyl group) as compared with the general structure. In some embodiments, such modification can, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" can be used to refer to a free amino acid; in some embodiments it can be used to refer to an amino acid residue of a polypeptide.

Amorphous: As used herein, the term "amorphous" generally refers to a non-crystalline solid form of polypeptide, sometimes referred to as an amorphous solid" or "amorphous precipitate", which typically has no, or essentially no, molecular lattice structure characteristic of the crystalline solid state.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Antibody: As used herein, the term "antibody" refers to a polypeptide that includes one or more canonical immunoglobulin sequence elements sufficient to confer specific binding to a particular antigen (e.g., a heavy chain variable domain, a light chain variable domain, and/or one or more CDRs). Thus, the term antibody includes, without limitation, human antibodies, non-human antibodies, synthetic and/or engineered antibodies, fragments thereof, and agents including the same. Antibodies can be naturally occurring immunoglobulins (e.g., generated by an organism reacting to an antigen). Synthetic, non-naturally occurring, or engineered antibodies can be produced by recombinant engineering, chemical synthesis, or other artificial systems or methodologies known to those of skill in the art.

As is well known in the art, typical human immunoglobulins are approximately 150 kD tetrameric agents that include two identical heavy (H) chain polypeptides (about 50 kD each) and two identical light (L) chain polypeptides (about 25 kD each) that associate with each other to form a structure commonly referred to as a "Y-shaped" structure. Typically, each heavy chain includes a heavy chain variable domain (VH) and a heavy chain constant domain (CH). The heavy chain constant domain includes three CH domains: CH1, CH2 and CH3. A short region, known as the "switch", connects the heavy chain variable and constant regions. The "hinge" connects CH2 and CH3 domains to the rest of the immunoglobulin. Each light chain includes a light chain variable domain (VL) and a light chain constant domain (CL), separated from one another by another "switch." Each variable domain contains three hypervariable loops known as "complement determining regions" (CDR1, CDR2, and CDR3) and four somewhat invariant "framework" regions (FR1, FR2, FR3, and FR4). In each VH and VL, the three CDRs and four FRs are arranged from amino-terminus to carboxy-terminus in the following order: FR1, CDR1, FR2, CDR2, FR3, CDR3, and FR4. The variable regions of a heavy and/or a light chain are typically understood to provide a binding moiety that can interact with an antigen. Constant domains can mediate binding of an antibody to various immune system cells (e.g., effector cells and/or cells that mediate cytotoxicity), receptors, and elements of the complement system. Heavy and light chains are linked to one another by a single disulfide bond, and two other disulfide bonds connect the heavy chain hinge regions to one another, so that the dimers are connected to one another and the tetramer is formed. When natural immunoglobulins fold, the FR regions form the beta sheets that provide the structural framework for the domains, and the CDR loop regions from both the heavy and light chains are brought together in three-dimensional space so that they create a single hypervariable antigen binding site located at the tip of the Y structure.

In some embodiments, an antibody is polyclonal, monoclonal, monospecific, or multispecific antibodies (including bispecific antibodies). In some embodiments, an antibody includes at least one light chain monomer or dimer, at least one heavy chain monomer or dimer, at least one heavy chain-light chain dimer, or a tetramer that includes two heavy chain monomers and two light chain monomers. Moreover, the term "antibody" can include (unless otherwise stated or clear from context) any art-known constructs or formats utilizing antibody structural and/or functional features including without limitation intrabodies, domain antibodies, antibody mimetics, Zybodies®, Fab fragments, Fab' fragments, F(ab')2 fragments, Fd' fragments, Fd fragments, isolated CDRs or sets thereof, single chain antibodies, single-chain Fvs (scFvs), disulfide-linked Fvs (sdFv), polypeptide-Fc fusions, single domain antibodies (e.g., shark single domain antibodies such as IgNAR or fragments thereof), cameloid antibodies, camelized antibodies, masked antibodies (e.g., Probodies®), affybodies, anti-idiotypic (anti-Id) antibodies (including, e.g., anti-anti-Id antibodies), Small Modular ImmunoPharmaceuticals ("SMIPsTM"), single chain or Tandem diabodies (TandAb®), VHHs, Anticalins®, Nanobodies® minibodies, BiTE®s, ankyrin repeat proteins or DARPINs®, Avimers®, DARTs, TCR-like antibodies, Adnectins®, Affilins®, Trans-Bodies®, Affibodies®, TrimerX®, MicroProteins, Fynomers®, Centyrins®, and KALBITOR®s, CARs, engineered TCRs, and antigen-binding fragments of any of the above.

In various embodiments, an antibody includes one or more structural elements recognized by those skilled in the art as a complementarity determining region (CDR) or variable domain. In some embodiments, an antibody can be a covalently modified ("conjugated") antibody (e.g., an antibody that includes a polypeptide including one or more canonical immunoglobulin sequence elements sufficient to confer specific binding to a particular antigen, where the polypeptide is covalently linked with one or more of a therapeutic agent, a detectable moiety, another polypeptide, a glycan, or a polyethylene glycol molecule). In some embodiments, antibody sequence elements are humanized, primatized, chimeric, etc, as is known in the art.

An antibody including a heavy chain constant domain can be, without limitation, an antibody of any known class, including but not limited to, IgA, secretory IgA, IgG, IgE and IgM, based on heavy chain constant domain amino acid sequence (e.g., alpha ($\alpha$), delta ($\delta$), epsilon ($\varepsilon$), gamma ($\gamma$) and mu ($\mu$). IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes. As used herein, a "light chain" can be of a distinct type, e.g., kappa ($\kappa$) or lambda ($\lambda$), based on the amino acid sequence of the light chain constant domain. In some embodiments, an antibody has constant region sequences that are characteristic of mouse, rabbit, primate, or human immunoglobulins. Naturally-produced immunoglobulins are glycosylated, typically on the CH2 domain. As is known in the art, affinity and/or other binding attributes of Fc regions for Fc receptors can be modulated through glycosylation or other modification. In some embodiments, an antibody may lack a covalent modification (e.g., attachment of a glycan) that it would have if produced naturally. In some embodiments, antibodies produced and/or utilized in accordance with the present invention include glycosylated Fc domains, including Fc domains with modified or engineered such glycosylation.

Antibody fragment: As used herein, an "antibody fragment" refers to a portion of an antibody or antibody agent as described herein, and typically refers to a portion that includes an antigen-binding portion or variable region thereof. An antibody fragment can be produced by any means. For example, in some embodiments, an antibody fragment can be enzymatically or chemically produced by fragmentation of an intact antibody or antibody agent. Alternatively, in some embodiments, an antibody fragment can be recombinantly produced (i.e., by expression of an engineered nucleic acid sequence. In some embodiments, an antibody fragment can be wholly or partially synthetically produced. In some embodiments, an antibody fragment (particularly an antigen-binding antibody fragment) can have a length of at least about 50, 60, 70, 80, 90, 100, 110, 120, 130, 140, 150, 160, 170, 180, 190 amino acids or more, in some embodiments at least about 200 amino acids.

Associated with: Two events or entities are "associated" with one another, as that term is used herein, if the presence, level and/or form of one is correlated with that of the other. For example, a particular entity (e.g., polypeptide, genetic signature, metabolite, microbe, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, or a combination thereof.

Between or From: As used herein, the term "between" refers to content that falls between indicated upper and lower, or first and second, boundaries (or "bounds"), inclusive of the boundaries. Similarly, the term "from", when used in the context of a range of values, indicates that the range includes content that falls between indicated upper and lower, or first and second, boundaries, inclusive of the boundaries.

Bioavailability: As used herein, the term "bioavailability" can refer to the degree to which a substance, e.g., a polypeptide such as an antibody or antibody fragment, administered to an in vivo subject, becomes available to a tissue to which the substance is targeted (e.g., the bloodstream and/or plasma). Bioavailability can refer to the degree to which a substance that has been administered to an in vivo subject is delivered to blood of the subject. Bioavailability can refer to the ability of a substance to perform a function in the subject. Bioavailability can be measured in a number of ways, e.g., as the concentration of a substance in the bloodstream or plasma. In some embodiments, bioavailability can be assessed, for example, by comparing the "area under the curve" (AUC) in a plot of the plasma concentration as a function of time (area under the plasma concentration curve from time zero to a time where the plasma concentration returns to baseline levels). AUC can be calculated, for example, using the linear trapezoidal rule. "AUC0-t" refers to the area under the plasma concentration curve from time zero to a time, t, later, for example to the time of reaching baseline.

Cancer: As used herein, the term "cancer" refers to a disease, disorder, or condition in which cells exhibit relatively abnormal, uncontrolled, and/or autonomous growth, so that they display an abnormally elevated proliferation rate and/or aberrant growth phenotype characterized by a significant loss of control of cell proliferation. In some embodiments, a cancer can include one or more tumors. In some embodiments, a cancer can be or include cells that are precancerous (e.g., benign), malignant, pre-metastatic, metastatic, and/or non-metastatic. In some embodiments, a cancer can be or include a solid tumor. In some embodiments, a cancer can be or include a hematologic tumor.

Engineered: As used herein, the term "engineered" refers to the aspect of having been manipulated by the hand of man. For example, a polynucleotide is considered to be "engineered" when two or more sequences, that are not linked together in that order in nature, are manipulated by the hand of man to be linked to one another in the engineered polynucleotide. Those of skill in the art will appreciate that an "engineered" nucleic acid or amino acid sequence can be a recombinant nucleic acid or amino acid sequence. In some embodiments, an engineered polynucleotide includes a coding sequence and/or a regulatory sequence that is found in nature operably linked with a first sequence but is not found in nature operably linked with a second sequence, which is in the engineered polynucleotide and operably linked in with the second sequence by the hand of man. In some embodiments, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution, deletion, or mating). As is common practice and is understood by those of skill in the art, progeny or copies, perfect or imperfect, of an engineered polynucleotide or cell are typically still referred to as "engineered" even though the direct manipulation was of a prior entity.

Excipient: As used herein, "excipient" refers to a non-therapeutic agent that may be included in a pharmaceutical composition, for example to provide or contribute to a desired consistency or stabilizing effect. In some embodiments, suitable pharmaceutical excipients may include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, or the like.

"Improve," "increase," "inhibit," or "reduce": As used herein, the terms "improve", "increase", "inhibit", and "reduce", and grammatical equivalents thereof, indicate qualitative or quantitative difference from a reference.

Pharmaceutically acceptable: As used herein, the term "pharmaceutically acceptable," as applied to one or more, or all, component(s) for formulation of a composition as disclosed herein, means that each component must be compatible with the other ingredients of the composition and not deleterious to the recipient thereof.

Pharmaceutical composition or formulation: As used herein, the term "pharmaceutical composition" or "formulation" refers to a composition in which a therapeutic agent is formulated together with one or more pharmaceutically acceptable carriers.

Polypeptide: As used herein, "polypeptide" refers to any polymeric chain of two or more amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may be or include of natural amino acids, non-natural amino acids, or both. In some embodiments, a polypeptide may be or include only natural amino acids or only non-natural amino acids. In some embodiments, a polypeptide can include D-amino acids, L-amino acids, or both. In some embodiments, a polypeptide may include only L-amino acids. In some embodiments, a polypeptide may include one or more pendant groups or other modifications, e.g., one or more amino acid side chains, e.g., at the polypeptide's N-terminus, at the polypeptide's C-terminus, at non-terminal amino acids, or at any combination thereof. In some embodiments, such pendant groups or modifications may be selected from acetylation, amidation, lipidation, methylation, phosphorylation, glycosylation, glycation, sulfation, mannosylation, nitrosylation, acylation, palmitoylation, prenylation, pegylation, etc., including combinations thereof. In some embodiments, a polypeptide may be cyclic, and/or may include a cyclic portion.

In some embodiments, the term "polypeptide" may be appended to a name of a reference polypeptide, activity, or structure to indicate a class of polypeptides that share a relevant activity or structure. For such classes, the present specification provides and/or those skilled in the art will be aware of exemplary polypeptides within the class whose amino acid sequences and/or functions are known. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class. For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that can in some embodiments be or include a characteristic sequence element) that shows very high sequence identity, often greater than 90% or even 95%, 96%, 97%, 98%, or 99%. Such a conserved region usually encompasses at least 3-4 and in some instances up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a relevant polypeptide can be or include a fragment of a parent polypeptide. In some embodiments, a useful polypeptide may be or include a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

Reference: As used herein, "reference" refers to a standard or control relative to which a comparison is performed. For example, in some embodiments, an agent, sample, sequence, subject, animal, or individual, or population thereof, or a measure or characteristic representative thereof, is compared with a reference, an agent, sample, sequence, subject, animal, or individual, or population thereof, or a measure or characteristic representative thereof. In some embodiments, a reference is a measured value. In some embodiments, a reference is an established standard or expected value. In some embodiments, a reference is a historical reference. A reference can be quantitative of qualitative. Typically, as would be understood by those of skill in the art, a reference and the value to which it is compared represents measure under comparable conditions. Those of skill in the art will appreciate when sufficient similarities are present to justify reliance on and/or comparison. In some embodiments, an appropriate reference may be an agent, sample, sequence, subject, animal, or individual, or population thereof, under conditions those of skill in the art will recognize as comparable, e.g., for the purpose of assessing one or more particular variables (e.g., presence or absence of an agent or condition), or a measure or characteristic representative thereof.

Small molecule: As used herein, the term "small molecule" means a low molecular weight organic and/or inorganic compound. In general, a "small molecule" is a molecule that is less than about 5 kilodaltons (kD) in size. In some embodiments, a small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2,000 g/mol, less than about 1500 g/mol, less than about 1,000 g/mol, less than about 800 g/mol, or less than about 500 g/mol. In some embodiments, a small molecule is not a polymer. In some embodiments, a small molecule does not include a polymeric moiety. In some embodiments, a small molecule is not and/or does not include a polypeptide. In some embodiments, a small molecule is not and/or does not include a polynucleotide (e.g., is not an oligonucleotide). In some embodiments, a small molecule is not and/or does not include a polysaccharide; for example, in some embodiments, a small molecule is not a glycoprotein, proteoglycan, glycolipid, etc.). In some embodiments, a small molecule is not a lipid. In some embodiments, a small molecule is a modulating agent (e.g., is an inhibiting agent or an activating agent). In some embodiments, a small molecule is biologically active. In some embodiments, a small molecule is detectable (e.g., includes at least one detectable moiety). In some embodiments, a small molecule is a therapeutic agent.

Subject: As used herein, the term "subject" refers to an organism, typically a mammal (e.g., a human, rat, or mouse). In some embodiments, a subject is suffering from a disease, disorder or condition. In some embodiments, a subject is susceptible to a disease, disorder, or condition. In some embodiments, a subject displays one or more symptoms or characteristics of a disease, disorder or condition. In some embodiments, a subject is not suffering from a disease, disorder or condition. In some embodiments, a subject does not display any symptom or characteristic of a disease, disorder, or condition. In some embodiments, a subject has one or more features characteristic of susceptibility to or risk of a disease, disorder, or condition. In some embodiments, a subject is a subject that has been tested for a disease, disorder, or condition, and/or to whom therapy has been administered. In some instances, a human subject can be interchangeably referred to as a "patient" or "individual." A subject administered an agent associated with treatment of a disease, disorder, or condition with which the subject is associated can be referred to as a subject in need of the agent, i.e., as a subject in need thereof.

Therapeutic agent: As used herein, the term "therapeutic agent" refers to any agent that elicits a desired pharmacological effect when administered to a subject. In some embodiments, an agent is considered to be a therapeutic agent if it demonstrates a statistically significant effect across an appropriate population. In some embodiments, the appropriate population can be a population of model organisms or a human population. In some embodiments, an appropriate population can be defined by various criteria, such as a certain age group, gender, genetic background, preexisting clinical conditions, etc. In some embodiments, a therapeutic agent is a substance that can be used for treatment of a disease, disorder, or condition. In some embodiments, a therapeutic agent is an agent that has been or is required to be approved by a government agency before it can be marketed for administration to humans. In some embodiments, a therapeutic agent is an agent for which a medical prescription is required for administration to humans.

Therapeutically effective amount: As used herein, "therapeutically effective amount" refers to an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that a therapeutically effective amount does not necessarily achieve successful treatment in every particular treated individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

Treatment: As used herein, the term "treatment" (also "treat" or "treating") refers to administration of a therapy that partially or completely alleviates, ameliorates, relieves, inhibits, delays onset of, reduces severity of, and/or reduces incidence of one or more symptoms, features, and/or causes of a particular disease, disorder, or condition, or is administered for the purpose of achieving any such result. In some embodiments, such treatment can be of a subject who does not exhibit signs of the relevant disease, disorder, or condition and/or of a subject who exhibits only early signs of the disease, disorder, or condition. Alternatively or additionally, such treatment can be of a subject who exhibits one or more established signs of the relevant disease, disorder and/or condition. In some embodiments, treatment can be of a subject who has been diagnosed as suffering from the relevant disease, disorder, and/or condition. In some embodiments, treatment can be of a subject known to have one or more susceptibility factors that are statistically correlated with increased risk of development of the relevant disease, disorder, or condition.

DETAILED DESCRIPTION

Figure 1:
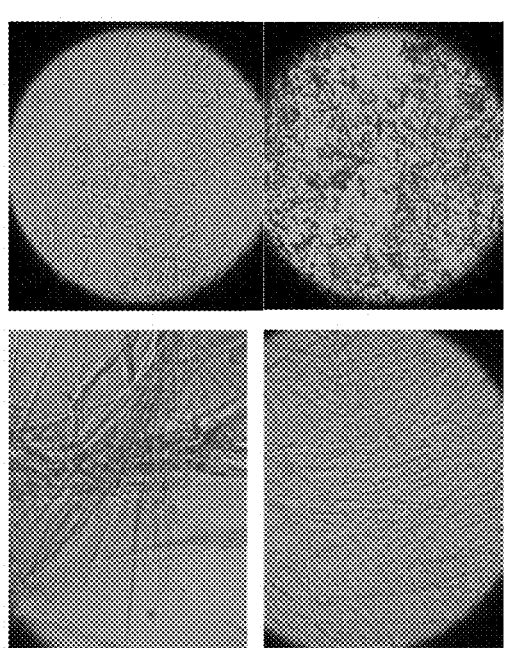
FIG. 1 is a set of four images showing microparticles of trastuzumab before drying (left panels) and after drying (right panels).

Extensive effort has been expended by the pharmaceutical industry to bring polypeptide therapeutics to market. Clinical trials have included hundreds of polypeptides for treatment of over 100 conditions. However, clinical use of polypeptides has been hampered by numerous obstacles to their successful delivery. Bioavailability, stability, and therapeutic efficacy are among the factors considered in the development of formulations for polypeptide delivery. Many polypeptides are administered by parenteral routes such as subcutaneous, intramuscular, or intravenous injection. The present disclosure includes the recognition that oral administration would generally be preferable to injection of polypeptide therapeutics, e.g., for patient acceptance, home use, and compliance with long-term regimens. These advantages among others could cause oral formulations of polypeptide products to have therapeutic and commercial value distinct from and/or greater than those of parenteral formulations.

Despite tremendous efforts to achieve oral delivery of polypeptides, parenteral delivery remains the major mode of administration for polypeptide therapeutics. While oral delivery may be standard for administration of small molecules, the difficulty of oral delivery of polypeptides is a problem recognized by those of skill in the art. Intrinsic physicochemical and biological properties, including large molecular size, poor permeation through gastrointestinal membrane, poor stability attributed to low pH of gastric fluid, and susceptibility to proteolytic enzymes are among the factors that render oral delivery of polypeptides highly challenging. In various trials, it was observed that orally administered polypeptides demonstrated bioavailability of less than 1%, while higher levels, and in some instances a target bioavailability of at least 30%-50%, can be preferred for therapeutic efficacy. Efforts to improve polypeptide stability and performance have included chemical modification of polypeptides such as PEGylation, hyperglycosylation, and mannosylation or use of colloidal carriers including microparticles, nanoparticles, liposomes, carbon nanotubes and micelles. Despite such efforts, parenteral administration of polypeptides has persisted as the norm. The present disclosure provides a solution to the long-standing difficulty of formulating polypeptides for oral administration.

Various compositions of the present disclosure can include a core within a pharmaceutically acceptable capsule. In various embodiments, the core includes an amorphous polypeptide composition or a crystallized polypeptide composition and a pharmaceutically acceptable carrier including a vitamin E agent.

Vitamin E

Vitamin E agents, as used herein, refer to compounds or entities that, when administered to a subject, deliver to that subject a vitamin E active moiety. In some embodiments, a vitamin E agent is provided and/or utilized as a salt, co-crystal, free acid or base, solvate, ester, hydrate, polymorph, or anhydrous form. In some embodiments, a vitamin E agent is provided and/or utilized in a particular stereoisomeric form, or as a mixture of stereoisomeric forms. In some embodiments, a vitamin E agent is a prodrug of vitamin E wherein vitamin E is the intended metabolite for a therapeutic effect.

Vitamin E agents (referred to herein interchangeably as Vitamin E) can be or include one or more vitamin E tocols selected from one or more vitamin E tocopherols and/or one or more vitamin E tocotrienols. Natural vitamin E tocols include two series of compounds: tocopherols with a saturated side chain and tocotrienols with an unsaturated side chain. Tocopherols and tocotrienols have a similar chemical structure, which is characterized by a long isoprenoid side chain attached at the 2 position of a 6-chromanol ring. Tocopherols include a chromanol ring and a 16-carbon tail. Tocotrienols differ from tocopherols in that they possess a farnesyl rather than a saturated isoprenoid C16 side chain. Vitamin E tocols (e.g., tocopherols and tocotrienols) are designated as α, β, γ, or δ based on the methylation pattern of the chromanol ring. δ- and γ- are dimethylated in the 5- and 8-positions or the 7- and 8-positions of the chromanol ring, respectively. α-tocols are trimethylated in the 5-, 7-, and 8-positions of the chromanol ring, and δ- are monomethylated in the 8-position of the chromanol ring. Vitamin E agents can include an α-, β-, γ-, or δ-tocol, or any mixture thereof. For example, vitamin E tocopherols can include any of one or more of tocopherols α, β, γ, and δ, as well as derivatives thereof. Vitamin E tocotrienols can include any of one or more of tocotrienols α, β, γ, and δ, as well as derivatives thereof. Of these vitamin E tocols, α-tocopherol and γ-tocopherol are the most abundant in nature. Certain commercially available vitamin E supplements can commonly include α-tocopherol. Certain commercially available vitamin E supplements can commonly include a mixture of vitamin E tocols having a variety of particular structures.

Vitamin E agents can include all stereoisomeric (e.g., enantiomeric or diastereomeric) forms of a vitamin E agent, as well as all geometric or conformational isomeric forms. For example, the R and S configurations of each stereocenter of a vitamin E agent are contemplated as part of the disclosure. Therefore, single stereochemical isomers, as well as enantiomeric, diastereomeric, and geometric (or conformational) mixtures of vitamin E agents are within the scope of the disclosure. For example, a Vitamin E agent can be or include a stereoisomer of a vitamin E tocopherol or tocotrienol. Tocopherol molecules have at least three stereocenters, at C-2, C-4' and C-8', making possible at least eight stereoisomers. For instance, a Vitamin E agent can be or include a stereoisomer of α-tocopherol selected from RRR, RRS, RSS, SSS, RSR, SRS, SRR, and SSR. In various embodiments, the RRR stereoisomer is naturally occurring. In some embodiments, a vitamin E agent includes a mixture of one or more stereoisomers, e.g., one or more α-tocopherol stereoisomers (e.g., 1, 2, 3, 4, 5, 6, 7, or 8 stereoisomers). Natural tocopherols occur in the RRR-configuration while synthetic forms can include eight different stereoisomers and is called all-rac-alpha-tocopherol. Tocotrienols possess only the stereocenter at C-2 and naturally occurring tocotrienols are exclusively in the 2R,3'E,7'E configuration.

Vitamin E agents include derivatives and/or analogs of vitamin E tocols. Vitamin E agents are amenable to various modifications, e.g., at the chroman moiety of vitamin E tocols. Examples of derivatives of vitamin E tocols include 2-, 5- or 6-substituted chroman derivatives. Vitamin E tocols can be derivatized by conjugation with an agent such as a peg moiety (pegylation) or an acid (e.g., hyaluronic acid).

A Vitamin E agent can be or include a prodrug of a vitamin E tocol, e.g., an ester of a vitamin E tocol (e.g., an ester of acetic acid, succinic acid, or nicotinic acid). In certain embodiments, an ester of a vitamin E agent is prepared from a phenol form of a vitamin E agent using conventional methods known in the art. Tocopheryl esters (e.g., alpha-tocopheryl acetate, tocopheryl succinate, tocopheryl nicotinate, tocopheryl linolate, alpha-tocopheryl phosphates, etc.) can demonstrate decreased susceptibility to oxidation. Tocopheryl esters can be de-esterified in the gut (e.g., by the enzyme esterase) and absorbed as free tocopherol. A Vitamin E agent can be or include an unesterified vitamin E tocol. In various embodiments, free and esterified Vitamin E tocols are understood to have comparable bioavailability.

The present disclosure includes that vitamin E agents that are absorbed, e.g., by the human body. The present disclosure includes both liquid and solid forms of vitamin E. Exemplary solid forms of vitamin E can be white to tan-white granular powders. Liquid forms of Vitamin E can be insoluble in water, soluble in alcohol, and/or miscible (e.g., with ether, acetone, vegetable oils, and/or chloroform). Various liquid forms of vitamin E can be clear, yellow to brownish red, and/or viscous oils. The present disclosure includes vitamin E agents that are fat soluble. For example, in various embodiments, solid forms such as alpha tocopheryl acid succinate are is insoluble in water but soluble in fat (e.g., vegetable oil), and in various embodiments can coat crystallized polypeptide and/or polypeptide particles.

Pharmaceutically acceptable carrier including a vitamin E agent can include a vitamin E agent (e.g., a fat soluble vitamin E agent) and an oil. In various embodiments Vitamin E may work as nutritional supplement in addition to carrier. In various embodiments, a pharmaceutically acceptable carrier including a vitamin E agent (e.g., an oil that includes naturally present or added vitamin E agent) can include a vitamin E agent and an oil that is a plant-derived oil, optionally wherein the plant derived oil is selected from wheat germ oil, hazelnut oil, canola/rapeseed oil, sunflower oil, safflower oil, almond oil, grapeseed oil, sunflower seed kernels, almonds, almond butter, wheat germ, canola oil, palm oil, peanut oil, margarine, tub, hazelnuts, corn oil, olive oil, soybean oil, pine nuts, peanut butter, and peanuts. Exemplary concentrations of vitamin E in certain such compositions are provided in Table 1. These provided concentrations are merely exemplary and in some instances reflect the amount of vitamin E agent typically or naturally present, while the present disclosure includes that the amount of vitamin E agent in oil compositions can be modified, e.g., by addition of vitamin E to achieve a vitamin E amount or concentration disclosed herein for use in a suspension or encapsulated formulation of crystallized or amorphous polypeptide.

17

TABLE 1

Oils and Vitamin E Agent Concentrations

| Plant source | Concentration of Vitamin E agent (mg Vitamin E agent/100 g) |
|---|---|
| Wheat germ oil | 150 |
| Hazelnut oil | 47 |
| Canola/rapeseed oil | 44 |
| Sunflower oil | 41.1 |
| Safflower oil | 34.1 |
| Almond oil | 39.2 |
| Grapeseed oil | 28.8 |
| Sunflower seed kernels | 26.1 |
| Almonds | 25.6 |
| Almond butter | 24.2 |
| Wheat germ | 19 |
| Canola oil | 17.5 |
| Palm oil | 15.9 |
| Peanut oil | 15.7 |
| Margarine, tub | 15.4 |
| Hazelnuts | 15.3 |
| Corn oil | 14.8 |
| Olive oil | 14.3 |
| Soybean oil | 12.1 |
| Pine nuts | 9.3 |
| Peanut butter | 9.0 |
| Peanuts | 8.3 |

Pharmaceutically Acceptable Carriers

Formulations of the present disclosure can include a pharmaceutically acceptable carrier that is or includes a vitamin E agent. As used herein, the term "pharmaceutically acceptable carrier" refers to a pharmaceutically-acceptable material, composition, or vehicle, such as a liquid or solid filler, diluent, excipient, or solvent encapsulating material, that facilitates formulation of an agent (e.g., a pharmaceutical agent), modifies bioavailability of an agent, or facilitates transport of an agent from one organ or portion of a subject to another. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients; oils, such as peanut oil, cottonseed oil, virgin coconut oil, almond oil, wheatgerm oil, any edible oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Excipients can include a non-therapeutic agent that may be included in a pharmaceutical composition, for example to provide or contribute to a desired consistency or stabilizing effect. In some embodiments, suitable pharmaceutical excipients may include, for example, starch, glucose, lactose, sucrose, gelatin, malt, rice, flour, chalk, silica gel, sodium stearate, glycerol monostearate, talc, sodium chloride, dried skim milk, cocoa butter, suppository waxes, glycerol, propylene, glycol, water, ethanol, or the like. In various embodiments, a polypeptide formulation of the present disclosure (e.g., the encapsulated core of a polypeptide formulation or suspension) further includes one or more pharmaceutically acceptable carriers. In various embodiments, one or more pharmaceutically acceptable carriers are selected from the group consisting of aggregation-reducing agents, sugars or sugar alcohols, polysaccharides, stabilizers, hyaluronidase, buffering agents, preservatives, carriers, antioxidants, chelating agents, natural or synthetic polymers, cryoprotectants, lyoprotectants, surfactants, bulking agents, acidifying agents, ingredients to reduce injection site discomfort, antifoaming agents, alkalizing agents, vehicles, aggregation inhibitors, solubilizing agents, tonicity modifiers, and stabilizing agents and combinations thereof.

In various embodiments, aggregation-reducing agents can include one or more of nicotinic acid, caffeine citrate, caffeine nicotinate, caffeine, octyl-β-D-glucopyranoside, and n-dodecyl-β-D-maltoside and optionally in combination with one or more of arginine, tryptophan, histidine, proline, cysteine, methionine, β-alanine, Potassium Glutamate, Arginine Ethylester, lysine, aspartic acid, glutamic acid, glycine, DTPA (diethylenetriaminepentaacetic acid), EGTA (aminopolycarboxylic acid), EDTA (Ethylenediaminetetraacetic acid), hydroxy propyl beta (HP-Beta) cyclodextrins, hydroxy propyl gamma (HP-Gamma) cyclodextrins, sulfobutyl ether (SBE) cyclodextrins, TMAO (trimethylamine N-oxide), trehalose, ethylene glycol, betaine, xylitol, sorbitol, 6-(N-(7-nitrobenz-2-oxa-1,3-diazol-4-yl)amino) hexanoic acid (NBD-X), methyl acetyl phosphate (MAP), citraconic anhydride, pyrophosphate, citrate, and combinations thereof.

In various embodiments, tonicity modifiers can include one or more of arginine, cysteine, histidine, glycine, sodium chloride, potassium chloride, sodium citrate, saccharides such as sucrose, glucose, dextrose, glycerin or mannitol, and combinations thereof.

In various embodiments, antioxidants can include one or more of glycine, lysine, EDTA, DTPA, sorbitol, mannitol, ascorbic acid, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, sodium thiosulfate, sulfur dioxide, tocopherol, and combinations thereof.

In various embodiments, lyoprotectants can include one or more of sucrose, lactose, trehalose, dextran, erythritol, arabitol, xylitol, sorbitol, maltose, lactulose, maltulose, glucitol, maltitol, lactitol, isomaltulose and mannitol; amino acids, such as arginine or histidine or proline or glycine; lyotropic salts, such as magnesium sulfate; propylene glycol, glycerol, poly(ethylene glycol), or poly(propylene glycol); gelatin, dextrins, modified starch, carboxymethyl cellulose, and combinations thereof.

In various embodiments, pharmaceutically acceptable carriers expressly exclude a pharmaceutically active agent. In various embodiments, pharmaceutically acceptable carriers expressly exclude one or more, or all, polypeptides.

In various embodiments in which a polypeptide formulation for oral delivery includes a core or suspension that includes an amorphous polypeptide composition or a crystallized polypeptide composition and a pharmaceutically acceptable carrier including a vitamin E agent, the core, suspension, or pharmaceutically acceptable carrier can be characterized by an amount of vitamin E agent that is at least 10%, 20%, 30%, 40%, 50%, 60%, 70%, 75%, 80%, 85%, 90%, or 95% by weight, by mole ratio, or by volume. In various embodiments, the core, suspension, or pharmaceutically acceptable carrier can be characterized by an amount of vitamin E agent that is between 10% and 90%, 20% and 90%, 30% and 90%, 40% and 90%, 50% and 90%, 60% and 90%, 70% and 90%, 80% and 90%, 10% and 70%, 20% and 70%, 30% and 70%, 40% and 70%, 50% and 70%, 60% and 70%, 10% and 50%, 20% and 50%, 30% and 50%, or 40% and 50% by weight, by mole ratio, or by volume.

Crystallized and Amorphous Polypeptides

The present disclosure includes oral formulations that include vitamin E and polypeptide (e.g., polypeptide present in an amorphous polypeptide composition or a crystallized polypeptide composition). Pharmaceutical agents can exist in a variety forms, including polymorphs, solvates, hydrates, salts, co-crystals and amorphous solids.

Amorphous polypeptide compositions can include compositions in which polypeptide molecules are disordered or essentially disordered. Amorphous polypeptides can lack or essentially lack long-range order of the positions of the atoms. In various embodiments, an amorphous polypeptide can be more soluble than a crystallized form of the same polypeptide. In certain embodiments, an amorphous polypeptide is a composition that has not been crystallized and/or has not been processed according to a method of crystallization. In certain embodiments, an amorphous polypeptide composition can include short-range order, residual crystallinity, polymorphic states, and regions of different density, none of which necessarily constitute long-range order. In various embodiments an amorphous polypeptide composition can include a fraction of crystallized polypeptide, e.g., a fraction of crystallized polypeptide that is less than 20% total polypeptide (e.g., less than 20%, 15%, 10%, 9%, 8%, 7%, 6%, 5%, 4%, 3%, 2%, 1%, 0.5%, or 0.1% crystallized polypeptide) by mass, volume, or mols. Techniques for determining the degree of crystallinity include XRD, DSC, solution calorimetry, water sorption, isothermal calorimetry, and thermally stimulated current (TSC). In various embodiments, an amorphous polypeptide compositions does not diffract X-rays in a coherent manner and/or powder X-ray diffraction patterns are broad halos with no or very few characteristic peaks.

In various embodiments, an amorphous polypeptide composition of the present disclosure includes an average and/or maximum particle size of less than 25 microns, e.g., less than 20, 15, 10, 5, 4, 3, 2, 1, or 0.5 microns, optionally wherein the particles have an average and/or maximum particle size that is between 0.5 microns and 1, 2, 3, 4, 5, 10, 15, 20, or 25 microns or wherein the particles of polypeptide have an average and/or maximum particle size that is between 1 micron and 1, 2, 3, 4, 5, 10, 15, 20, or 25 microns. In various embodiments, particles of a polypeptide composition of the present disclosure are microparticles of polypeptide.

Amorphous polypeptide compositions of the present disclosure include compositions that include a high proportion of amorphous and/or non-crystallized polypeptide (e.g., of a polypeptide characterized by a particular amino acid sequence) relative to other agents or types of agents. In various embodiments, an amorphous polypeptide composition of the present disclosure includes at least 1%, 2%, 3%, 4%, 5%, 6%, 7%, 8%, 9%, 10%, 20%, 30%, 40%, 50%, 60%, 70%, 75%, 80%, 85%, 90%, 95%, 96%, 97%, 98%, 99%, or 100% amorphous and/or non-crystallized polypeptide (e.g., of a polypeptide characterized by a particular amino acid sequence) by weight, mole ratio, or volume of the composition or of polypeptide present in the composition. In various embodiments, an amorphous polypeptide composition can be characterized by an amount of amorphous and/or non-crystallized polypeptide (e.g., of a polypeptide characterized by a particular amino acid sequence) that is between a lower bound of 1%, 2%, 3%, 4%, 5%, 6%, 7%, 8%, 9%, 10%, 20%, 30%, 40%, 50%, 60%, 70%, 75%, 80%, 85%, or 90% by weight, mole ratio, or volume of the composition or of polypeptide present in the composition and an upper bound of 10%, 20%, 30%, 40%, 50%, 60%, 70%, 75%, 80%, 85%, 90%, 95%, 96%, 97%, 98%, 99%, or 100% by weight, mole ratio, or volume of the composition or of polypeptide present in the composition.

In various embodiments, an amorphous polypeptide composition of the present disclosure is free, or substantially free, of non-polypeptide agents (and/or of agents other than amorphous polypeptide), e.g., where the amorphous polypeptide composition includes no more than 1%, 2%, 3%, 4%, 5%, 10%, 15%, 20%, 25%, or 30% of non-polypeptide agents (and/or of agents other than amorphous polypeptide) by weight, by mole ratio, or by volume. In various embodiments, an amorphous polypeptide composition of the present disclosure includes no more than 1%, 2%, 3%, 4%, 5%, 10%, 15%, 20%, 25%, 30%, 40%, 50%, 60%, 70%, 75%, 80%, 85%, 90%, or 95% of non-polypeptide agents (and/or of agents other than amorphous polypeptide) by weight, by mole ratio, or by volume. In various embodiments, an amorphous polypeptide composition includes particles of one or more particular polypeptides and is free or substantially free of other polypeptide agents (optionally including crystallized form(s) of the one or more particular polypeptides), e.g., where the amorphous polypeptide composition includes no more than 1%, 2%, 3%, 4%, 5%, 10%, 15%, 20%, 25%, or 30% of other polypeptide agents by weight, by mole ratio, or by volume. In various embodiments, an amorphous polypeptide composition includes no more than 1%, 2%, 3%, 4%, 5%, 10%, 15%, 20%, 25%, 30%, 40%, 50%, 60%, 70%, 75%, 80%, 85%, 90%, or 95% of other polypeptide agents by weight, by mole ratio, or by volume. In various embodiments, an amorphous polypeptide composition includes particles of one or more particular polypeptides and is free or substantially free of other agents (optionally including crystallized form(s) of the one or more particular polypeptides), e.g., where the amorphous polypeptide composition includes no more than 1%, 2%, 3%, 4%, 5%, 10%, 15%, 20%, 25%, or 30% of other agents by weight, by mole ratio, or by volume. In various embodiments, an amorphous polypeptide composition includes no more than 1%, 2%, 3%, 4%, 5%, 10%, 15%, 20%, 25%, 30%, 40%, 50%, 60%, 70%, 75%, 80%, 85%, 90%, or 95% of other agents by weight, by mole ratio, or by volume.

In various embodiments, an amorphous polypeptide composition of the present disclosure includes particles of one or more particular polypeptides where the particles of the one or more particular polypeptides are free, or substantially free, of non-polypeptide agents, e.g., where the particles include no more than 1%, 2%, 3%, 4%, 5%, 10%, 15%, 20%, 25%, or 30% of non-polypeptide agents by weight, by mole ratio, or by volume. In various embodiments, an amorphous polypeptide composition of the present disclosure includes particles of one or more particular polypeptides where the particles of the one or more particular polypeptides include no more than 1%, 2%, 3%, 4%, 5%, 10%, 15%, 20%, 25%, 30%, 40%, 50%, 60%, 70%, 75%, 80%, 85%, 90%, or 95% of non-polypeptide agents by weight, by mole ratio, or by volume. In various embodiments, an amorphous polypeptide composition of the present disclosure includes particles of one or more particular polypeptides where the particles of the one or more particular polypeptides are free, or substantially free, of other polypeptides, e.g., where the particles of the one or more particular polypeptides include no more than 1%, 2%, 3%, 4%, 5%, 10%, 15%, 20%, 25%, or 30% of other polypeptides by weight, by mole ratio, or by volume. In various embodiments, an amorphous polypeptide composition of the present disclosure includes particles of one or more particular polypeptides where the particles of the one or more particular polypeptides include no more than 1%, 2%, 3%, 4%, 5%, 10%, 15%, 20%, 25%, 30%, 40%, 50%, 60%, 70%, 75%, 80%, 85%, 90%, or 95% of other polypeptides by weight, by mole ratio, or by volume. In various embodiments, an amorphous polypeptide composition of the present disclosure includes particles of one or more particular polypeptides where the particles of the one or more particular polypeptides are free, or substantially free, of other agents (optionally including non-crystallized form(s) of the one or more particular polypeptides), e.g., where the particles of the one or more particular polypeptides include no more than 1%, 2%, 3%, 4%, 5%, 10%, 15%, 20%, 25%, or 30% of other agents by weight, by mole ratio, or by volume. In various embodiments, an amorphous polypeptide composition of the present disclosure includes particles of one or more particular polypeptides where the particles of the one or more particular polypeptides include no more than 1%, 2%, 3%, 4%, 5%, 10%, 15%, 20%, 25%, 30%, 40%, 50%, 60%, 70%, 75%, 80%, 85%, 90%, or 95% of other agents by weight, by mole ratio, or by volume.

Process for production of amorphous polypeptide compositions can include molecular quenching of melts, rapid precipitation by antisolvent addition, freeze-drying, spray-drying, spray-freeze-drying, precipitation in supercritical fluids, solid-dispersion, and solid-state chemical reactions (degradation) of crystalline precursors. For example, freeze drying of a protein/PEG blend solution and subsequent removal of PEG from the matrix has proven to yield precipitated protein particles in amorphous form. Processes that introduce mechanical or chemical stress (grinding, milling, and wet granulation) can render crystalline materials fully or partially amorphous.

In some embodiments, an amorphous polypeptide composition can be a hydrated form or prepared from a hydrated form. Hydrated forms can include an alcohol (e.g., ethanol). In some embodiments, an amorphous polypeptide composition is a solvated form or prepared form a solvated form. Exemplary solvents can include, for example, an acidic solvent or an organic solvent. In some embodiments, a solvent can include DMSO, DMF, acetic acid, acetonitrile, methanol, propanol, isopropanol, acetone, anisole, 1-butanol, 2-butanol, butyl acetate, fer/-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, tetrahydrofuran, ethanol, and/or water. Certain methods of preparing amorphous polypeptide compositions can include removal of a solvent by rapid solvent evaporation from a solvated form, spray drying, roller drying, solvent precipitation, or freeze drying. In some embodiments, an amorphous polypeptide composition includes a cation such as a 2+ charged cation (e.g., $Ba^{2+}$, $Ca^{2+}$, $Cr^{2+}$, $Co^{2+}$, $Cu^{2+}$, $Fe^{2+}$, $Pb^{2+}$, $Mg^{2+}$, $Mn^{2+}$, $Ni^{2+}$, $Sr^{2+}$, $Sn^{2+}$, or $Zn^{2+}$).

Crystal formation can include assembly of non-crystalline solid agents into a crystalline solid form. Crystal formation can utilize various molecular interactions, including, e.g., hydrogen bonding, p stacking, and Vander Waals Forces. Hydrogen bond formation is often responsible for intermolecular interactions in molecular solids. Crystallization is typically considered with respect to small molecule agents, and rarely considered with respect to polypeptides. Polypeptides typically lack well-defined conformation in solution. In certain embodiments, an amorphous polypeptide composition or a crystallized polypeptide composition is a powder form that includes crystals of polypeptide.

In various embodiments, a crystallized polypeptide composition of the present disclosure includes crystals of polypeptide having an average and/or maximum particle size of less than 25 microns, e.g., less than 20, 15, 10, 5, 4, 3, 2, 1, or 0.5 microns, optionally wherein the crystals of polypeptide have an average and/or maximum particle size that is between 0.5 microns and 1, 2, 3, 4, 5, 10, 15, 20, or 25 microns or wherein the crystals of polypeptide have an average and/or maximum particle size that is between 1 micron and 1, 2, 3, 4, 5, 10, 15, 20, or 25 microns. In various embodiments, crystals of a crystallized polypeptide composition of the present disclosure are microcrystals of polypeptide.

Crystallized polypeptide compositions of the present disclosure include compositions that include a high proportion of crystallized polypeptide (e.g., of a polypeptide characterized by a particular amino acid sequence) relative to other agents or types of agents. In various embodiments, a crystallized polypeptide composition of the present disclosure includes at least 1%, 2%, 3%, 4%, 5%, 6%, 7%, 8%, 9%, 10%, 20%, 30%, 40%, 50%, 60%, 70%, 75%, 80%, 85%, 90%, 95%, or 100% crystallized polypeptide (e.g., of a polypeptide characterized by a particular amino acid sequence) by weight, by mole ratio, or by volume of the composition or of polypeptide present in the composition. In various embodiments, a crystallized polypeptide composition can be characterized by an amount of crystallized polypeptide (e.g., of a polypeptide characterized by a particular amino acid sequence) that is between that is between a lower bound of 1%, 2%, 3%, 4%, 5%, 6%, 7%, 8%, 9%, 10%, 20%, 30%, 40%, 50%, 60%, 70%, 75%, 80%, 85%, or 90% by weight, mole ratio, or volume of the composition or of polypeptide present in the composition and an upper bound of 10%, 20%, 30%, 40%, 50%, 60%, 70%, 75%, 80%, 85%, 90%, 95%, 96%, 97%, 98%, 99%, or 100% by weight, mole ratio, or volume of the composition or of polypeptide present in the composition.

In various embodiments, a crystallized polypeptide composition of the present disclosure is free, or substantially free, of non-polypeptide agents e.g., where the crystallized polypeptide composition includes no more than 1%, 2%, 3%, 4%, 5%, 10%, 15%, 20%, 25%, or 30% of non-polypeptide agents by weight, by mole ratio, or by volume. In various embodiments, a crystallized polypeptide composition of the present disclosure includes no more than 1%, 2%, 3%, 4%, 5%, 10%, 15%, 20%, 25%, 30%, 40%, 50%, 60%, 70%, 75%, 80%, 85%, 90%, or 95% of non-polypeptide agents by weight, by mole ratio, or by volume. In various embodiments, a crystallized polypeptide composition includes crystals of one or more particular polypeptides and is free or substantially free of other polypeptide agents (optionally including non-crystallized form(s) of the one or more particular polypeptides), e.g., where the crystallized polypeptide composition includes no more than 1%, 2%, 3%, 4%, 5%, 10%, 15%, 20%, 25%, or 30% of other polypeptide agents by weight, by mole ratio, or by volume. In various embodiments, a crystallized polypeptide composition includes crystals of one or more particular polypeptides and includes no more than 1%, 2%, 3%, 4%, 5%, 10%, 15%, 20%, 25%, 30%, 40%, 50%, 60%, 70%, 75%, 80%, 85%, 90%, or 95% of other polypeptide agents by weight, by mole ratio, or by volume. In various embodiments, a crystallized polypeptide composition includes crystals of one or more particular polypeptides and is free or substantially free of other agents (optionally including non-crystallized form(s) of the one or more particular polypeptides), e.g., where the crystallized polypeptide composition includes no more than 1%, 2%, 3%, 4%, 5%, 10%, 15%, 20%, 25%, or 30% of other agents by weight, by mole ratio, or by volume. In various embodiments, a crystallized polypeptide composition includes crystals of one or more particular polypeptides and includes no more than 1%, 2%, 3%, 4%, 5%, 10%, 15%, 20%, 25%, 30%, 40%, 50%, 60%, 70%, 75%, 80%, 85%, 90%, or 95% of other agents by weight, by mole ratio, or by volume.

In various embodiments, a crystallized polypeptide composition of the present disclosure includes crystals of one or more particular polypeptides where the crystals of the one or more particular polypeptides are free, or substantially free, of non-polypeptide agents, e.g., where the crystals include no more than 1%, 2%, 3%, 4%, 5%, 10%, 15%, 20%, 25%, or 30% of non-polypeptide agents by weight, by mole ratio, or by volume. In various embodiments, a crystallized polypeptide composition of the present disclosure includes crystals of one or more particular polypeptides where the crystals include no more than 1%, 2%, 3%, 4%, 5%, 10%, 15%, 20%, 25%, 30%, 40%, 50%, 60%, 70%, 75%, 80%, 85%, 90%, or 95% of non-polypeptide agents by weight, by mole ratio, or by volume. In various embodiments, a crystallized polypeptide composition of the present disclosure includes crystals of one or more particular polypeptides where the crystals of the one or more particular polypeptides are free, or substantially free, of other polypeptides, e.g., where the crystals of the one or more particular polypeptides include no more than 1%, 2%, 3%, 4%, 5%, 10%, 15%, 20%, 25%, or 30% of other polypeptides by weight, by mole ratio, or by volume. In various embodiments, a crystallized polypeptide composition of the present disclosure includes crystals of one or more particular polypeptides where the crystals of the one or more particular polypeptides include no more than 1%, 2%, 3%, 4%, 5%, 10%, 15%, 20%, 25%, 30%, 40%, 50%, 60%, 70%, 75%, 80%, 85%, 90%, or 95% of other polypeptides by weight, by mole ratio, or by volume. In various embodiments, a crystallized polypeptide composition of the present disclosure includes crystals of one or more particular polypeptides where the crystals of the one or more particular polypeptides are free, or substantially free, of other agents (optionally including non-crystallized form(s) of the one or more particular polypeptides), e.g., where the crystals of the one or more particular polypeptides include no more than 1%, 2%, 3%, 4%, 5%, 10%, 15%, 20%, 25%, or 30% of other agents by weight, by mole ratio, or by volume. In various embodiments, a crystallized polypeptide composition of the present disclosure includes crystals of one or more particular polypeptides where the crystals of the one or more particular polypeptides include no more than 1%, 2%, 3%, 4%, 5%, 10%, 15%, 20%, 25%, 30%, 40%, 50%, 60%, 70%, 75%, 80%, 85%, 90%, or 95% of other agents by weight, by mole ratio, or by volume.

Polypeptide crystals can be prepared from a polypeptide sample. Polypeptide crystals can be prepared form a polypeptide sample that is substantially pure of other agents and/or contaminants. Polypeptide crystals can be prepared from an amorphous material, e.g., a lyophilized material that is amorphous or an amorphous solid that has been precipitated. In some embodiments, polypeptide crystals can be prepared from a mixture of amorphous and crystalline material, e.g., a lyophilized material that is a mixture of amorphous and crystalline material or a mixture of amorphous and crystalline solids that has been precipitated. In various embodiments, polypeptide crystals can be prepared form a polypeptide sample having a polypeptide concentration between 0.1 and 200 mg/ml, e.g., having a polypeptide concentration between a lower bound of 0.1, 1, 5, 10, 15, 20, 25, 50, 75, or 100 mg/ml and an upper bound of 15, 20, 25, 50, 75, 100, 125, 150, 175, or 200 mg/ml.

Means of polypeptide crystallization can include, without limitation, evaporation, slow diffusion (e.g., vapor diffusion at ambient or low temperature), slow cooling, slurrying, hanging drop, sitting drop, seeded crystal development, and/or other crystallization methods known in the art. Those of skill in the art will appreciate that many crystallization methods are well understood and known in the art, such that polypeptide crystallization is generally straightforward. Those of skill in the art will further appreciate that polypeptide crystallization is especially straight forward where a particular crystal size is not required, where large crystals are not required, where a particular crystalline form is not required, and/or where perfectly regular crystals are not required, any or all of which can characterize various embodiments of the present disclosure.

Crystalline polypeptides can be prepared by mixing a polypeptide in a suitable solvent (e.g., water) and then causing the polypeptide to return to the solid phase. For example, polypeptides can form crystals when precipitated from an aqueous solution (e.g., of ammonium sulfate). In certain exemplary embodiments, a polypeptide-saturated solution is prepared by increasing the concentration of the polypeptide in the solution. At maximal solubility, polypeptide precipitation can occur and the precipitant can be crystalline. Slow precipitation can produce small numbers of larger crystals while more rapid precipitation can produce very large numbers of small crystals, such that the rate of precipitation is therefore not critical to the production of crystals in general.

Evaporation (e.g., slow evaporation) is a common means of crystallizing polypeptides. Precipitation of a polypeptide can occur by allowing the solvent of a solution of polypeptide to evaporate (e.g., slowly evaporate) until the solution reaches saturation, thereby allowing polypeptide precipitation to occur.

Cooling (e.g., slow cooling) is another method of crystallizing polypeptides. Precipitation of a polypeptide can occur by allowing a solution of polypeptide to cool (e.g., slowly cool), thereby reducing the maximum solubility of the polypeptide in the solution and inducing precipitation to occur.

Vapor diffusion and batch methods are also commonly employed in polypeptide crystallization. In vapor diffusion, a drop containing a mixture of precipitant and unprecipitated polypeptide is sealed in a chamber with pure precipitant. Water vapor then diffuses out of the drop until the osmolarity of the drop and the precipitant are equal. The dehydration of the drop causes a slow concentration of both polypeptide and precipitant until equilibrium can be achieved, favoring crystallization. Vapor diffusion can be performed in either hanging-drop or sitting-drop format. A hanging-drop method can involve a drop of polypeptide solution placed on an inverted cover slip, which is then suspended above the reservoir. A sitting-drop method can position a drop on a pedestal that is separated from the reservoir. Both of these methods require sealing of the environment so that equilibration between the drop and reservoir can occur.

The batch method relies on bringing the polypeptide directly into the nucleation zone by mixing polypeptide with the appropriate amount of precipitant. Various Examples provided herein include batch crystallization. Batch crystallization is different from continuous crystallization in that the withdrawal of crystal product for the batch system is made only once at the end of the batch run. Batch crystallization may also include the semibatch system, in which one or more feed solutions are added to the crystallizer at a constant or variable rate throughout all or part of the batch. In various embodiments, batch crystallization can vary in volume from, e.g., 1 microliter (e.g., in an Eppendorf tube) to a liter or more (e.g., thousands of liters). In various embodiments, no vapor diffusion method is involved. In various embodiments, no evaporation is involved. In various embodiments, batch crystallization includes slowly adding precipitating reagents (e.g., with stirring if necessary, depending on batch size).

Typically, seeds of crystallizing material can be added early in the batch process in order to improve reproducibility and product quality. When a desired amount of solid has been formed, slurry is typically transferred to a solid-liquid separation unit.

Dialysis is another method commonly employed in polypeptide crystallization. This technique utilizes diffusion and equilibration of precipitant molecules through a semi-permeable membrane as a means of gradually approaching the concentration at which the macromolecule crystallizes. Dialysis tubes can be used in the case of large amounts of polypeptide being available.

Microdialysis buttons, also known as Cambridge buttons, offer a convenient way to produce crystals from a small amount of sample. A polypeptide sample is placed inside a small chamber on top of the button and the sample is covered with a dialysis membrane of appropriate molecular weight cut-off. The apparatus is then immersed in a reservoir containing precipitant solution. Equilibration of precipitant molecules can occur through the membrane.

Free interface diffusion can also be used to crystallize polypeptide. This technique can include carefully layering precipitant solution on top of concentrated polypeptide solution in a capillary, the ends of which are then sealed with wax. Narrow diameter of the capillary minimizes mixing from natural convection in the system. Thus, precipitant and polypeptide slowly inter-diffuse and the system reaches the equilibrium by a phenomenon called counter-diffusion. When the solutions initially come into contact and diffusive mixing occurs, the region of the polypeptide solution in the neighborhood of the interface becomes supersaturated and ideal conditions for nuclei formation are created. As time proceeds, the two solutions inter-diffuse along the axis of the capillary and dilute each other, thus promoting the dissolution of the smaller nuclei and the growth of the larger ones. The achievement, by the free liquid diffusion, of transient nucleation conditions in most cases allows to obtain high quality crystals. Thus free interface diffusion can be view as a rational crystallization approach to minimize supersaturation and impurity levels at the crystal growth front and to ensure steadiness of both values. A variant of free interface diffusion method is referred to as liquid bridge method, in which method a drop of polypeptide sample and a drop of precipitant solution are placed in close proximity on a cover glass and connected by a thin liquid bridge. The liquid diffusion between the two droplets, sealed from air, may induce crystal growth.

In some instances, crystallization nucleation can be induced by use of a material such as a nucleating agent, nucleant, or seed. Nucleation can occur on the surface of a nucleating agent, nucleant, or seed, which induces a higher local concentration of macromolecules, lowers the energy barrier for nucleation and bypasses kinetic barriers of spontaneous nucleation; a lower level of supersaturation can be required under such circumstances.

Pharmaceutical co-crystals can be crystalline materials comprised of a pharmaceutically active ingredient and one or more co-crystal formers ("coformers"), such that the active ingredient and coformers are together in the same crystal lattice. Co-crystals are distinguished from salts because unlike salts, the components that co-exist in the co-crystal lattice with a defined stoichiometry interact non-ionically. In addition, co-crystals differ from polymorphs, which are defined as including 1) single-component crystalline forms that have different arrangements or conformations of the molecules in the crystal lattice, 2) amorphous forms, and 3) multicomponent phases such as solvate and hydrate forms. Co-crystals are similar to solvates at least in that both contain more than one component in the lattice. In some embodiments, an amorphous polypeptide composition or a crystallized polypeptide composition of the present disclosure does not include co-crystallized polypeptide. In some embodiments, an amorphous polypeptide composition or a crystallized polypeptide composition of the present disclosure includes co-crystallized polypeptide.

Those of skill in the art will appreciate that a number of crystallization conditions can be adjusted to increase or decrease efficiency and/or purity of crystallization. For instance, crystallization conditions that can be adjusted include solubilization systems (aqueous systems and/or organic solvent systems), pH, counterions, salts, temperature, excipients, coformers, and polypeptide concentration. Modulating and testing ranges for these factors is trivial for those of skill in the art. In the art of crystallization, it is considered typical to sample a wide variety of crystallization conditions. Moreover, as those of skill in the art will appreciate, the present disclosure does not necessarily require that the most efficient form of crystallization be identified, only that crystals can be formed.

Crystallized polypeptide compositions of the present disclosure can include a plurality of crystallized polypeptides. In various embodiments, crystallized polypeptides can be characterized by high concentration, high purity, and/or high stability. Any suitable methods known in the art can be used to characterize provided crystallized polypeptide compositions, including but not limited to X-ray powder diffraction (XRPD), differential scanning calorimetry (DSC), thermogravimetric analysis (TGA), high-performance liquid chromatography (HPLC), liquid chromatography-mass spectrometry (LCMS), laser diffraction, hot stage microscopy, polarized light microscopy, and the like.

In various embodiments, an amorphous polypeptide composition or a crystallized polypeptide composition of the present disclosure is free, or substantially free, of one or more, or any, precipitation reagents, optionally wherein the precipitation reagents includes one or more of salts, organic solvents, or polymers, optionally where the salts can include a salt selected from ammonium sulfate, citrate salts, and cetyltrimethylammonium salts, the organic solvents can include an organic solvent selected from 2-methyl-2,4-pentanediol or 2-Methyl-2,4-pentanediol, and/or the polymers can include a polymer that is a polyethylene glycol.

In various embodiments, an amorphous polypeptide composition or a crystallized polypeptide composition of the present disclosure includes polypeptide crystals that are free, or substantially free, of one or more, or any, precipitation reagents, optionally wherein the precipitation reagents includes one or more of salts, organic solvents, or polymers, optionally where the salts can include a salt selected from ammonium sulfate, citrate salts, and cetyltrimethylammonium salts, the organic solvents can include an organic solvent selected from 2-methyl-2,4-pentanediol or 2-Methyl-2,4-pentanediol, and/or the polymers can include a polymer that is a polyethylene glycol.

Except where otherwise specified, those of skill in the art will appreciate that references relating to crystallization in the art refer to crystallization of molecules that are not polypeptides, e.g., to crystallization of molecules that are small molecules, e.g., small molecule therapeutics.

In various applications, peptide crystallization can produce well-ordered crystals with generally uniform content. While the present disclosure includes polypeptide compositions that include well-ordered crystals, the present disclosure also specifically includes the recognition that formulations of the present disclosure do not require crystals having a particular or consistent size or character. In various embodiments, crystallized polypeptide compositions include one or more crystalline forms of a polypeptide (e.g., one or more polymorphs or hydrates of a polypeptide).

In some embodiments, the polypeptide/peptide may be in aqueous form in the form of a droplet covered with Vitamin E. In other embodiments, a derivative of vitamin E which can dissolve in aqueous solution can be used as a carrier.

Those of skill in the art will appreciate from the present disclosure that compositions and methods provided herein are useful for the delivery of a wide variety of polypeptides. For example, those of skill in the art will appreciate from the present disclosure that compositions and methods provided herein are advantageous at least in part because they deliver polypeptides to the bloodstream and/or plasma after oral administration, e.g., through the lymphatic system, e.g., with advantageous pharmacokinetic properties.

In some embodiments, a polypeptide has a molecular weight that may be, for example, at least about 25 kDa, 50 kDa, 100 kDa, 150 kDa, 200 kDa, 250 kDa, 300 kDa, 400 kDa, 500 kDa, 1,000 kDa, or greater. Polypeptides of the present disclosure can have, e.g., molecular weights ranging from about 1 to about 1,000 kDa, e.g., from about 25 kDa to about 1,000 kDa, about 25 kDa to about 500 kDa, about 100 kDa to about 500 kDa, about 125 kDa to about 250 kDa, about 125 kDa to about 175 kDa, or about 150 kDa to about 300 kDa. In various embodiments, polypeptides of the present disclosure can have a molecular weight having a lower bound of e.g., about 1, 10, 20, 30, 40, 50, 75, 100, 150, 200, 250, 300, 350, 400, 450, or 500 kDa and an upper abound of, e.g., about 100, 150, 200, 250, 300, 350, 400, 450, 500, 750, or 1,000 kDa.

In some embodiments, a polypeptide has a molecular weight that may be, for example, between about 50 Da and 25 kDa, optionally wherein the molecular weight is between about 50 Da and about 1 kDa, about 50 Da and about 2 kDa, about 50 Da and about 3 kDa, about 50 Da and about 4 kDa, about 50 Da and about 5 kDa, about 50 Da and about 10 kDa, about 50 Da and about 15 kDa, or about 50 Da and about 20 kDa, In various embodiments, polypeptides of the present disclosure can have a molecular weight having a lower bound of e.g., about 50 Da, 100 Da, 150 Da, 200 Da, 250 Da, 300 Da, 400 Da, 500 Da, 600 Da, 700 Da, 800 Da, 900 Da, 1 kDa, 2 kDa, 3 kDa, 4 kDa, or 5 kDa and an upper abound of, e.g., about 250 Da, 300 Da, 400 Da, 500 Da, 600 Da, 700 Da, 800 Da, 900 Da, 1 kDa, 2 kDa, 3 kDa, 4 kDa, 5 kDa, 10 kDa, 15 kDa, 20 kDa, or 25 kDa.

Polypeptides of the present disclosure can include, e.g., about 1 to about 1,000 amino acids, e.g., about 10 to about 500, about 10 to about 250, about 10 to about 100, about 100 to about 1,000, about 100 to about 750, about 100 to about 500, about 100 to about 250, about 250 to about 1,000, about 250 to about 750, or about 250 to about 500 amino acids. In various embodiments, polypeptides of the present disclosure can include a number of amino acids having a lower bound of, e.g., about 1, 10, 20, 30, 40, 50, 75, 100, 150, 200, 250, 300, 350, 400, 450, or 500 amino acids and an upper abound of, e.g., about 100, 150, 200, 250, 300, 350, 400, 450, 500, 750, or 1,000 amino acids.

In various embodiments, a polypeptide of the present disclosure can be a therapeutic polypeptide, e.g., an enzyme or antibody, e.g., for administration to a subject in need thereof. Those of skill in the art will be familiar with the identities and character of a wide variety of therapeutic polypeptides.

In various embodiments, polypeptides of the present disclosure can be or include recombinant polypeptides, isolated or synthetic polypeptides, cytoskeletal proteins, extracellular matrix proteins, plasma proteins, coagulation factors, acute phase proteins, hemoproteins, cell adhesion proteins, transmembrane transport proteins, synport/antiport proteins, hormones, growth factors, receptors, transmembrane receptors, intracellular receptors, DNA-binding proteins, transcription regulation proteins, RNA-binding proteins, immune system proteins, nutrient storage and transport proteins, chaperone proteins, enzymes, glycoproteins, phosphoproteins, membrane proteins, transport proteins, or lipoproteins, antibodies, recombinant antibodies, antibody fragments, monoclonal antibodies, modified enzymes, pegylated polypeptides, therapeutic polypeptides, storage polypeptides, enzymes, growth factors or hormones, immunomodifiers, anti-infectives, antiproliferatives, vaccines or other therapeutics, prophylactic, diagnostic polypeptides, and combinations thereof.

In various embodiments, a polypeptide of the present disclosure can be or include an antibody or antibody fragment. In some embodiments, an antibody is a monoclonal antibody or fragment thereof. In some embodiments, an antibody is a polyclonal antibody or fragment thereof. In some embodiments, an antibody is natural, synthetic, or engineered.

Antibody fragments include Fab fragments (a single Fab that is isolated from a complete antibody by digestion with the enzyme papain) and F(ab')2 fragments (two Fabs covalently-bound to each other, produced by digesting the antibody with the enzyme pepsin). Fab fragments are monospecific, while F(ab')2 fragments are bispecific. Antibody fragments include include double-stranded Fv (dsFv) fragments and single-chain Fv (scFv) fragments (the "v" stands for "variable" in both cases). A dsFv fragment consists of a Fab fragment minus the constant regions, i.e., consisting only of the variable regions of a heavy and light chain covalently bound to each other. A scFv fragment is a single polypeptide chain, consisting of the variable region of a heavy chain linked via a peptide linker to the variable region of a light chain. Classically, both dsFv and scFv fragments are monovalent (and thus mono-specific). However, two dsFv fragments or two scFv fragments can themselves be linked to form a bispecific fragment (which would be analogous to a F(ab')2 fragment without the constant regions). Furthermore, it is possible to link two dsFv fragments or scFv fragments with different antigen-binding sites (i.e., different specificities), to form a bi-specific fragment. Such fragments may be used as either research tools or therapeutic or diagnostic reagents.

In some embodiments, an antibody is an immunoglobulin. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a "variable" ("V") region of about 100 to 110 or more amino acids which are primarily responsible for antigen recognition. The carboxy-terminal portion of each chain defines an invariable region primarily responsible for effector function. The four chains are arranged in a classic "Y" model. The bottom "leg" of the "Y" is called the Fc region ("c" stands for "crystallizable" or, alternatively, "complement-binding") and is used to anchor the antibody within cell membranes, and is also used to bind macrophage cells and thus activate complementation. The two "arms" at the top of the "Y" are called Fab regions (the "ab" stands for "antigen-binding"). Each Fab region contains an invariable region (at the junction of the Fab and the Fc regions) and a variable region (which extends to the tip of the "Y" or Fc region). Each variable region contains identical antigen-binding sites (at regions within the variable regions called "hypervariable" regions) at each tip of the "Y". The term "hypervariable" region refers to amino acid residues from a complementarity-determining region or CDR (i.e., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5th Ed. Public Health Service, National Institutes of Health, Bethesda, Md. (1991)). "Framework" or FR residues are the remaining variable region residues other than the hypervariable region residues. Each Fab region has one antigen-binding site, and the complete antibody molecule therefore has two antigen-binding sites (i.e., is "bivalent"). The two antigen-binding sites on a naturally occurring antibody are identical to each other, and therefore the antibody is specific for one antigen (i.e., is "monospecific").

Immunoglobulins can be assigned to different classes depending on the amino acid sequence of the invariable domain of their heavy chains. Heavy chains are classified as mu ($\mu$), delta ($\Delta$), gamma ($\gamma$), alpha ($\alpha$), and epsilon ($\epsilon$), and define the antibody's isotype as IgM, IgD, IgG, IgA, and IgE, respectively. Typically, IgG, IgE and IgD occur as monomers, while IgA can occur as not only a monomer, but also a dimer or trimer, and IgM can occur as a pentamer. Several of the above may be further divided into subclasses or isotypes, e.g. IgG1, IgG2, IgG3, IgG4, IgA1 and IgA2. Different isotypes have different effector functions; for example, IgG1 and IgG3 isotypes have antibody-dependent cellular cytotoxicity (ADCC) activities. Human light chains are classified as kappa ($\kappa$) and lambda ($\lambda$) light chains. Within light and heavy chains, the variable and invariable regions are joined by a "J" region of about 12 or more amino acids, with the heavy chain additionally encompassing a "D" region of about 10 more amino acids (See generally, Fundamental Immunology, Ch. 7 (Paul, W., ed., 2nd ed. Raven Press, N.Y. (1989)).

In some embodiments, a polypeptide may be a chimeric antibody. Though naturally occurring antibodies are derived from a single species, engineered antibodies and antibody fragments may be derived from more than one species of animal, i.e., may be chimeric. Mouse (murine)/human chimeric antibodies have been generated, though other combinations are possible. Chimeric antibodies have been further broken down into two subtypes: chimeric and humanized. Chimeric murine/human antibodies typically contain approximately 75% human and 25% mouse amino acid sequences, respectively. The human sequences represent invariable regions of an antibody while the mouse sequences represent variable regions (and thus contain the antigen-binding sites) of an antibody. The general rationale for using such chimeras is to retain antigen specificity of a mouse antibody but reduce the immunogenicity of a mouse anti-body (a murine antibody would cause an immune response against it in species other than the mouse) and thus be able to employ a chimera in human therapies. Chimeric antibodies also include those which include CDR regions from different human antibodies. CDR regions, also called hyper-variable regions, are sequences within variable regions of antibody molecules that generate antigen-binding sites. CDR regions are so-named because the binding site is complementary in shape and charge distribution to the epitope recognized on an antigen. Alternatively, chimeric antibodies include framework regions from one antibody and CDR regions from another antibody. Chimeric antibodies also include those which include CDR regions from at least two different human antibodies. Humanized antibodies typically contain approximately 90% (or more) human amino acid sequences. In this scenario, the only murine sequences present are those for a hypervariable region (that are the actual antigen-binding sites contained within a variable region). Humanized antibodies have minimal mouse immunogenicity as compared with chimeric antibodies.

Examples of antibodies and antibody fragments include, without limitation, Idarucizumab (Praxbind®), Raxibacumab (ABTHRAX®), Atezolizumab (TECENTRIQ®, RG7446 (Roche)), Ofatumumab (Arzerra®), Obinutuzumab (GAZYVA®, GA101 (Roche)), Bezlotoxumab (ZIN-PLAVA™), Necitumumab (Portrazza™), Obiltoxaximab (ANTHIM®), Olaratumab (Lartruvo™), Rituximab (RITUXAN®, ABP 798 (Amgen), MabThera®, GP2013 (Novartis)), Tositumomab (Bexxar®), Trastuzumab (HERCEPTIN®, ABP 980 (Amgen), HERTRAZ™, CANMAB™), Pertuzumab (PERJETA®, RG1273 (Roche)), Tocilizumab (ACTEMRA®), Bevacizumab (AVASTIN®, ABP 215 (Amgen)), Daratumumab (Darzalex®), Elotuzumab (EMPLICITI™), Siltuximab (SYLVANT™), Panitumumab (Vectibix®), Vedolizumab (Entyvio®), Eculizumab (Soliris®), Natalizumab (TYSABRI®), Cetuximab (ERBITUX®), Ipilimumab (YERVOY®), Reslizumab (CINQAIR®), Pembrolizumab (KEYTRUDA®), Nivolumab (OPDIVO®), Infliximab (REMICADE®, ABP 710 (Amgen), FLIXABI®), Abciximab (ReoPro®), Evolocumab (Repatha®), Secukinumab (Cosentyx®), Certolizumab pegol (Cimzia®), Ixekizumab (TALTZ™), Omalizumab (Xolair®), Canakinumab (Ilaris®), Alirocumab (Praluent®), Daclizumab (ZINBRYTA™, ZENAPAX®), Denosumab (XGEVA®), Denosumab (Prolia®), Mepolizumab (Nucala), Ustekinumab (Stelara®), Golimumab (Simponi®), Adalimumab (HUMIRA®, ABP501 (Amgen), GP2017 (Novartis)), Ramucirumab (CYRAMZA®), Ranibizumab (LUCENTIS®, RG3645 (Roche & Novartis)), Efalizumab (Raptiva®), Palivizumab (Synagis®), Adotrastuzumab emtansine (KADCYLA™) Alemtuzumab (Campath®), Alemtuzumab (LEMTRADA™), Basiliximab (Simulect®), Belimumab (Benlysta®), Blinatumomab (BLINCYTO®), Brentuximab vedotin (Adcetris), Capromab pendetide (ProstaScint®), Dinutuximab (Unituxin), Elotuzumab (EMPLICITI™), Gemtuzumab ozogamicin (Mylotarg), Ibritumomab tiuxetan (Zevalin®), Itolizumab (Alzumab™), Muromonab (Orthoclone OKT3®), Nimotuzumab (Theracim®), Nofetumomab (Verluma®), and biosimilars and combinations thereof. In various embodiments, examples of antibodies and antibody fragments include, without limitation, Abciximab, Palivizumab, Murumonab-CD3, Gemtuzumab, Trastuzumab, Basiliximab, Daclizumab, Etanercept, Ibritumomab, and/or Tiuxetan Examples of antibodies and antibody fragments include, without limitation, anti-cytokine antibodies, anti-CD antigen antibodies (e.g. anti-CD3, -CD20 (Rituximab), anti-CD25, anti-CD52, anti-CD33, and anti-CD11a), anti-TNF-α (e.g., Infliximab), anti-rattlesnake venom, anti-ICAM (e.g., anti-ICAM-1 and anti-ICAM-3), anti-growth factor antibodies (e.g., anti-VEGF), anti-growth factor receptor antibodies (e.g., anti-HER2/neu (Trastuzumab), and anti-EGFR), anti-immunoglobulin antibodies (e.g., anti-IgE), anti-polyclonal Ab antibodies, anti-viral antibodies (e.g., anti-CMV, anti-HIV (anti-gp120), anti-HBV, anti-RSV (anti-F glycoprotein)), anti-complement antibodies (e.g., anti-C5), anti-clotting factor antibodies (e.g., anti-gpIIb/IIIa and anti-Factor VII), anti-interleukin antibodies (e.g., anti-IL-5, anti-IL-4, and anti-IL-8), antibodies targeted to the Major Histocompatability Complex (e.g., anti-HLA), anti-idiotypic antibodies, anti-integrin antibodies (e.g., anti-β-2-integrin), anti-17-IA cell surface antigen, anti-α4β7, anti-VLA-4, anti-CBL, and combinations thereof.

In some embodiments, a polypeptide is a biosimilar antibody. A biosimilar is generally similar to the reference either physiochemically or biologically, both in terms of safety and efficacy. A biosimilar can be evaluated against a reference using one or more in vitro studies. In vitro comparisons may be combined with in vivo data demonstrating similarity of pharmacokinetics, pharmacodynamics, and/or safety. Clinical evaluations can include comparisons of pharmacokinetic properties (e.g. AUC0-inf, AUC0-t, Cmax, tmax, Ctrough); pharmacodynamic endpoints; or similarity of clinical efficacy (e.g. using randomized, parallel group comparative clinical trials). Differences between a biosimilar and a reference can include post-translational modification, e.g. by conjugating one or more biochemical groups such as a phosphate, various lipids and carbohydrates; by proteolytic cleavage following translation; by changing the chemical nature of an amino acid (e.g., formylation); or by many other mechanisms. Other post-translational modifications can be a consequence of manufacturing process operations—for example, glycation may occur with exposure of the product to reducing sugars. In other cases, storage conditions may be permissive for certain degradation pathways such as oxidation, deamidation, or aggregation.

Antibodies can generally be used, e.g., for the treatment of cancer, inflammation, cardiovascular disease, and transplant rejection, by virtue of their specific target-binding properties and/or target neutralization, e.g., binding and/or neutralization of targets associated with disease states. For example, the monoclonal antibody Infliximab binds to tumor necrosis factor and neutralizes its role in inflammation by blocking its interaction with a cell surface receptor. Rituximab targets malignant B lymphocytes by binding to their cell surface CD20 antigen. Clinically relevant antibodies may also be classified according to the therapeutic area in which they are to be employed. In some embodiments, a clinical antibody employed for therapeutic use may include those for treating cancers (e.g., pancreatic cancer), inflammatory diseases (e.g., autoimmune diseases, arthritis), cardiovascular diseases (e.g., strokes), infectious disease (e.g., HIV/AIDS), respiratory diseases (e.g., asthma), tissue transplantation rejection and organ transplantation rejection. In some embodiments, a clinical antibody is employed for radioimmunotherapy.

In various embodiments, a polypeptide of the present disclosure can be or include a polypeptide replacement therapy, an enzyme (such as a therapeutic replacement enzyme), and/or a fusion polypeptide. Examples of polypeptides and/or enzymes include, e.g., an antibody (e.g., an anti-HER2 antibody, e.g., trastuzumab), a GLP-1 receptor agonist, human glucagon-like peptide-1(GLP-1) or an analog thereof (e.g., a synthetic analog, e.g., liraglutide), parathyroid hormone or an analog thereof (e.g., recombinant human parathyroid hormone analog, e.g., teriparatide), insulin or an analog thereof (e.g., Humulin®), rituximab, bevacizumab, cetuximab, etanercept, infliximab, or an analog or derivative thereof. Examples of enzymes, e.g., for replacement enzyme therapy, can include agalsidase beta, agalsidase alfa, imiglucerase, aliglucerase alfa, velaglucerase alfa, alglucerase, sebelipase alpha, laronidase, idursulfase, elosulfase alpha, galsulfase, pancrelipase, sapropterin, eliglustat, galsulfase, asfotase alfa, pegvaliase, elapegademase, and/or sacrosidase. Examples of replacement polypeptides include Factor I, Factor II, Factor III, Factor IV, Factor V, Factor VI, Factor VII, Factor VIII, Factor IX, Factor X, Factor XI, Factor XII, Factor XIII, and/or von Willebrand factor. Examples of fusion polypeptides can include, e.g., etanercept, aflibercept, rilonacept, alefacept, romiplostim, abatacept/belatacept, and/or denileukin-diftitox. The present disclosure includes analogs and modified forms of polypeptides disclosed herein, e.g., that include one or more pendant groups or modifications, e.g., pegylation, acetylation, amidation, lipidation, methylation, phosphorylation, glycosylation, glycation, sulfation, mannosylation, nitrosylation, acylation, palmitoylation, prenylation, or combinations thereof. In various particular embodiments a polypeptide of the present disclosure includes one or more pendant groups or modifications selected from pegylation and/or fatty acids.

The present disclosure further includes engineered and/or biosimilar forms of polypeptides disclosed herein, e.g., having at least 80% sequence identity with a polypeptide disclosed herein, e.g., at least 80%, 85%, 90%, 95%, 96%, 97%, 98%, or 99% identity with a polypeptide disclosed herein.

The present disclosure further includes the recognition that polypeptides, including, e.g., antibodies and/or antibody fragments, are generally not referred to as "small molecules" or "compounds" in the art. Accordingly, because small molecules and compounds can have very different physical and pharmacokinetic properties than polypeptides as disclosed herein, e.g., than antibodies and/or antibody fragments, prior art disclosures relating to small molecules and compounds would not be understood as applicable by those of skill in the art to the formulations and methods relating to polypeptides as disclosed herein.

Pharmaceutically Acceptable Capsules

A core including an amorphous polypeptide composition or a crystallized polypeptide composition of the present disclosure can be encapsulated in a polymer capsule. Capsules of the present disclosure include pharmaceutically acceptable capsules suitable for oral administration or rectal administration. In various embodiments, capsules of the present disclosure are capsules suitable for delivery, e.g., specific delivery, of a polypeptide to the gut. In various embodiments, capsules of the present disclosure are capsules suitable for delivery, e.g., specific delivery, of a polypeptide to one or both the small intestine and/or large intestine.

Capsules of the present disclosure include hard-shell capsules and soft-shell capsules. In various embodiments, a capsule is a gelatin capsule or hydroxypropyl methylcellulose (HPMC) capsule. Exemplary capsule materials can include polymers such as poly(glycolic acid) (PGA), poly (lactic acid) (PLA) and its copolymers, poly(lactide-co-glycolide) (PLGA), and non-ionic cellulose ethers such as hydroxypropylcellulose (HPC) and hydroxypropyl methyl-cellulose (HPMC). In some embodiments a capsule is a vegetable capsule.

Soft gelatin capsules, also called softgels, can be produced from a single piece of gelatin. They can be used to encapsulate solutions not based on water, as water would dissolve the gelatin. Once ingested, the capsule dissolves, exposing the core.

Hard gelatin capsules are made of two parts, a body and a cap. Hard gelatin capsules can be filled with a core including dry ingredients in powder form. The body is first filled with a core composition, and the capsule is then closed with the cap. Once ingested, the hard capsules dissolves, exposing the core.

In various embodiments, a capsule can include an enteric coating. An enteric coating is typically a barrier that controls the location of a recipients body (e.g., digestive system, e.g., gut, e.g., small and/or large intestine) in which an oral formulation's core is exposed and/or to which the oral formulation's core is delivered. Many enteric coatings are insoluble at a low pH but dissolve, swells, or becomes soluble at a higher pH in the intestinal tract. Typical materials used for enteric coatings can include CAP (cellulose acetate phthalate), CAT (cellulose acetate trimellitate), PVAP (poly(vinyl acetate phthalate)) and HPMCP (hydroxy-propyl methylcellulose phthalate), poly(methacrylic acid-co-methyl methacrylate), fatty acids, waxes, shellac (e.g., esters of aleurtic acid), plastics, and plant fibers. In various embodiments, the dissolution pH of an enteric coating can be between, e.g., about 4.5 and about 7, e.g., about 4.5 to about 5.5, about 4.5 to about 6.0, about 5.5 to about 7.0, about 5.0, about 6.2, or about 7.0. In various embodiments an enteric coating has a pH release that is within a range that has a lower bound of about 4.5, 5.0, 5.5, or 6.0 and an upper bound of about 5.0, 5.5, 6.0, 6.5, 7.0, or 7.5.

The present disclosure expressly includes the recognition that enteric coatings are not necessary for delivery of a polypeptide disclosed herein according to methods and compositions of the present disclosure to reach the blood-stream, plasma, lymphatic system, and/or thoracic duct, e.g., in therapeutically effective amounts.

In various embodiments, a formulation of the present disclosure that includes an amorphous polypeptide composition or a crystallized polypeptide composition is or includes a bioadhesive formulation, e.g., in or on the surface of a capsule or tablet. In various embodiments, a bioadhesive formulation adheres to a specific biological location such as a mucosal lining (mucoadhesion). Bioadhesive dosage forms can improve the oral absorption of polypeptide agent by delivering it in small doses over an extended period and/or localizing it in the intestine by bioadhesion. Various bioadhesive polymers can be broadly as specific or nonspecific. Specific bioadhesive polymers (e.g., lectins, and fim-brins) have the ability to adhere to specific chemical structures within the biological molecules while the nonspecific bioadhesive polymers (e.g., polyacrylic acid [PAA] and cyanoacrylates) have the ability to bind with both the cell surfaces and the mucosal layer. Further examples of bioadhesive polymers include CMC sodium, Carbopol, Polycar-bophil, Tragacanth, Sodium alginate, HPMC, Gum karaya, Gelatin, Guar gum, Pectin, Acacia, Chitosan, and hydroxy-propyl cellulose. Examples of bioadhesive polymers can include Hydrophilic polymers (e.g., Methyl Cellulose, hydroxyethyl cellulose, HPMC, Na CMC, and carbomers), Thiolated polymers (e.g., Chitosan-iminothiolane, PAA-cys-teine, PAA-homocysteine, chitosan-thioglycolic acid, chito-san-thioethylamidine, alginate-cysteine, poly (methacrylic acid)-cysteine and sodium carboxymethylcellulose-cyste-ine), Lectin-based polymers (e.g., Lentil lectin, peanut agglutinin, and ulex europaeus agglutinin), Polyox WSR (e.g., WSR N-10, WSR N-80, WSR N-205, and WSR N-750), and other polymers such as tomato lectin, PAA-co-PEG, and PSA.

The present disclosure further includes suppositories suitable for rectal delivery. In various embodiments, suppositories melt or dissolve upon administration. In various embodiments, a suppository includes a capsule (e.g., a capsule disclosed herein, such as a hard gelatin capsule or a soft gelatin capsule) that encapsulates a core. In various embodiments, a suppository does not include a capsule (i.e., does not include a capsule that encapsulates a core). Suppositories can be formed from waxy matter, structured glycerine, hydrogenated vegetable oil, polyethylene glycol wax derivative, or poloxamer-based mixtures. In various embodiments, a suppository is solid at ambient temperature but rapidly melts at body temperature. Emulsifiers may be used to increase the solubility of crystallized polypeptide or amorphous polypeptide in the suppository mass and/or accelerate the dispersal of crystallized polypeptide or amor-phous polypeptide after the suppository melts.

In various embodiments, the present disclosure further includes tablets, fast dissolving tablets, liquid gel capsules, syrups, lozenges, aerosol spray, chewing gums and so on.

Formulations

The present disclosure includes methods and composi-tions that include apolypeptide formulation for oral or rectal delivery including a core within a pharmaceutically accept-able capsule or a suspension, where the core or suspension includes a polypeptide composition (e.g., an amorphous polypeptide composition or a crystallized polypeptide com-position) and a pharmaceutically acceptable carrier includ-ing a vitamin E agent.

In various embodiments, suspensions of the present dis-closure includes a suspension of an amorphous polypeptide composition or a crystallized polypeptide composition in a vitamin E agent and/or a pharmaceutically acceptable carrier including a vitamin E agent. Suspensions of the present disclosure include liquid formulations in which an amor-phous polypeptide agent or crystallized polypeptide agent is distribute in a suspension medium such as a vitamin E agent, a pharmaceutically acceptable carrier, or a combination thereof. In various embodiments, a suspension of the present disclosure can be a dilute suspension (e.g., a suspension including 10% or less of a polypeptide agent by weight or volume) or a concentrated suspension (e.g., a suspension including 10-50% or more of a polypeptide agent by weight or volume). In various embodiments, a suspension of the present disclosure can be a flocculated suspension or a deflocculated suspension. In various embodiments, a sus-pension can be a coarse suspension (e.g., of particles greater than 1 μm diameter), a colloidal suspension (e.g., of particles less than 1 μm diameter), or a nanosuspension (e.g., of particles between 1 and 100 nm diameter). Suspensions of the present disclosure can be administered, e.g., orally or rectally.

In various embodiments, the core or suspension includes about 1 mg to 2,000 mg of polypeptide (e.g., crystalized polypeptide or amorphous polypeptide). In various embodi-ments, the core or suspension includes about 1 mg to 1,000 mg, 1 mg to 500 mg, 1 mg to 400 mg, 1 mg to 300 mg, 1 mg to 200 mg, or 1 mg to 100 mg of crystalized polypeptide or amorphous polypeptide. In some embodiments the for-mulation includes an amount of crystalized polypeptide or amorphous polypeptide that has a lower bound of, e.g., 1, 5, 10, 15, 20, 25, 30, 35, 40, 45, 50, 75, 100, 150, 200, 250, 300, 350, 400, 450, or 500 mg crystalized polypeptide or amorphous polypeptide and an upper bound of 100, 150, 200, 250, 300, 350, 400, 450, 500, 1,000, or 2,000 mg crystalized polypeptide or amorphous polypeptide. In various embodiments, the core or suspension includes about 50 µg to 2,000 mg of the polypeptide, optionally wherein the polypeptide formulation includes about 50 µg to 1,000 mg, 50 µg to 500 mg, 50 µg to 400 mg, 50 µg to 300 mg, 50 µg to 200 mg, 50 µg to 100 mg, 50 µg to 50 mg, 50 µg to 25 mg, 50 µg to 20 mg, 50 µg to 15 mg, 50 µg to 10 mg, 50 µg to 5 mg, 50 µg to 1 mg, 50 µg to 500 µg, 1 mg to 1,000 mg, 1 mg to 500 mg, 1 mg to 400 mg, 1 mg to 300 mg, 1 mg to 200 mg, 1 mg to 100 mg, 1 mg, to 50 mg, 1 mg to 25 mg crystalized polypeptide or amorphous polypeptide. In various embodiments, the core or suspension includes about 1 µg to 2,000 mg of the polypeptide, optionally wherein the polypeptide formulation includes about 1 µg to 1,000 mg, 1 µg to 500 mg, 1 µg to 400 mg, 1 µg to 300 mg, 1 µg to 200 mg, 1 µg to 100 mg, 1 µg to 50 mg, 1 µg to 25 mg, 1 µg to 20 mg, 1 µg to 15 mg, 1 µg to 10 mg, 1 µg to 5 mg, 1 µg to 1 mg, 1 µg to 500 µg, 1 µg to 250 µg, 1 µg to 200 µg, 1 µg to 150 µg, 1 µg to 100 µg, 1 µg to 50 µg of the crystalized polypeptide or amorphous polypeptide. In some embodiments the formulation includes an amount of crystalized polypeptide or amorphous polypeptide that has a lower bound of, e.g., 1 µg, 5 µg, 10 µg, 15 µg, 20 µg, 25 µg 50 µg, 100 µg, 200 µg, 300 µg, 400 µg, 500 µg, 600 µg, 700 µg, 800 µg, 900 µg, 1 mg, 2 mg, 3 mg, 4 mg, 5 mg, 10 mg, or 25 mg crystalized polypeptide or amorphous polypeptide and an upper bound of 500 µg, 600 µg, 700 µg, 800 µg, 900 µg, 1 mg, 2 mg, 3 mg, 4 mg, 5 mg, 10 mg, 25 mg, 50 mg, 100 mg, 500 mg, 1,000 mg, or 2,000 mg crystalized polypeptide or amorphous polypeptide.

In various embodiments, a formulation of the present disclosure (e.g., an encapsulated or suspension formulation) and/or core thereof includes a molar excess or excess by weight of a vitamin E agent relative to the amount of crystalized polypeptide or amorphous polypeptide in the formulation, optionally where in the excess is a fold excess of at least 1.1, 1.5, 2, 3, 4, 5, 6, 7, 8, 9, 10, 20, 30, 40, 50, 60, 70, 80, 90, 100, 500, or 1,000 fold, e.g., a fold increase that is within a range of 1 to 10, 1 to 20, 1 to 30, 1 to 40, 1 to 50, 1 to 100, or 1 to 1,000. In various embodiments, the fold molar excess or excess by weight of vitamin E agent relative to the amount of crystalized polypeptide or amorphous polypeptide in the formulation is a fold increase that is within a range having a lower bound of 1, 2, 3, 4, 5, 6, 7, 8, 9, 10, 20, 30, 40, 50, 75, 100, 150, 200, or 250 and an upper bound of 30, 40, 50, 75, 100, 150, 200, 250, 500, or 1,000.

In various embodiments, one or more pharmaceutically acceptable carriers are present in a formulation of the present disclosure (e.g., an encapsulated or suspension formulation) or a core thereof at a concentration between 0.1 mM and about 1,000 mM, between about 0.1 mM and about 500 mM, between about 0.1 mM and about 200 mM. or between about 1 mM and about 100 mM. In various embodiments, one or more pharmaceutically acceptable carriers are present in a formulation of the present disclosure (e.g., an encapsulated or suspension formulation) or a core thereof at a concentration having a lower bound of 0.1, 1, 5, 10, 20, 30, 40, 50, 75, or 100 mM and an upper bound of 10, 20, 30, 40, 50, 75, 100, 150, 200, 250 or 500 mM.

Certain suppository formulations of the present disclosure can include an amorphous polypeptide composition or a crystallized polypeptide composition and suppository excipients, e.g., a lipophilic base (e.g., cocoa butter, coconut oil, virgin coconut oil, almond oil, wheatgerm oil, any edible oil, hydrogenated vegetable oils, and hard fats) or hydrophilic base (e.g., glycerinated gelatin and polyethylene glycols). Lipophilic bases are immiscible with body fluids and readily melt at body temperature to release the drug on the mucosal surface, whereas hydrophilic bases need to dissolve in the physiological fluids for drug release. Suppository formulations can include solid, semi-solid, and liquid forms.

In various embodiments, a suppository formulation of the present disclosure includes a semi-solid dosage form such as a gel or foam. A rectal gel can be a semi-solid formulations that contain a solvent trapped within a polymer network to create a viscous consistency. Viscosity of a gel can be modified by the addition of co-solvents (e.g., glycerin and propylene glycol) and electrolytes.

In various embodiments, a suppository formulation of the present disclosure includes a liquid suppository, e.g., a liquid suppository including thermosensitive polymers (e.g., poloxamers), mucoadhesive polymers (e.g., carbopol, sodium alginate, polycarbophil, hydroxypropyl methylcellulose, hydroxyethyl cellulose, and methylcellulose), or a combination of thermosensitive and mucoadhesive polymers. Suppositories can further include, e.g., cellulose ether polymers (e.g., hydroxypropyl methylcellulose, hydroxyethyl cellulose, and methylcellulose).

In various embodiments, a suppository formulation of the present disclosure includes a foam such as a colloidal dosage form with a hydrophilic liquid continuous phase containing a foaming agent and a gaseous dispersion phase distributed throughout. Following rectal administration, certain such formulations transition from a foam state to a liquid or semi-solid state on the mucosal surface. Foaming agents include amphiphilic substances that are important for foam generation and stabilization.

Further to the above, a pharmaceutical composition of the present disclosure can be in any form known in the art. Such forms include, e.g., liquid, semi-solid, and solid dosage forms, such as liquid solutions (e.g., injectable and infusible solutions), dispersions or suspensions, tablets, pills, powders, liposomes, and suppositories. Pharmaceutical compositions of the present disclosure can be administered enterally or topically, e.g., buccally. Pharmaceutical compositions of the present disclosure can be in the form of injectable or infusible solutions. Pharmaceutical compositions of the present disclosure can be formulated for administration by a parenteral mode (e.g., intravenous, subcutaneous, intraperitoneal, or intramuscular injection). As used herein, parenteral administration refers to modes of administration other than enteral and topical administration, e.g., by injection, and includes, without limitation, intravenous, intranasal, transnasal, intraocular, pulmonary, intrapulmonary, transpulmonary, intramuscular, intraarterial, intrathecal, intracapsular, intraorbital, intracardiac, intradermal, intraperitoneal, transtracheal, subcutaneous, transcutaneous, subcuticular, intraarticular, subcapsular, subarachnoid, intraspinal, epidural, intracerebral, intracranial, intracarotid, and intrasternal injection and infusion. A pharmaceutical composition can be administered parenterally in the form of an injectable formulation comprising a sterile solution or suspension. For example, a pharmaceutical composition can be formulated by suitably combining a polypeptide composition with one or more pharmaceutically acceptable carriers. Administration can be systemic or local.

In some embodiments, compositions can be formulated for intrapulmonary administration (e.g., for administration via an inhaler or nebulizer). Methods for formulating such compositions are well known in the art. Pulmonary administration may be oral and/or nasal. Examples of pharmaceutical devices for pulmonary delivery include metered dose inhalers, dry powder inhalers (DPIs), and nebulizers.

In some embodiments, compositions can be formulated for delivery to the eye, e.g., in the form of a pharmaceutically acceptable solution, suspension, or ointment, such as an eye drop. A preparation for use in treating an eye can be in the form of a sterile aqueous solution containing, e.g., additional ingredients such as, but not limited to, preservatives, buffers, tonicity agents, antioxidants and stabilizers, nonionic wetting or clarifying agents, and viscosity-increasing agents. A preparation as described herein can be administered topically to the eye of the subject in need of treatment by conventional methods, e.g., in the form of drops, or by bathing the eye in a therapeutic solution.

A suitable means of administration can be selected based on the age and condition of a subject. The amount of active ingredient included in the pharmaceutical preparations is such that a suitable dose within the designated range is provided. The dose and method of administration can vary depending on weight, age, condition, and other characteristics of a patient, and can be suitably selected as needed by those skilled in the art.

Polypeptide Delivery and Applications

Compositions and methods of the present disclosure include formulations for oral administration to a subject, where oral administration results in delivery of a polypeptide to the thoracic duct, lymphatic system, and/or bloodstream of a subject. Without wishing to be bound by any particular scientific theory the knowledge of the present inventors, the present disclosure is the first utilization of an oral formulation and/or an oral formulation including a vitamin E agent to deliver a polypeptide to the bloodstream via the thoracic duct and/or lymphatic system.

It was long assumed that vitamin E was absorbed by passive diffusion, but recent data has shown that this process is actually far more complex than previously thought. Without wishing to be bound by any particular scientific theory, vitamin E agent digestion following typical consumption of food, the first phase of the digestion-absorpstion process is the dissolution of vitamin E in the lipid phase of the meal. The fat digestion process starts in the mouth with lingual lipase and continues in the stomach with the addition of gastric lipase produced by chief cells. No metabolism of vitamin E (i.e., degradation or absorption) appears to exist in the stomach. The majority of fat digestion occurs in the duodenum by pancreatic lipase and colipase, with the assistance of emulsifying bile acids. Lipids are emulsified into lipid droplets at both gastric and duodenal levels. In addition, the size of the droplets does not seem to have any effect on the efficiency of the subsequent absorption of the vitamin E. In the duodenum, monoglycerides and long chain fatty acids resulting from lipolysis along with phospholipids, cholesterol, and fat-soluble vitamins, form micelles with bile salts. Vitamin E is incorporated, along with lipid digestion products, in mixed micelles, a step toward absorption by enterocytes. Mixed micelles can solubilize hydrophobic components and diffuse into the unstirred water layer (glycocalix) to approach the brush border membrane of the enterocytes. When approaching the brush border membrane, mixed micelles can dissociate due to the existing pH gradient. Released constituents can then be captured by different systems to be absorbed by the enterocyte, e.g., by passive diffusion and/or scavenger receptors. Once absorbed, the fate of vitamin E across the enterocyte has been poorly described. Being hydrophobic, vitamin E likely localizes into organelle membranes, cytosolic lipid droplets, or traffic bound to binding proteins. Subcellular localization revealed that vitamin E could accumulate in microsomal membranes, i.e., the endoplasmic reticulum, Golgi, lysosomal and peroxisomal membranes. Long chain fatty acids and monoglycerides are re-esterified into triglycerides and subsequently combined with polypeptide, phospholipid and cholesterol to form chylomicrons. Most of the vitamin E is incorporated into chylomicrons in its free form at the Golgi apparatus level before being released to the lymph. Following this, the chylomicrons enter the intestinal lymphatics through the thoracic duct and, finally, into the peripheral circulation. The lymphatic system circulates various immune system cells and is also a primary site of absorption for certain nutrients. Large molecular products of digestion can be absorbed into the lymphatic system before reaching systemic circulation through the venous system. Overall, mechanisms of vitamin E absorption remain only partially understood. Those of skill in the art will generally appreciate that the majority of vitamin E absorption occurs in the distal part of the intestine.

Without wishing to be bound by any particular scientific theory, the present inventors have surprisingly discovered that polypeptides orally administered in a core or suspension including vitamin E agent and polypeptide are efficiently delivered to the bloodstream, e.g., via the thoracic duct and/or lymphatic system. Accordingly, the present disclosure provides a platform or system of general, including compositions and methods disclosed herein, for delivery of diverse polypeptides to the thoracic duct, lymphatic system, and/or blood stream.

The present disclosure provides compositions and methods, e.g., for delivery of a polypeptide to a subject, e.g., to the thoracic duct, lymphatic system, and/or blood stream of the subject. In various embodiments, composition or method of the present disclosure delivers polypeptide to bloodstream with beneficial pharmacokinetic characteristics. In various embodiments, beneficial pharmacokinetic characteristics can result from distribution of the polypeptide through the lymphatic system, e.g., via the thoracic duct. Accordingly, the present disclosure specifically includes methods and compositions for delivery of a polypeptide to the lymphatic system, e.g., via the thoracic duct.

In various embodiments, a polypeptide of a polypeptide formulation is characterized in that it has a median, mean, or modal half-life across a plurality of samples, systems, and/or polypeptide molecules (e.g., across a plurality of subjects after oral administration of the polypeptide formulation to each subject) of at least 15 hours, optionally wherein the half-life is at least 20, 25, 30, 35, 40, 45, 50, 55, 60 hours, or more, optionally wherein the median, mean, or modal half-life is in a range having a lower bound of 30, 35, 40, 45, or 50 hours and an upper bound of 35, 40, 45, 50, 55, 60 hours, or more. In various embodiments, after oral administration to a subject of a polypeptide formulation of the present disclosure, the polypeptide of the polypeptide formulation has a half-life of at least 15 hours, optionally wherein the half-life is at least 20, 25, 30, 35, 40, 45, 50, 55, or 60 hours, or more, optionally wherein the half-life is in a range having a lower bound of 30, 35, 40, 45, or 50 hours and an upper bound of 35, 40, 45, 50, 55, 60 hours, or more.

In various embodiments, a polypeptide of a polypeptide formulation is characterized in that it has a median, mean, or modal half-life across a plurality of samples, systems, and/or polypeptide molecules (e.g., across a plurality of subjects after oral administration of the polypeptide formulation to each subject) that is at least 10% greater than the median, mean, or modal half-life achieved by injection (e.g., subcutaneous administration) of the polypeptide (e.g., according to a standard of care route of administration for the polypeptide) to a reference, optionally wherein the median, mean, or modal half-life of the polypeptide of the polypeptide formulation (e.g., after oral administration) is at least 20%, 30%, 40%, 50%, 60%, 70%, 80%, 90%, 100%, 2-fold, 3-fold, or 4-fold, greater than the median, mean, or modal half-life achieved by injection (e.g., subcutaneous administration) of the polypeptide (e.g., according to a standard of care route of administration for the polypeptide) to a reference. In various embodiments, after oral administration to a subject of the polypeptide formulation, the polypeptide of the polypeptide formulation has a half-life that is at least 10% greater than the half-life achieved by injection (e.g., subcutaneous administration) of the polypeptide (e.g., according to a standard of care route of administration for the polypeptide) to a reference, optionally wherein the half-life of the polypeptide of the polypeptide formulation after oral administration to the subject is at least 20%, 30%, 40%, 50%, 60%, 70%, 80%, 90%, 100%, 2-fold, 3-fold, or 4-fold, greater than the half-life achieved by injection (e.g., subcutaneous administration) of the polypeptide (e.g., according to a standard of care route of administration for the polypeptide) to a reference.

In various embodiments, a polypeptide of a polypeptide formulation is characterized in that it has a median, mean, or modal $T_{max}$ across a plurality of samples, systems, and/or polypeptide molecules (e.g., across a plurality of subjects after oral administration of the polypeptide formulation to each subject) that is at least 10% greater than the median, mean, or modal $T_{max}$ achieved by injection (e.g., subcutaneous administration) of the polypeptide (e.g., according to a standard of care route of administration for the polypeptide) to a reference, optionally wherein the median, mean, or modal $T_{max}$ of the polypeptide of the polypeptide formulation (e.g., after oral administration) is at least 20%, 30%, 40%, 50%, 60%, 70%, 80%, 90%, 100%, 2-fold, 3-fold, or 4-fold, 5-fold, 10-fold, or 20-fold greater than the median, mean, or modal $T_{max}$ achieved by injection (e.g., subcutaneous administration) of the polypeptide (e.g., according to a standard of care route of administration for the polypeptide) to a reference. In various embodiments, after oral administration to a subject of the polypeptide formulation, the polypeptide of the polypeptide formulation has a $T_{max}$ that is at least 10% greater than the $T_{max}$ achieved by injection (e.g., subcutaneous administration) of the polypeptide (e.g., according to a standard of care route of administration for the polypeptide) to a reference, optionally wherein the $T_{max}$ of the polypeptide of the polypeptide formulation after oral administration to the subject is at least 20%, 30%, 40%, 50%, 60%, 70%, 80%, 90%, 100%, 2-fold, 3-fold, or 4-fold, 5-fold, 10-fold, or 20-fold greater than the $T_{max}$ achieved by injection (e.g., subcutaneous administration) of the polypeptide (e.g., according to a standard of care route of administration for the polypeptide) to a reference.

In various embodiments, a polypeptide of a polypeptide formulation is characterized in that it has a median, mean, or modal bioavailability across a plurality of samples, systems, and/or polypeptide molecules (e.g., across a plurality of subjects after oral administration of the polypeptide formulation to each subject) that is at least 1% greater than the median, mean, or modal bioavailability achieved by injection (e.g., subcutaneous administration) of the polypeptide (e.g., according to a standard of care route of administration for the polypeptide) to a reference, optionally wherein the median, mean, or modal bioavailability of the polypeptide of the polypeptide formulation (e.g., after oral administration)

is at least 1%, 1.5%, 2%, 3%, 4%, 5%, 10%, 20%, 30%, 40%, 50%, 60%, 70%, 80%, 90%, 100%, 2-fold, 3-fold, 4-fold, or 5-fold greater than the median, mean, or modal bioavailability achieved by injection (e.g., subcutaneous administration) of the polypeptide (e.g., according to a standard of care route of administration for the polypeptide) to a reference. In various embodiments, after oral administration to a subject of the polypeptide formulation, the polypeptide of the polypeptide formulation has an bioavailability that is at least 1% greater than the bioavailability achieved by injection (e.g., subcutaneous administration) of the polypeptide (e.g., according to a standard of care route of administration for the polypeptide) to a reference, optionally wherein the bioavailability of the polypeptide of the polypeptide formulation after oral administration to the subject is at least 1%, 1.5%, 2%, 3%, 4%, 5%, 10%, 20%, 30%, 40%, 50%, 60%, 70%, 80%, 90%, 100%, 2-fold, 3-fold, 4-fold, or 5-fold greater than the bioavailability achieved by injection (e.g., subcutaneous administration) of the polypeptide (e.g., according to a standard of care route of administration for the polypeptide) to a reference. In various embodiments, a polypeptide of a polypeptide formulation is characterized in that it has a median, mean, or modal bioavailability across a plurality of samples, systems, and/or polypeptide molecules (e.g., across a plurality of subjects after oral administration of the polypeptide formulation to each subject) that is at least 1%, e.g., at least 1%, 1.5%, 2%, 3%, 4%, 5%, 10%, 20%, 30%, 40%, 50%, 60%, 70%, 80%, 90%, 100%

In various embodiments, a polypeptide of a polypeptide formulation is characterized in that it has a median, mean, or modal $C_{max}$ across a plurality of samples, systems, and/or polypeptide molecules (e.g., across a plurality of subjects after oral administration of the polypeptide formulation to each subject) that is at least 10% less than the median, mean, or modal $C_{max}$ achieved by injection (e.g., subcutaneous administration) of the polypeptide (e.g., according to a standard of care route of administration for the polypeptide) to a reference, optionally wherein the median, mean, or modal $C_{max}$ of the polypeptide of the polypeptide formulation (e.g., after oral administration) is at least 20%, 30%, 40%, 50%, 60%, 70%, 80%, or 90%, less than the median, mean, or modal $C_{max}$ achieved by injection (e.g., subcutaneous administration) of the polypeptide (e.g., according to a standard of care route of administration for the polypeptide) to a reference. In various embodiments, after oral administration to a subject of the polypeptide formulation, the polypeptide of the polypeptide formulation has a $C_{max}$ that is at least 10% less than the $C_{max}$ achieved by injection (e.g., subcutaneous administration) of the polypeptide (e.g., according to a standard of care route of administration for the polypeptide) to a reference, optionally wherein the $C_{max}$ of the polypeptide of the polypeptide formulation after oral administration to the subject is at least 20%, 30%, 40%, 50%, 60%, 70%, 80%, or 90%, less than the $C_{max}$ achieved by injection (e.g., subcutaneous administration) of the polypeptide (e.g., according to a standard of care route of administration for the polypeptide) to a reference.

In various embodiments, a method of the present disclosure can include administering a composition of the present disclosure to a subject in need thereof, where the composition includes a polypeptide for treatment of a disease or condition from which the subject suffers.

Further disclosed herein are methods of treating a disease or disorder in mammals, including administering to the mammal a composition of the present disclosure that includes a therapeutically effective amount of a polypeptide, and wherein a formulations further includes a pharmaceutically acceptable viscosity-reducing agent, aggregation-reducing agent, or other additive as described above; and wherein a therapeutic formulation is effective for treatment of a diseases or disorder. In some embodiments, a therapeutic formulation has improved stability when compared to a reference formulation. In some embodiments, an excipient compound is essentially pure.

In some embodiments, a therapeutic use for a composition of the present disclosure can include treatment and/or detection of cancers such as breast cancer, gastric cancer, Non-Hodgkin's Lymphoma, urothelial carcinoma & solid tumors, Metastatic colorectal cancer, Non-squamous non-small cell lung cancer, Metastatic breast cancer, Hodgkin lymphoma, Biliary cancer, Acute myeloid Leukemia, prostate cancer, multiple myeloma, solid tumors of bone, neuroblastoma, pancreatic cancer, acute myelogenous leukemia, metastatic melanoma, metastatic squamous non-small cell cancer, Anaplastic astrocytoma; Brain cancer, Glioblastoma, Glioma, Head and neck cancer, Merkel cell carcinoma, Nasopharyngeal cancer, Oesophageal cancer, Hepatocellular carcinoma, refractory euroblastoma, Osteosarcoma, Peritoneal cancer, Fallopian tube cancer, Mesothelioma, Metastatic Melanoma, Renal Cell Carcinoma, NR-LU-10 for cancer, lupus, Chronic Lymphocytic Leukemia, soft tissue sarcoma, ovarian cancer, bladder cancer, esophageal cancer, gastric nasopharyngeal cancer, adrenocortical carcinoma, HER2-positive breast cancer, adenocarcinoma, Granulomatosis with Polyangiitis (GPA), microscopic polyangiitis, idiopathic pulmonary fibrosis, focal segmental glomerulosclerosis, Prolactinoma, and combinations thereof.

In some embodiments, a therapeutic use for a composition of the present disclosure can include treatment and/or detection of an autoimmune disease such as Rheumatoid Arthritis (RA), Osteoarthritis, Juvenile Idiopathic Arthritis (JIA), Psoriatic Arthritis (PsA), Ankylosing Spondylitis (AS), Crohn's Disease (CD), Ulcerative Colitis (UC), Plaque Psoriasis (Ps), systemic lupus erythematosus, Lupus nephritis, Familial Cold Autoinflammatory Syndrome (FCAS), Sjogren's syndrome, and combinations thereof.

In some embodiments, a therapeutic use for a composition of the present disclosure can include treatment and/or detection of another immunologically-related disorder such as Leukopaenia, paroxysmal nocturnal hemoglobinuria (PNH), atypical hemolytic uremic syndrome (aHUS), thrombotic microangiopathy (TMA), Inflammatory bowel disease, ulcerative colitis and transplantation rejection, surgery-related, life-threatening, uncontrolled bleeding, and combinations thereof.

In some embodiments, a therapeutic use for a composition of the present disclosure can include treatment and/or detection of an infectious disease like *Clostridium difficile* infection, respiratory syncytial virus (RSV) disease, Anthrax, Flu virus infection, Influenza Virus infection, Hepatitis B virus infection, Rabies virus infection, invasive *Candida* infection, bacterial septic shock, HIV infection, Nosocomial pneumonia, Staphylococcal infections, STEC (Shiga-like toxin-producing *Escherichia coli* or *E. coli* serotype O121) infection causing diarrhea and HUS (hemolytic-uremic syndrome), Cytomegalovirus, Botulism, Ebola Virus, and combinations thereof.

In some embodiments, a therapeutic use for a composition of the present disclosure can include treatment and/or detection of a cardiovascular disease such as cardiac ischemic complications, percutaneous coronary intervention, Acute myocardial infarction, pulmonary embolism, deep vein thrombosis, arterial thrombosis or embolism, occlusion of arteriovenous cannula, thrombocytopenia with chronic immune (idiopathic) thrombocytopenic purpura (ITP), and combinations thereof.

In some embodiments, a therapeutic use for a composition of the present disclosure can include treatment and/or detection of an opthalmic disorder such as Age-Related Macular Degeneration (AMD), Macular Edema, Retinal Vein Occlusion (RVO), Diabetic Macular Edema, Neuromyelitis optica, and combinations thereof.

In some embodiments, a therapeutic use for a composition of the present disclosure can include treatment and/or detection of a respiratory disorder such as asthma, chronic idiopathic urticaria, acute bronchospasm or status asthmaticus, Chronic obstructive pulmonary disease, and combinations thereof.

In some embodiments, a therapeutic use for a composition of the present disclosure can include treatment and/or detection of a metabolic disorder like hyperlipidemia, Diabetes mellitus type-1 and 2, Hypercholesterolaemia, dyslipidemia, and combinations thereof.

In some embodiments, a therapeutic use for a composition of the present disclosure can include treatment and/or detection of a genetic disorder like Haemophilia A and B, Prader-Willi syndrome, Turner syndrome, Cryopyrin-Associated Periodic Syndromes (CAPS), Muckle-Wells Syndrome (MWS), X-linked hypophosphatemia, Sickle-cell pain crisis, and combinations thereof.

In some embodiments, a therapeutic use for a composition of the present disclosure can include treatment and/or detection of a bone-related ailment like Osteoporosis, aplastic anaemia, and combinations thereof.

In some embodiments, a therapeutic use for a composition of the present disclosure can include treatment and/or detection of other disorders including removal of venom; Alzheimer's disease, Back pain (Sciatic nerve pain), Migraine, Atopic dermatitis, Duchenne muscular dystrophy, Hepatic fibrosis, Cystic Fibrosis, Pseudomonas aeruginosa Infections, Ventilator-associated pneumonia, and combinations thereof.

In various embodiments, the present disclosure provides a method of producing a formulation of the present disclosure, including, e.g., steps of (1) preparing a core including an amorphous polypeptide composition or a crystallized polypeptide composition and a pharmaceutically acceptable carrier that includes a vitamin E agent, and (2) encapsulating the core in a pharmaceutically acceptable capsule. In various embodiments, the present disclosure provides a method of producing a formulation of the present disclosure, including, e.g., steps of (1) crystallizing a polypeptide to produce an amorphous polypeptide composition or a crystallized polypeptide composition; (2) preparing a core including the crystalized polypeptide or amorphous polypeptide composition and a pharmaceutically acceptable carrier that includes a vitamin E agent, and (3) encapsulating the core in a pharmaceutically acceptable capsule.

EXAMPLES

The following Examples demonstrate methods and compositions for oral administration of polypeptides that include a polypeptide and a vitamin E agent. The following Examples further demonstrate advantages of oral formulations of the present disclosure including improved half-life and bioavailability as compared to reference liquid formulations of the same polypeptides for administration by injection.

The present Examples provide formulation and testing of oral formulations including a polypeptide that is a crystallized polypeptide or amorphous polypeptide and a vitamin E agent. The present Examples utilize batch crystallization to produce crystallized polypeptide compositions. As those of skill in the art will appreciate from the present disclosure that the specific production method, size, size distribution, shape, and shape distribution of crystals is not an essential feature for the successful formulation of polypeptides in accordance with the methods and compositions provided herein. The present Examples expressly demonstrate that oral formulations of the present disclosure can be advantageously produced including amorphous polypeptide or crystallized polypeptide.

Example 1

Crystallization of Trastuzumab

The present Example demonstrates formation of crystallized trastuzumab for use in an oral formulation as disclosed herein. Trastuzumab is a humanized monoclonal antibody commercially available as Herclon® (Roche). Trastuzumab is an IgG1 kappa antibody that contains human framework regions with the complementarity-determining regions of a murine antibody (4D5) that binds with HER2. Trastuzumab has been widely used to treat breast cancer which overexpresses the extracellular domain of the epidermal growth factor receptor 2 protein, HER2. The present Example includes the recognition that trastuzumab is exemplary of polypeptides for which an oral formulation would be advantageous.

Trastuzumab was stored in its original 440 mg vial as a sterile lyophilized powder and was subsequently dissolved in 5 ml of sterile water. The dissolved Trastuzumab solution included 88 mg/ml Trastuzumab, 39.6 mg L-histidine HCl, 25.6 mg L-histidine, 1600 mg α,α-trehalose dihydrate, and 7.2 mg polysorbate 20, USP.

To produce trastuzumab microparticles, a 500 µl aliquot of Trastuzumab (88 mg/ml), in a buffer containing 3.96 mg/ml L-histidine HCl, 2.56 mg/ml L-histidine, 160 mg/ml α,α-trehalose dihydrate, and 0.72 mg/ml polysorbate 20, USP, was mixed with 1,000 µl of reagent containing 20% PEG 300, 10% PEG 8000, 10% glycerol, 100 mM Tris, pH 8.5, and incubated at room temperature overnight. The final concentration of the Trastuzumab in solution was 29.33 mg/ml. This mixture was then mixed using a votex and left at room temperature. Trastuzumab microparticles were obtained on the following day. (FIG. 1). 95% of the input Trastuzumab formed microparticles by this method.

Example 2

Crystallization of Liraglutide

The present Example demonstrates formation of crystallized Liraglutide for use in an oral formulation as disclosed herein. Liraglutide is marketed under the brand name Victoza® (Novo Nordisk). Liraglutide is a synthetic analog of human glucagon-like peptide-1 (GLP-1) produced using recombinant technology and acts as a GLP-1 receptor agonist. Liraglutide is 97% homologous to native human GLP-1, substituting arginine for lysine at position 34. Liraglutide includes a C-16 fatty acid (palmitic acid) with a glutamic acid spacer on the remaining lysine residue at position 26 of the peptide precursor. Liraglutide's therapeutic effects including increasing insulin release from the pancreas and decreasing excessive glucagon release. The present Example includes the recognition that Liraglutide is exemplary of polypeptides for which an oral formulation would be advantageous.

Liraglutide half-life is an important consideration in therapeutic use. Endogenous GLP-1 has a plasma half-life of 1.5-2 minutes due to degradation by the ubiquitous enzymes, dipeptidyl peptidase-4 (DPP4) and neutral endopeptidase (NEP). The half-life after intramuscular injection is approximately half an hour, so even administered this way, it has limited use as a therapeutic agent. The metabolically active forms of GLP-1 are the endogenous GLP-1-(7-36)NH$_2$ and the more rare GLP-1-(7-37). Prolonged action of liraglutide is achieved by attaching a fatty acid molecule at one position of the GLP-1-(7-37) molecule, enabling it to both self-associate and bind to albumin. The active GLP-1 is then released from albumin at a slow, consistent rate.

For use in the present Example, liraglutide was acquired as VICTOZA, a clear, colorless or almost colorless solution. Each 1 mL of VICTOZA solution contains 6 mg of liraglutide and the following inactive ingredients: disodium phosphate dihydrate, 1.42 mg; propylene glycol, 14 mg; phenol, 5.5 mg; and water for injection. Each pre-filled pen contains a 3 mL solution of VICTOZA equivalent to 18 mg liraglutide (free-base, anhydrous).

To produce Liraglutide microparticles, liraglutide was dialyzed against water for 24 hr with three changes and lyophilized to get dry powder. The lyophilized powder of liraglutide was then dissolved in water at a concentration of 80 mg/mL. Liraglutide aliquots were then crystalized using a variety of methods described below.

Figure 2:
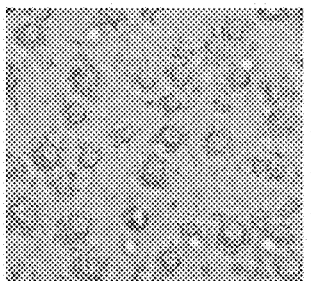
FIG. 2 is an image showing microparticles of liraglutide produced by a typical crystallization approach known to those of skill in the art.

Crystallization method 1: A 500 µl aliquot of Liraglutide (80 mg/ml), in water was mixed with 1,000 µl of reagent containing 1.34M Ammonium sulfate, 3.35% (v/v) PEG 400, 0.05M Magnesium sulfate, 0.1M Tris base/Hydrochloric acid pH 8.5, and incubated at room temperature overnight. The final concentration of the liraglutide in solution was 26.67 mg/ml. This mixture was then mixed using a votex and left at room temperature. Liraglutide microparticles were obtained on the following day. (FIG. 2). 75% of the input Liraglutide formed microparticles by this method.

Figure 3:
FIG. 3 is an image showing microparticles of liraglutide produced by a typical crystallization approach known to those of skill in the art.

Crystallization method 2: A 500 µl aliquot of Liraglutide (80 mg/ml), in water was mixed with 1,000 µl of reagent containing 35% (v/v) MPD, 100 mM Tris base/Hydrochloric acid pH 7.0, 200 mM Sodium chloride, and incubated at room temperature overnight. The final concentration of the liraglutide in solution was 26.67 mg/ml. This mixture was then mixed using a votex and left at room temperature. Liraglutide microparticles were obtained on the following day. (FIG. 3). 85% of the input liraglutide formed microparticles by this method.

Figure 4:
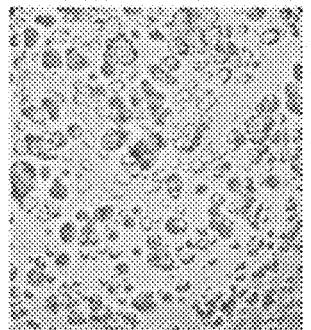
FIG. 4 is an image showing microparticles of liraglutide produced by a typical crystallization approach known to those of skill in the art.

Crystallization method 3: A 500 µl aliquot of Liraglutide (80 mg/ml), in water was mixed with 1,000 µl of reagent containing 1,000 mM Ammonium phosphate dibasic 100 mM Sodium citrate/Citric acid pH 5.5, 200 mM Sodium chloride, and incubated at room temperature overnight. The final concentration of the liraglutide in solution was 26.67 mg/ml. This mixture was then mixed using a votex and left at room temperature. Liraglutide microparticles were obtained on the following day. (FIG. 4). 90% of the input liraglutide formed microparticles by this method.

Figure 5:
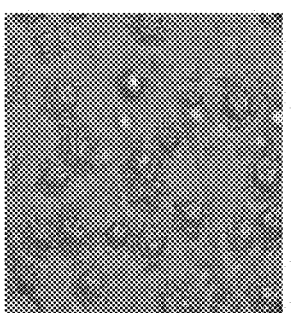
FIG. 5 is an image showing microparticles of liraglutide produced by a typical crystallization approach known to those of skill in the art.

Crystallization method 4: A 500 µl aliquot of Liraglutide (80 mg/ml), in water was mixed with 1,000 µl of reagent containing 25% (w/v) PEG 1500, 100 mM SPG buffer pH 8.5, and incubated at room temperature overnight. The final concentration of the liraglutide in solution was 26.67 mg/ml. This mixture was then mixed using a votex and left at room temperature. Liraglutide microparticles were obtained on the following day. (FIG. 5). 85% of the input liraglutide formed microparticles by this method.

Figure 6:
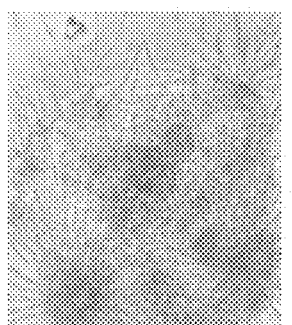
FIG. 6 is an image showing microparticles of liraglutide produced by a typical crystallization approach known to those of skill in the art.

Crystallization method 5: A 500 μl aliquot of Liraglutide (80 mg/ml), in water was mixed with 1,000 μl of reagent containing 40% (v/v) Ethylene glycol, 100 mM MES/Sodium hydroxide pH 6.0, 200 mM Zinc acetate, and incubated at room temperature overnight. The final concentration of the liraglutide in solution was 26.67 mg/ml. This mixture was then mixed using a votex and left at room temperature. Liraglutide microparticles were obtained on the following day. (FIG. 6). 75% of the input liraglutide formed microparticles by this method.

Figure 7:
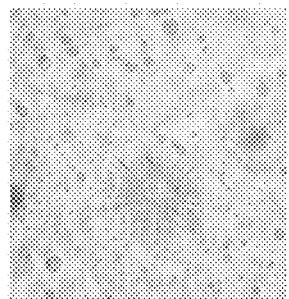
FIG. 7 is an image showing microparticles of liraglutide produced by a typical crystallization approach known to those of skill in the art.

Crystallization method 6: A 500 μl aliquot of Liraglutide (80 mg/ml), in water was mixed with 1,000 μl of reagent containing 3M Sodium chloride, 5% (v/v) MPD, 0.1M Calcium chloride, 0.1M Imidazole/Hydrochloric acid pH 6.5, and incubated at room temperature overnight. The final concentration of the liraglutide in solution was 26.67 mg/ml. This mixture was then mixed using a votex and left at room temperature. Liraglutide microparticles were obtained on the following day. (FIG. 7). 80% of the input liraglutide formed microparticles by this method.

Figure 8:
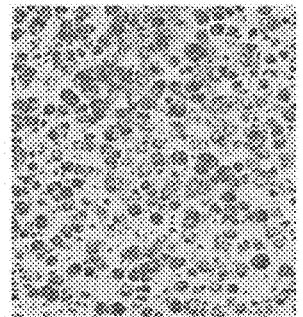
FIG. 8 is an image showing microparticles of liraglutide produced by a typical crystallization approach known to those of skill in the art.

Crystallization method 7: A 500 μl aliquot of Liraglutide (80 mg/ml), in water was mixed with 1,000 μl of reagent containing 0.429M Sodium chloride, 9.9% (v/v) Isopropanol, 0.1M Calcium chloride, 0.1M Imidazole/Hydrochloric acid pH 6.5, and incubated at room temperature overnight. The final concentration of the liraglutide in solution was 26.67 mg/ml. This mixture was then mixed using a votex and left at room temperature. Liraglutide microparticles were obtained on the following day. (FIG. 8). 70% of the input liraglutide formed microparticles by this method.

Figure 9:
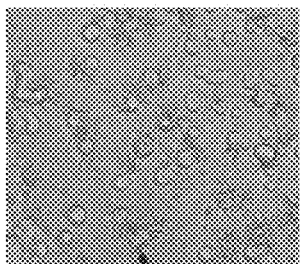
FIG. 9 is an image showing microparticles of liraglutide produced by a typical crystallization approach known to those of skill in the art.

Crystallization method 8: A 500 μl aliquot of Liraglutide (80 mg/ml), in water was mixed with 1,000 μl of reagent containing 5.36% (v/v) MPD, 0.67M Potassium phosphate dibasic/Sodium phosphate monobasic pH 8.5, and incubated at room temperature overnight. The final concentration of the liraglutide in solution was 26.67 mg/ml. This mixture was then mixed using a votex and left at room temperature. Liraglutide microparticles were obtained on the following day. (FIG. 9). 85% of the input liraglutide formed microparticles by this method.

Example 3

Crystallization of Insulin

The present Example demonstrates formation of crystallized insulin for use in an oral formulation as disclosed herein. Humulin® R is a polypeptide hormone structurally identical to human insulin synthesized through rDNA technology in a non-disease-producing laboratory strain of *Escherichia coli* bacteria. Humulin R is indicated as an adjunct to diet and exercise to improve glycemic control in adults and children with type 1 and type 2 diabetes mellitus. Humulin R, when used subcutaneously, is usually given three or more times daily before meals. The present Example includes the recognition that insulin is exemplary of polypeptides for which an oral formulation would be advantageous.

The present Example utilizes Humulin R (insulin (human recombinant)) U-100 (100 units per mL). To produce insulin microparticles, Insulin (Sigma Chemical Company) was desalted using 0.01N NaOH as follows. 62 mg of insulin dissolved in 4 mL of 0.01N HCl, pH 2.0. The pH of the polypeptide solution was increased by adding 10 uL of 0.1N NaOH each time until polypeptide is precipitated. The precipitated polypeptide was collected and washed twice in 5 mL of water, each time collecting the water separately. To the collected water 0.1N NaOH was added to collect the dissolved polypeptide from water. Finally all precipitate was dissolved in 1 mL of 0.01N HCl. Insulin aliquots were then crystalized using a variety of methods described below.

Figure 10:
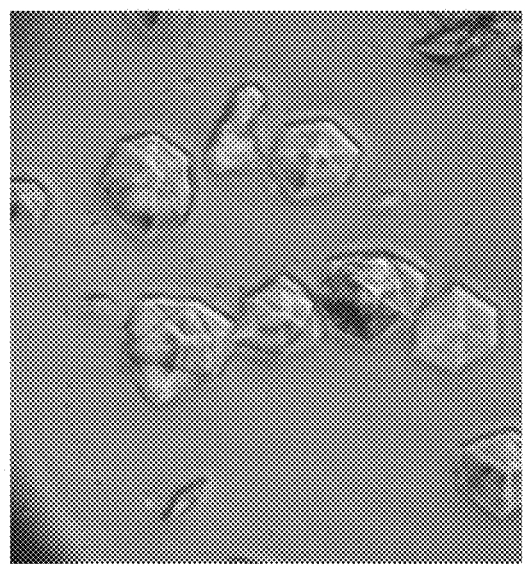
FIG. 10 is an image showing microparticles of insulin produced by a typical crystallization approach known to those of skill in the art.

Crystallization Method 1: A 500 μl aliquot of Insulin (~62 mg/ml), in water was mixed with 1,000 μl of reagent containing 40% (v/v) PEG 300, 100 mM Sodium cacodylate/Hydrochloric acid pH 6.5, 200 mM Calcium acetate, and incubated at room temperature overnight. The final concentration of the insulin in solution was 15.5 mg/ml. This mixture was then mixed using a votex and left at room temperature. Insulin microparticles were obtained on the following day. (FIG. 10). 90% of the input Insulin formed microparticles by this method.

Figure 11:
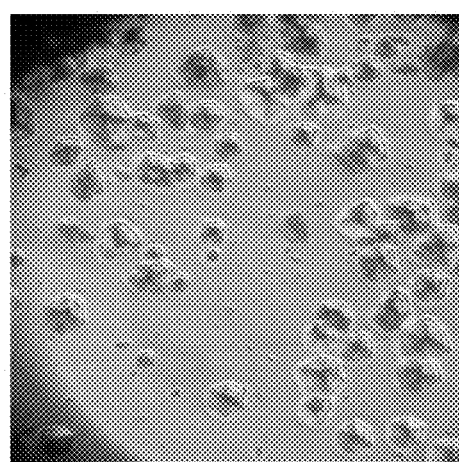
FIG. 11 is an image showing microparticles of insulin produced by a typical crystallization approach known to those of skill in the art.

Crystallization Method 2: A 500 μl aliquot of insulin (~62 mg/ml), in water was mixed with 1,000 μl of reagent containing 40% (v/v) PEG 600, 100 mM Sodium cacodylate/Hydrochloric acid pH 6.5, 200 mM Calcium acetate, and incubated at room temperature overnight. The final concentration of the insulin in solution was 15.5 mg/ml. This mixture was then mixed using a votex and left at room temperature. Insulin microparticles were obtained on the following day. (FIG. 11). 90% of the input Insulin formed microparticles by this method.

Figure 12:
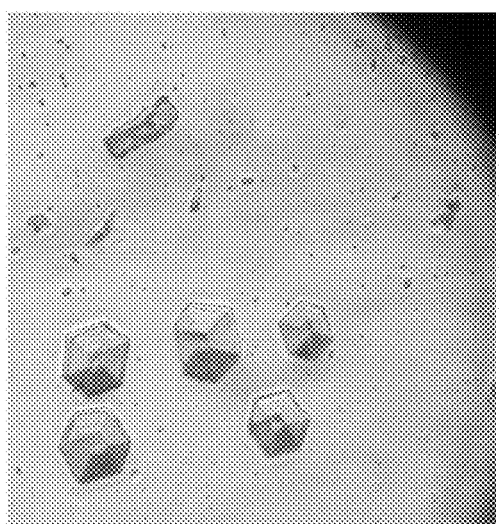
FIG. 12 is an image showing microparticles of insulin produced by a typical crystallization approach known to those of skill in the art.

Crystallization Method 3: A 500 μl aliquot of insulin (~62 mg/ml), in water was mixed with 1,000 μl of reagent containing 40% (v/v) 1,2-Propanediol, 100 mM Sodium acetate/Acetic acid pH 4.5, 50 mM Calcium acetate, and incubated at room temperature overnight. The final concentration of the insulin in solution was 15.5 mg/ml. This mixture was then mixed using a votex and left at room temperature. Insulin microparticles were obtained on the following day. (FIG. 12). 90% of the input Insulin formed microparticles by this method.

Figure 13:
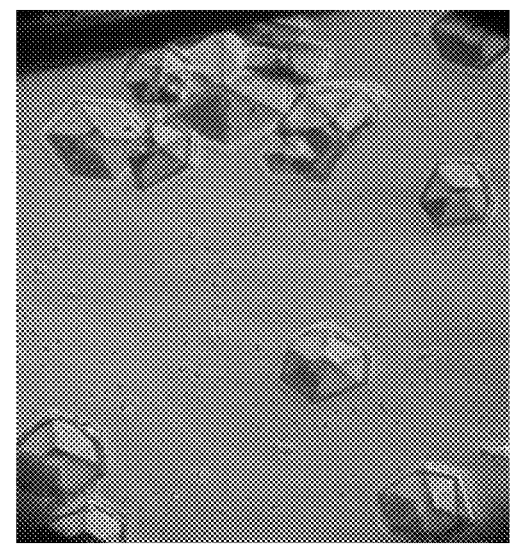
FIG. 13 is an image showing microparticles of insulin produced by a typical crystallization approach known to those of skill in the art.

Crystallization Method 4: A 500 μl aliquot of insulin (~62 mg/ml), in water was mixed with 1,000 μl of reagent containing 14.4% (w/v) PEG 8000, 80 mM Sodium cacodylate/Hydrochloric acid pH 6.5, 160 mM Calcium acetate, 20% (v/v) Glycerol, and incubated at room temperature overnight. The final concentration of the insulin in solution was 15.5 mg/ml. This mixture was then mixed using a votex and left at room temperature. Insulin microparticles were obtained on the following day. (FIG. 13). 90% of the input Insulin formed microparticles by this method.

Figure 14:
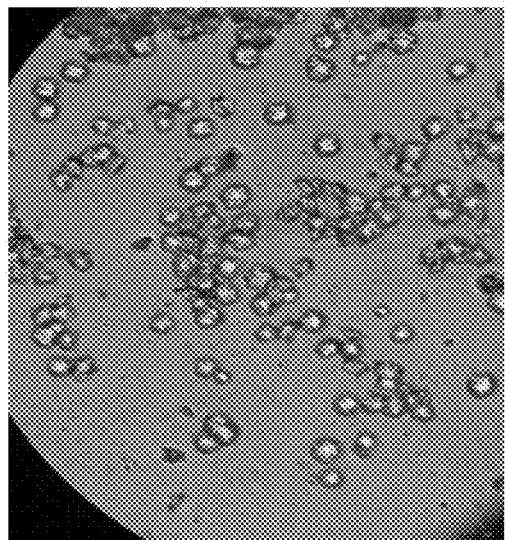
FIG. 14 is an image showing microparticles of insulin produced by a typical crystallization approach known to those of skill in the art.

Crystallization Method 5: A 500 μl aliquot of insulin (~62 mg/ml), in water was mixed with 1,000 μl of reagent containing 20% (w/v) PEG 3000, 100 mM Tris base/Hydrochloric acid pH 7.0, 200 mM Calcium acetate, and incubated at room temperature overnight. The final concentration of the insulin in solution was 15.5 mg/ml. This mixture was then mixed using a votex and left at room temperature. Insulin microparticles were obtained on the following day. (FIG. 14). 90% of the input Insulin formed microparticles by this method.

Figure 15:
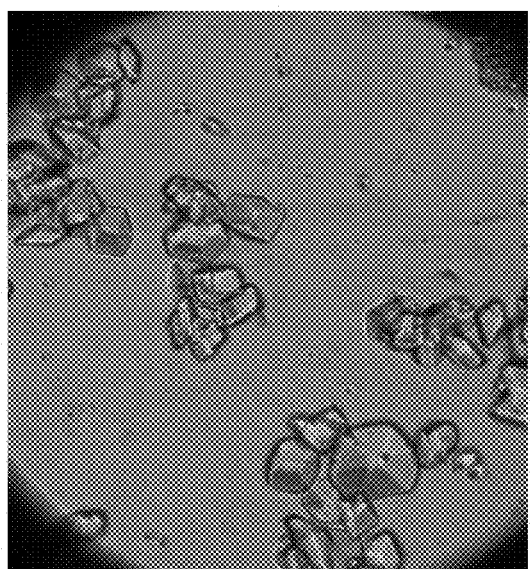
FIG. 15 is an image showing microparticles of insulin produced by a typical crystallization approach known to those of skill in the art.

Crystallization Method 6: A 500 μl aliquot of insulin (~62 mg/ml), in water was mixed with 1,000 μl of reagent containing 20% (w/v) PEG 1000, 100 mM Sodium cacodylate/Hydrochloric acid pH 6.5, 200 mM Magnesium chloride, and incubated at room temperature overnight. The final concentration of the insulin in solution was 15.5 mg/ml. This mixture was then mixed using a votex and left at room temperature. Insulin microparticles were obtained on the following day. (FIG. 15). 90% of the input Insulin formed microparticles by this method.

Figure 16:
FIG. 16 is an image showing microparticles of insulin produced by a typical crystallization approach known to those of skill in the art.

Crystallization Method 7: A 500 μl aliquot of insulin (~62 mg/ml), in water was mixed with 1,000 μl of reagent containing 10% (v/v) 2-propanol, 100 mM MES/Sodium hydroxide pH 6.0, 200 mM Calcium acetate, and incubated at room temperature overnight. The final concentration of the insulin in solution was 15.5 mg/ml. This mixture was then mixed using a votex and left at room temperature. Insulin microparticles were obtained on the following day. (FIG. 16). 90% of the input Insulin formed microparticles by this method.

Example 4

Pharmacokinetics Study of Liraglutide Formulation Containing Vitamin E in New Zealand White Rabbits The present Example demonstrates that oral formulations of liraglutide exemplary of oral formulations disclosed herein have therapeutically effective pharmacokinetic profiles, e.g., with advantageous properties as compared to parenteral administration of the same polypeptide.

The present Example includes an oral formulation of crystallized polypeptide prepared as follows: Commercially obtained Victoza®—Novo Nordisk (3 mL solution contains 6 mg/mL Liraglutide, 5.5 mg phenol, sodium hydroxide, hydrochloric acid and water for injection) was dialyzed against water for 24 hr at 4° C. with three changes. The dialyzed liraglutide was then used to prepare microparticles according to the procedure mentioned under Example 2. The microparticle liraglutide was then lyophilized after washing with cold isopropanol. The lyophilized liraglutide (dosage mentioned under Table 2) was then transferred to size 1 clear gelatin capsules containing 50 μL of Vitamin E (Sigma Chemical Company). The capsules were then stored at 4° C. until further use.

Pharmacokinetic analysis was conducted in New Zealand White male Rabbits weighing 1.5 kg for 5 days. Experimental design is shown in Table 2. Rabbits were maintained on a diet containing sodium bicarbonate (20 gms regular diet+3 gms sodium bicarbonate–pellets/diet balls were prepared by adding water). The animals were maintained on the above diet from day –3 to 0 days before dosing and followed by regular normal diet only during the experimental period. Plasma samples collected at different time points were analyzed by LRT ELISA kit according to ABBEXA protocol. This kit is based on competitive enzyme-linked immuno-sorbent assay technology. An antibody, anti-liraglutide, was pre-coated onto a 96-well plate. Standards, test samples, and biotin-conjugated reagent were added to the wells and incubated. A competitive inhibition reaction takes place between the biotin-labelled LRT and the unlabelled-LRT on the pre-coated antibody. The HRP-conjugated reagent was then added, and the whole plate was incubated. Unbound conjugates were removed using wash buffer at each stage. TMB substrate was used to quantify the HRP enzymatic reaction. After TMB substrate was added, only wells that contain sufficient LRT will produce a blue colored product, which then changes to yellow after adding the acidic stop solution. The intensity of the color yellow is inversely proportional to the LRT amount bound on the plate. The OD was measured spectrophotometrically at 450 nm in a microplate reader, from which the concentration of LRT can be calculated.

Liraglutide was analyzed in plasma using a specific enzyme-linked immunosorbent assay (ELISA). Pharmacokinetic endpoints were determined using non-compartmental methods using PK Solutions software. AUC was approximated using the trapezoidal rule on the observed concentrations. $C_{max}$ for each liraglutide dose was derived as the maximum of all valid concentrations, and $t_{max}$ was then determined as the corresponding time point to $C_{max}$. The terminal elimination rate constant $(\lambda_z)$ was estimated by log-linear regression on the terminal part of the concentration-time curve, and $t_{1/2}$ was then calculated as $t_{1/2}=\ln 2/\lambda_z$.

Figure 17:
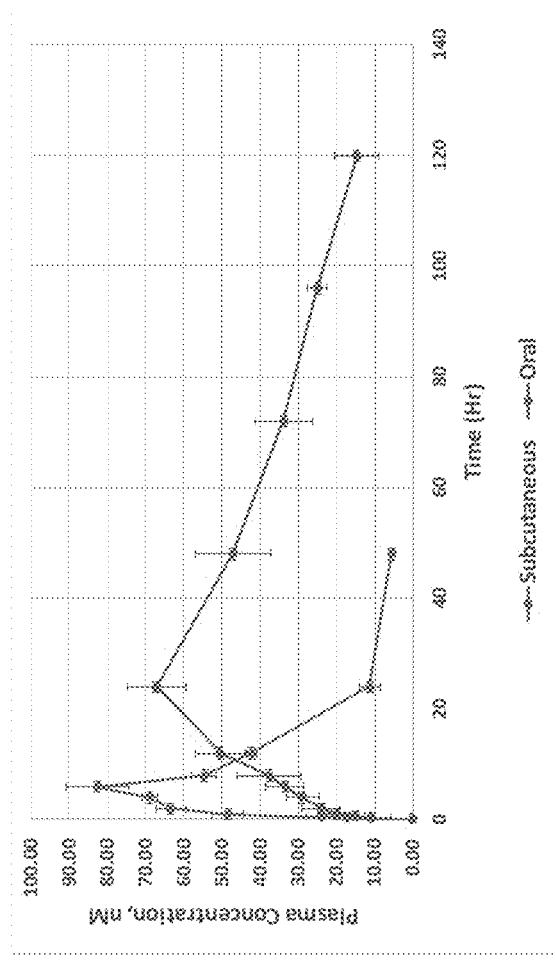
FIG. 17 is a graph showing plasma concentration of liraglutide over time following subcutaneous administration of a standard of care formulation of liraglutide or following oral administration of a formation as provided herein.

The data in Table 3 and FIG. 17 demonstrate the average plasma concentration of liraglutide at different time points. Orally administered liraglutide formulation showed 39% bioavailability when compared to SC.

TABLE 2

| Experimental Design for Pharmacokinetic Analysis | | |
| --- | --- | --- |
| | SC (Marketed Formulation) | Oral (Vitamin E Formulation) |
| No. of New Zealand White Rabbits | 3 | 3 |
| Sex | Male | Male |
| Body Weight | ~1.5 kg | ~1.5 kg |
| Group | 1 | 2 |
| Test Item | Liraglutide | Liraglutide |
| Dose (mg) (6 mg/mL solution) | 0.15 (25 μl) | 1.5 |
| Formulation | Liquid | Capsule (Lyophilized and Formulated in Vitamin E Formulation) |
| Route | SC (subcutaneous) | PO (oral) |
| Feeding status | Fed | Fed |
| Blood/Plasma Sample Collection Time | 0, 0.25, 0.5, 1, 2, 4, 6, 8, 12, 24, 48 hr post dose | 0, 0.25, 0.5, 1, 2, 4, 6, 8, 12, 24, 48, 72, 96, 120 hr post dose |
| Analysis | Liraglutide LRT ELISA Kit (ABBEXA) | |

TABLE 3

| Pharmacokinetic Properties | | |
| --- | --- | --- |
| | SC (Marketed Formulation), 0.15 mg | Oral (Vitamin E Formulation), 1.5 mg |
| $C_{max}$ (nM) | 82.6 | 67.1 |
| $T_{max}$ (hrs) | 6.00 | 24.00 |
| $AUC_{0-t}$ (nmol · hrs/mL) | 1172 | 4582 |
| $T_{1/2}$ (hr) | 11 | 45 |

Example 5

Pharmacokinetics Study of Liraglutide Formulation Containing Vitamin E in Beagle Dogs The present Example demonstrates that oral formulations of liraglutide exemplary of oral formulations disclosed herein have therapeutically effective pharmacokinetic profiles, e.g., with advantageous properties as compared to parenteral administration of the same polypeptide.

The present Example includes an oral formulation of crystallized polypeptide prepared as follows: Commercially obtained Victoza®—Novo Nordisk (3 mL solution contains 6 mg/mL Liraglutide, 5.5 mg phenol, sodium hydroxide, hydrochloric acid and water for injection) was dialyzed against water for 24 hr at 4° C. with three changes. The dialyzed liraglutide was then processed to prepare microparticles according to the procedure mentioned under Example 2 The microparticle liraglutide was then lyophilized after washing with cold isopropanol. The lyophilized liraglutide (dosage mentioned under Table 4) was then transferred to size 1 clear gelatin capsules containing 50 μL of Vitamin E (Sigma Chemical Company). The capsules were then stored at 4° C. until further use.

Pharmacokinetic analysis was conducted in Beagle dogs weighing 15 kg for 5 days. Experimental design is shown in Table 4. Plasma samples collected at different time points were analyzed by LRT ELISA kit according to ABBEXA protocol. This kit is based on competitive enzyme-linked immuno-sorbent assay technology. An antibody, anti-lira-glutide, was pre-coated onto a 96-well plate. Standards, test samples, and biotin-conjugated reagent were added to the wells and incubated. A competitive inhibition reaction takes place between the biotin-labelled LRT and the unlabelled-LRT on the pre-coated antibody. The HRP-conjugated reagent was then added, and the whole plate was incubated. Unbound conjugates were removed using wash buffer at each stage. TMB substrate was used to quantify the HRP enzymatic reaction. After TMB substrate was added, only wells that contain sufficient LRT will produce a blue colored product, which then changes to yellow after adding the acidic stop solution. The intensity of the color yellow is inversely proportional to the LRT amount bound on the plate. The OD was measured spectrophotometrically at 450 nm in a microplate reader, from which the concentration of LRT can be calculated.

Figure 18:
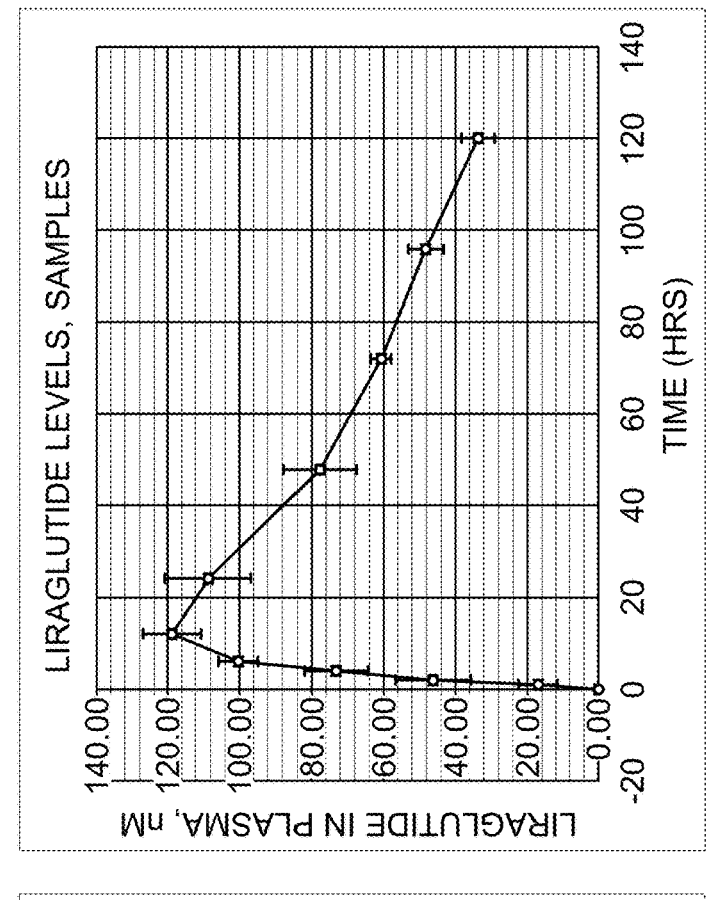
FIG. 18 is a pair of graphs showing plasma concentration of liraglutide over time following subcutaneous administration of a standard of care formulation of liraglutide or following oral administration of a formation as provided herein.
Figure 18:
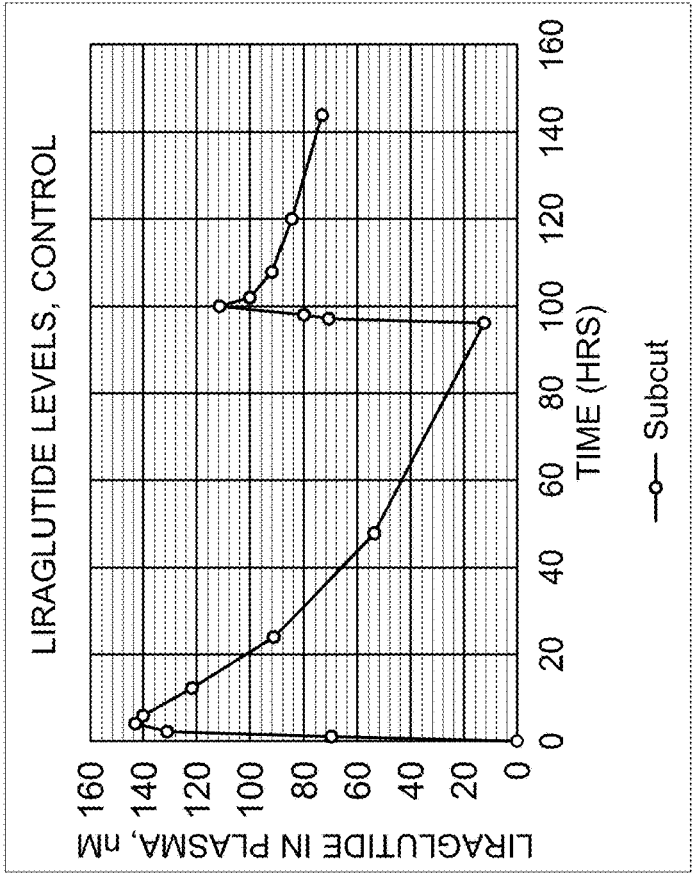

The data in Table 5 and FIG. 18 demonstrate the average Plasma concentration of liraglutide at different time points. Orally administered liraglutide formulation (15 mg in cap-sule formulation) showed 19% bioavailability when com-pared to SC controls (SC, 1.5 mg, with a second injection administered 96 hrs after the first).

Liraglutide was analyzed in plasma using a specific enzyme-linked immunosorbent assay (ELISA). Pharmaco-kinetic endpoints were determined using non-compartmen-tal methods using PK Solutions software. AUC was approxi-mated using the trapezoidal rule on the observed concentrations. $C_{max}$ for each liraglutide dose was derived as the maximum of all valid concentrations, and $t_{max}$ was then determined as the corresponding time point to $C_{max}$. The terminal elimination rate constant $(\lambda_z)$ was estimated by log-linear regression on the terminal part of the concentra-tion-time curve, and $t_{1/2}$ was then calculated as $t_{1/2}=\ln 2/\lambda_z$.

TABLE 4

Experimental Design for Pharmacokinetic Analysis

| | SC (Marketed Formulation) | Oral (Vitamin E Formulation) |
|---|---|---|
| No. of Beagle Dogs | 1 | 4 |
| Sex | Male | Male |
| Body Weight | ~15 kg | ~15 kg |
| Group | 1 | 2 |
| Period | 1　　　2 | |
| | Washout: 72 hrs between period 1 and period 2 | |
| Test Item | Liraglutide | Liraglutide |
| Dose (mg) (6 mg/mL solution) | 1.5 (250 μl) | 15 |
| Formulation | Liquid | Capsule (Lyophilized and Formulated in Vitamin E Formu-lation) |

TABLE 4-continued

Experimental Design for Pharmacokinetic Analysis

| | SC (Marketed Formulation) | Oral (Vitamin E Formulation) |
|---|---|---|
| Route | SC | PO |
| Feeding status | Fed | Fed |
| Blood/Plasma Sample Collection Time | 0, 1, 2, 4, 6, 12, 24, 48 hr post dose | 0, 1, 2, 4, 6, 12, 24, 48, 72, 96, 120 hr post dose |
| Analysis | Liraglutide LRT ELISA Kit (ABBEXA) | |

TABLE 5

Pharmacokinetic Properties

| | SC (Marketed Formulation), 1.5 mg | Oral (Vitamin E Formulation), 15 mg |
|---|---|---|
| $C_{max}$ (nM) | 143.42 | 118.96 |
| $T_{max}$ (hrs) | 4.00 | 12.00 |
| AUC0-t (nmole · hrs/L) | 4493.73 | 8557.36 |
| AUC0-∞ (nmole · hrs/L) | 6851.89 | 11406.36 |
| T½ (hr) | 30.42 | 58.79 |

Example 6

Pharmacokinetics Study of Liraglutide Formulation Containing Vitamin E in Minipigs The present Example demonstrates that oral formulations of liraglutide exemplary of oral formulations disclosed herein have therapeutically effective pharmacokinetic pro-files, e.g., with advantageous properties as compared to parenteral administration of the same polypeptide.

The present Example includes an oral formulation of crystallized polypeptide prepared as follows: Commercially obtained Victoza®—Novo Nordisk (3 mL solution contains 6 mg/mL Liraglutide, 5.5 mg phenol, sodium hydroxide, hydrochloric acid and water for injection) was dialyzed against water for 24 hr at 4° C. with three changes. The dialyzed liraglutide was then processed to prepare micropar-ticles according to the procedure mentioned under Example 2 The microparticle liraglutide was then lyophilized after washing with cold isopropanol. The lyophilized liraglutide (dosage mentioned under Table 6) was then transferred to size 1 clear gelatin capsules containing 50 μL of Vitamin E (Sigma Chemical Company). The capsules were then stored at 4° C. until further use.

Pharmacokinetic analysis was conducted in Minipigs weighing 12 kg for 5 days. Experimental design is shown in Table 6. Plasma samples collected at different time points were analyzed by LRT ELISA kit according to ABBEXA protocol. This kit is based on competitive enzyme-linked immuno-sorbent assay technology. An antibody, anti-lira-glutide, was pre-coated onto a 96-well plate. Standards, test samples, and biotin-conjugated reagent were added to the wells and incubated. A competitive inhibition reaction takes place between the biotin-labelled LRT and the unlabelled-LRT on the pre-coated antibody. The HRP-conjugated reagent was then added, and the whole plate was incubated. Unbound conjugates were removed using wash buffer at each stage. TMB substrate was used to quantify the HRP enzymatic reaction. After TMB substrate was added, only wells that contain sufficient LRT will produce a blue colored product, which then changes to yellow after adding the acidic stop solution. The intensity of the color yellow is inversely proportional to the LRT amount bound on the plate. The OD was measured spectrophotometrically at 450 nm in a microplate reader, from which the concentration of LRT can be calculated.

Figure 19:
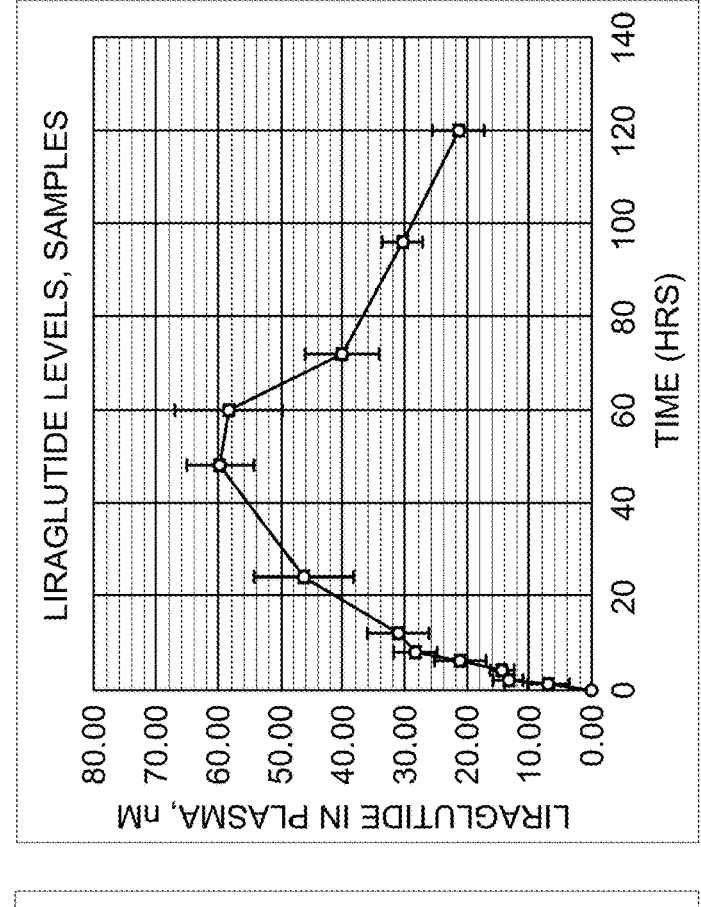
FIG. 19 is a pair of graphs showing plasma concentration of liraglutide over time following subcutaneous administration of a standard of care formulation of liraglutide or following oral administration of a formation as provided herein.
Figure 19:
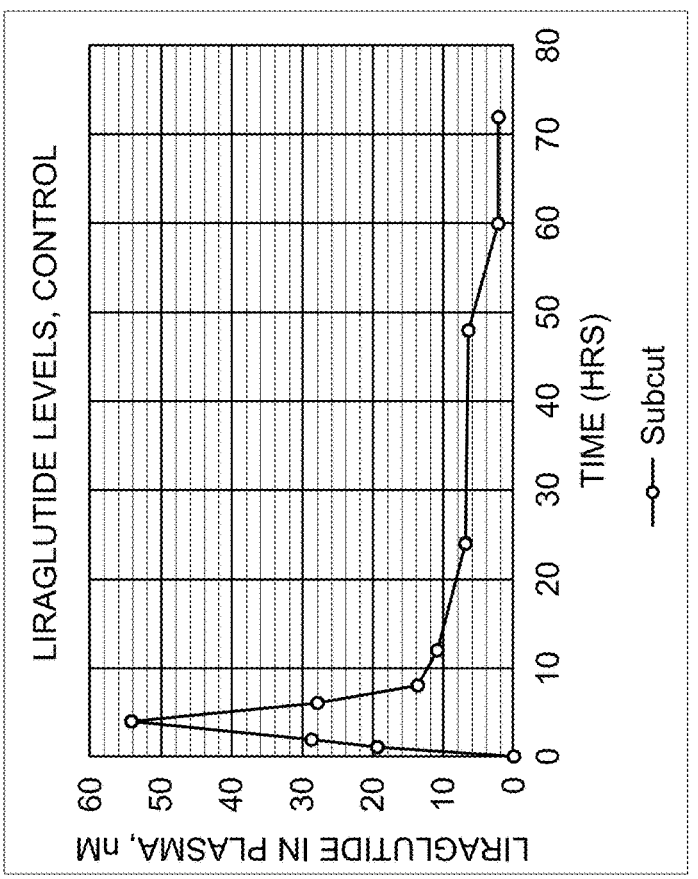

The data in Table 7 and FIG. 19 demonstrates the average Plasma concentration of Liraglutide at different time points. Orally administered liraglutide formulation (1.250 mg is in capsule formulation) showed 38% bioavailability when compared to SC (0.0625 mg).

Liraglutide was analyzed in plasma using a specific enzyme-linked immunosorbent assay (ELISA). Pharmacokinetic endpoints were determined using non-compartmental methods using PK Solutions software. AUC was approximated using the trapezoidal rule on the observed concentrations. $C_{max}$ for each liraglutide dose was derived as the maximum of all valid concentrations, and $t_{max}$ was then determined as the corresponding time point to $C_{max}$. The terminal elimination rate constant ($\lambda_z$) was estimated by log-linear regression on the terminal part of the concentration-time curve, and $t_{1/2}$ was then calculated as $t_{1/2}=\ln 2/\lambda_z$.

TABLE 6

| Experimental Design for Pharmacokinetic Analysis | | |
|---|---|---|
| | SC (Marketed Formulation) | Oral (Vitamin E Formulation) |
| No. of Beagle Dogs | 1 | 4 |
| Sex | Male | Male |
| Body Weight | ~12 kg | ~12 kg |
| Group | 1 | 2 |
| Test Item | Liraglutide | Liraglutide |
| Dose (mg) (6 mg/mL solution) | 0.0625 (10.4 µl) | 1.25 |
| Formulation | Liquid | Capsule (Lyophilized and Formulated in Vitamin E Formulation) |
| Route | SC | PO |
| Feeding status | Fed | Fed |
| Blood/Plasma Sample Collection Time | 0, 1, 2, 4, 6, 12, 24, 48, 60, 72 hr post dose | 0, 1, 2, 4, 6, 12, 24, 48, 60, 72, 96, 120 hr post dose |
| Analysis | Liraglutide LRT ELISA Kit (ABBEXA) | |

TABLE 7

| Pharmacokinetic Properties | | |
|---|---|---|
| | SC (Marketed Formulation), 0.0625 mg | Oral (Vitamin E Formulation), 1.25 mg |
| $C_{max}$ (nM) | 54.25 | 59.70 |
| $T_{max}$ (hrs) | 4.00 | 48.00 |
| AUC0-t (nmole · hrs/L) | 610.91 | 4741.98 |
| AUC0-∞ (nmole · hrs/L) | 658.76 | 6368.50 |
| T½ (hr) | 16.37 | 52.81 |

Example 7

Pharmacokinetics Study of Trastuzumab Formulation Containing Vitamin E in New Zealand White Rabbits The present Example demonstrates that oral formulations of trastuzumab exemplary of oral formulations disclosed herein have therapeutically effective pharmacokinetic profiles, e.g., with advantageous properties as compared to parenteral administration of the same polypeptide.

The present Example includes an oral formulation of crystallized polypeptide prepared as follows: Commercially obtained Trastuzumab, HERCEPTIN® (lyophilized powder contains 440 mg trastuzumab, 9.9 mg of L-Histidine.HCl, 6.4 mg of L-Histidine, 400 mg of α,α,-Trehalose dihydrate, and 1.8 mg Polysorbate 20, USP; and 20 mL of water for injection for reconstitution) was reconstituted in 6 mL of water for injection. The reconstituted trastuzumab was then processed to prepare microparticles according to the procedure mentioned under Example 1. The microparticle trastuzumab was then washed with cold isopropanol. The trastuzumab (dosage mentioned under Table 8) was then transferred to size 00 clear gelatin capsules containing 50 µL of Vitamin E (Sigma Chemical Company). The capsules were then stored at 4° C. until further use.

Pharmacokinetic analysis was conducted in New Zealand White male Rabbits weighing 1.5 kg for 14 days. Experimental design is shown in Table 8. Rabbits were maintained on a diet containing sodium bicarbonate (20 gms regular diet+3 gms sodium bicarbonate–pellets/diet balls were prepared by adding water). The animals were maintained on the above diet from day −3 to 0 days before dosing and followed by regular normal diet only during the experimental period. Plasma samples collected at different time points were analyzed by ELISA. Briefly, MAXISORP NUNC immuno plates were coated with 2 µg/mL anti-trastuzumab coating antibody (Abcam) in Sodium carbonate buffer of pH 9.6, overnight at 4° C. The coated plates were washed with washing buffer (PBS+0.01% Tween 20). Post-wash, plates were blocked with blocking buffer (PBS+1% BSA) for 3 hours at RT. Plasma samples to be analyzed were diluted in PBS and incubated with coating antibody for an hour followed by wash and addition of Goat Anti-Human IgG (Fc specific)—Peroxidase capture antibody (Sigma). Detection was done using TMB substrate at 450 nm.

Results

Figure 20:
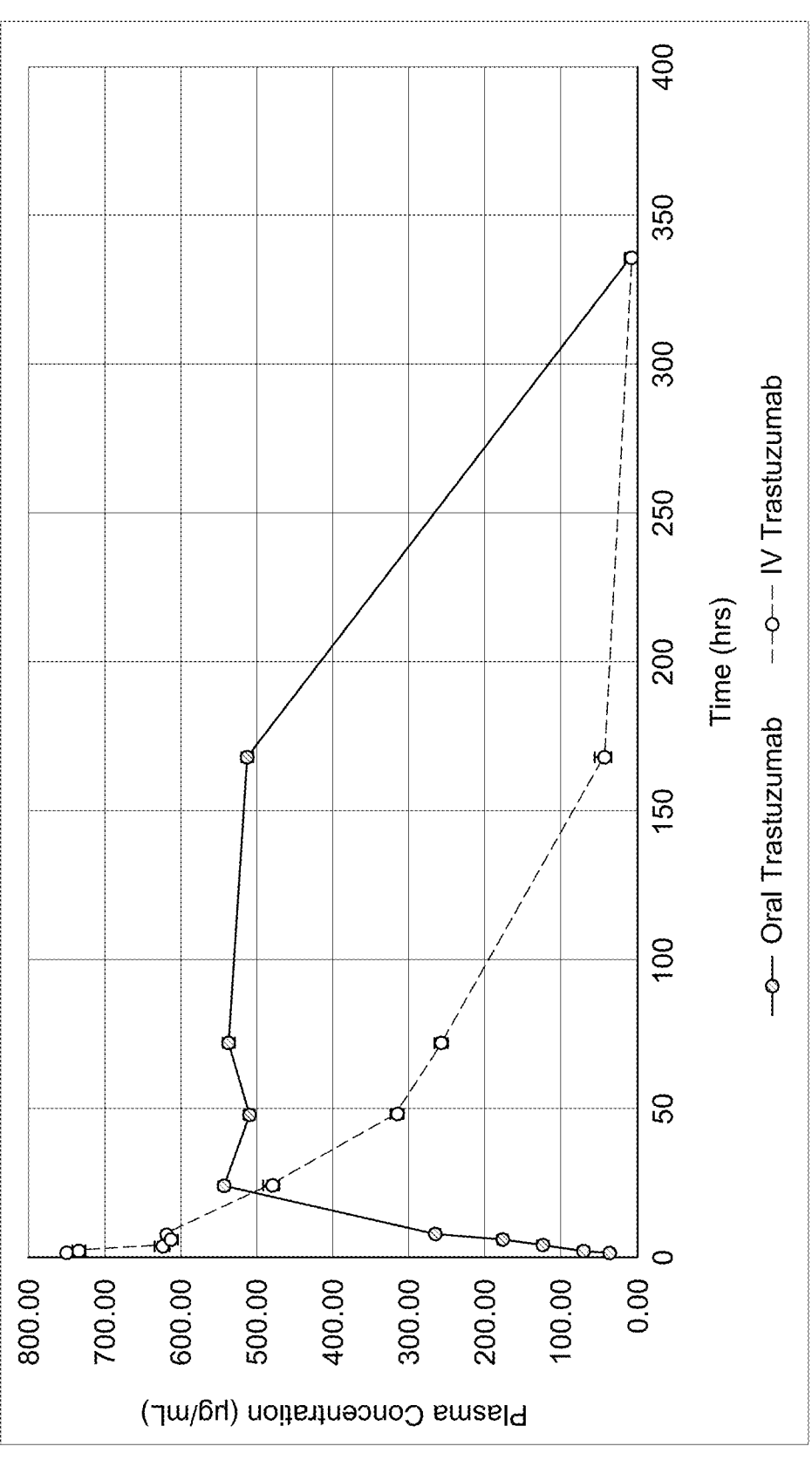
FIG. 20 is a graph showing plasma concentration of trastuzumab over time following subcutaneous administration of a standard of care formulation of trastuzumab or following oral administration of a formation as provided herein.

The data in Table 9 and FIG. 20 demonstrates the average plasma concentration of trastuzumab at different time points. Orally administered trastuzumab formulation showed 26% bioavailability when compared to IV (ReconstitutedHerclon (Roche) vial contains 21 mg/mL Trastuzumab, L-Histidibe hydrochloride, L-Histidine, -Trehalose dihydrate, Polysorbate 20 and water for injection).

Trastuzumab was analyzed in plasma using a specific enzyme-linked immunosorbent assay (ELISA). Pharmacokinetic endpoints were determined using non-compartmental methods using PK Solutions software. AUC was approximated using the trapezoidal rule on the observed concentrations. $C_{max}$ for each Trastuzumab dose was derived as the maximum of all valid concentrations, and $t_{max}$ was then determined as the corresponding time point to $C_{max}$. The terminal elimination rate constant ($\lambda_z$) was estimated by log-linear regression on the terminal part of the concentration-time curve, and $t_{1/2}$ was then calculated as $t_{1/2}=\ln 2/\lambda_z$.

TABLE 8

| Experimental Design for Pharmacokinetic Analysis | | |
|---|---|---|
| | IV (Marketed Formulation) | Oral (Vitamin E Formulation) |
| No. of New Zealand White Rabbits | 1 | 2 |
| Sex | Male | Male |
| Body Weight | ~1.5 kg | ~1.5 kg |
| Group | 1 | 2 |
| Test Item | Trastuzumab | Trastuzumab |

TABLE 8-continued

Experimental Design for Pharmacokinetic Analysis

| | IV (Marketed Formulation) | Oral (Vitamin E Formulation) |
|---|---|---|
| Dose (mg) (21 mg/mL solution) | 16 | 160 |
| Formulation | Liquid | Capsule (Lyophilized and Formulated in Vitamin E Formulation) |
| Route | IV | PO |
| Feeding status | Fed | Fed |
| Blood/Plasma Sample Collection Time | 0, 1, 2, 4, 6, 8, 24, 48, 72, 168, 336 hr post dose | 0, 1, 2, 4, 6, 8, 24, 48, 72, 168, 336 hr post dose |
| Analysis | Trastuzumab ELISA Kit (Abcam) | |

TABLE 9

Pharmacokinetic Properties

| | IV (Marketed Formulation), 16 mg | Oral (Vitamin E Formulation), 160 mg |
|---|---|---|
| $C_{max}$ (µg/mL) | 751 | 543 |
| $T_{max}$ (hrs) | 1.00 | 24.00 |
| $AUC_{0-t}$ (µg · hrs/mL) | 48528 | 126694 |

Example 8

Pharmacokinetics Study of Trastuzumab Formulation Containing Vitamin E in New Zealand White Rabbits The present Example demonstrates that oral formulations of trastuzumab exemplary of oral formulations disclosed herein have therapeutically effective pharmacokinetic profiles, e.g., with advantageous properties as compared to parenteral administration of the same polypeptide.

The present Example includes an oral formulation of crystallized polypeptide prepared as follows: Commercially obtained Trastuzumab, HERCEPTIN® (lyophilized powder contains 440 mg trastuzumab, 9.9 mg of L-Histidine.HCl, 6.4 mg of L-Histidine, 400 mg of α,α-Trehalose dihydrate, and 1.8 mg Polysorbate 20, USP; and 20 mL of water for injection for reconstitution) was reconstituted in 6 mL of water for injection. The reconstituted trastuzumab was then processed to prepare microparticles according to the procedure mentioned under Example 1. The microparticle trastuzumab was then lyophilized after washing with cold isopropanol. The lyophilized trastuzumab (dosage mentioned under Table 10) was then transferred to size 00 clear gelatin capsules containing 50 µL of Vitamin E (Sigma Chemical Company). The capsules were then stored at 4° C. until further use.

Pharmacokinetic analysis was conducted in New Zealand White male Rabbits weighing 1.5 kg for 5 days. Experimental design is shown in Table 10. Rabbits were maintained on a diet containing sodium bicarbonate (20 gms regular diet+3 gms sodium bicarbonate–pellets/diet balls were prepared by adding water). The animals were maintained on the above diet from day –3 to 0 days before dosing and followed by regular normal diet only during the experimental period. Plasma samples collected at different time points were analyzed by ELISA. Briefly, MAXISORP NUNC immuno plates were coated with 2 µg/mL anti-trastuzumab coating antibody (Abcam) in Sodium carbonate buffer of pH 9.6, overnight at 4° C. The coated plates were washed with washing buffer (PBS+0.01% Tween 20). Post-wash, plates were blocked with blocking buffer (PBS+1% BSA) for 3 hours at RT. Plasma samples to be analyzed were diluted in PBS and incubated with coating antibody for an hour followed by wash and addition of Goat Anti-Human IgG (Fc specific)—Peroxidase capture antibody (Sigma). Detection was done using TMB substrate at 450 nm.

Figure 21:
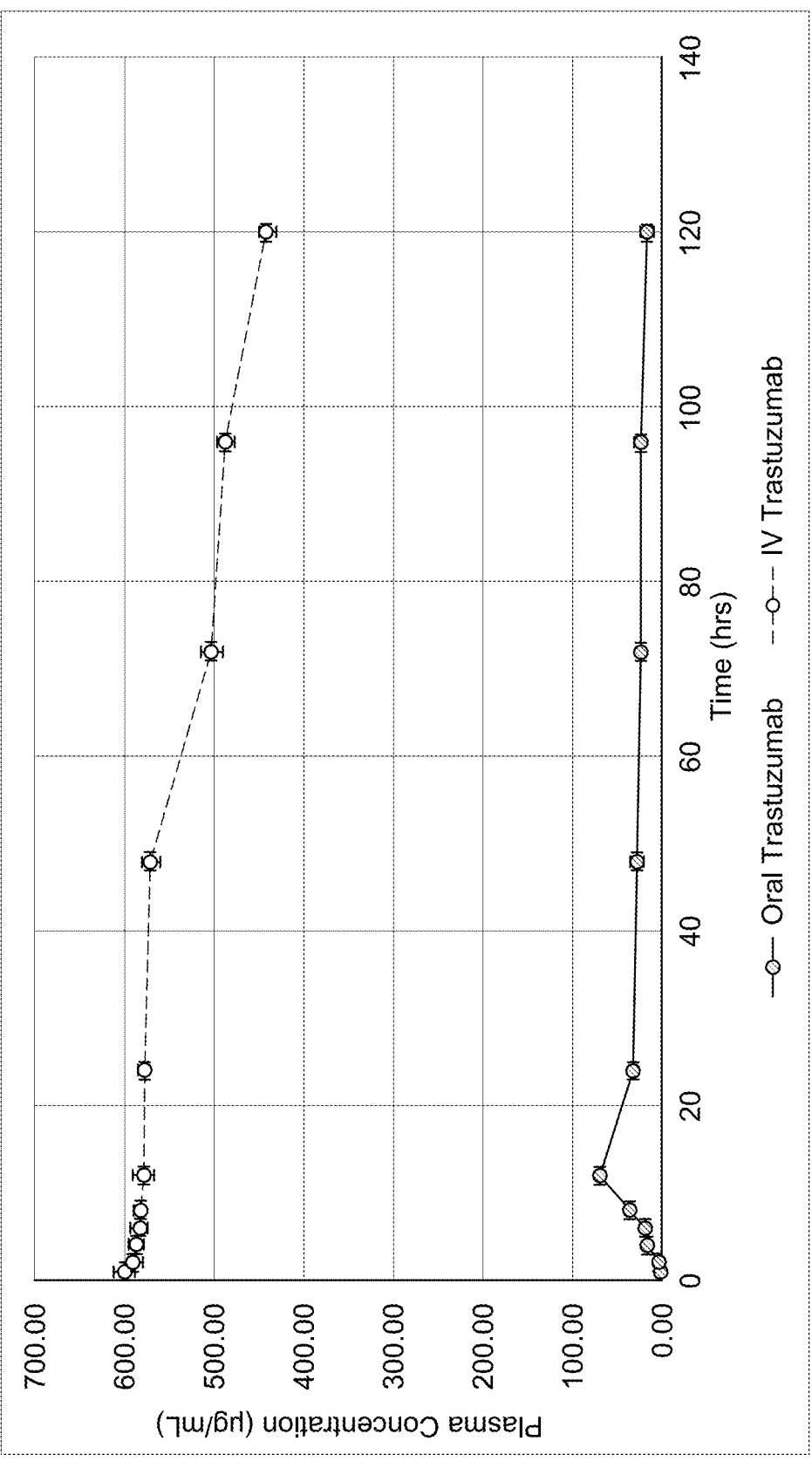
FIG. 21 is a graph showing plasma concentration of trastuzumab over time following subcutaneous administration of a standard of care formulation of trastuzumab or following oral administration of a formation as provided herein.

The data in Table 11 and FIG. 21 demonstrate the average Plasma concentration of Trastuzumab at different time points. Orally administered Trastuzumab formulation (Herclon—Roche—Reconstituted vial contains 21 mg/mL Trastuzumab, L-Histidibe hydrochloride, L-Histidine, -Trehalose dihydrate, Polysorbate 20 and water for injection) showed 2% bioavailability when compared to IV. Trastuzumab was analyzed in plasma using a specific enzyme-linked immunosorbent assay (ELISA). Pharmacokinetic endpoints were determined using non-compartmental methods using PK Solutions software. AUC was approximated using the trapezoidal rule on the observed concentrations. $C_{max}$ for each Trastuzumab dose was derived as the maximum of all valid concentrations, and $t_{max}$ was then determined as the corresponding time point to $C_{max}$. The terminal elimination rate constant ($\lambda_z$) was estimated by log-linear regression on the terminal part of the concentration-time curve, and $t_{1/2}$ was then calculated as $t_{1/2}=\ln 2/\lambda_z$.

TABLE 10

Experimental Design for Pharmacokinetic Analysis

| | IV (Marketed Formulation) | Oral (Vitamin E Formulation) |
|---|---|---|
| No. of New Zealand White Rabbits | 1 | 2 |
| Sex | Male | Male |
| Body Weight | ~1.5 kg | ~1.5 kg |
| Group | 1 | 2 |
| Test Item | Trastuzumab | Trastuzumab |
| Dose (mg) (21 mg/mL solution) | 10 | 45 |
| Formulation | Liquid | Capsule (Lyophilized and Formulated in Vitamin E Formulation) |
| Route | IV | PO |
| Feeding status | Fed | Fed |
| Blood/Plasma Sample Collection Time | 0, 1, 2, 4, 6, 8, 12, 24, 48, 72, 96, 120 hr post dose | 0, 1, 2, 4, 6, 8, 12, 24, 48, 72, 96, 120 hr post dose |
| Analysis | Trastuzumab ELISA Kit (Abcam) | |

TABLE 11

Pharmacokinetic Properties

| | IV (Marketed Formulation), 10 mg | Oral (Vitamin E Formulation), 45 mg |
|---|---|---|
| $C_{max}$ (µg/mL) | 601 | 68 |
| $T_{max}$ (hrs) | 1.00 | 12.00 |
| $AUC_{0-t}$ (µg · hrs/mL) | 77364 | 6392 |

Example 9

Pharmacokinetics Study of Insulin Formulation Containing Vitamin E in New Zealand White Rabbits The present Example demonstrates that oral formulations of insulin exemplary of oral formulations disclosed herein have therapeutically effective pharmacokinetic profiles, e.g., with advantageous properties as compared to parenteral administration of the same polypeptide. The present example demonstrates an insulin suspension formulation of vitamin E, demonstrating that enteric formulation is not required for advantageous application of formulations of the present disclosure.

The present Example includes an oral formulation of crystallized polypeptide prepared as follows: Commercially obtained Insulin regular, Humulin R (Humulin R (insulin human recombinant) U-100 is a sterile, clear, aqueous, and colorless solution that contains human insulin (rDNA origin) 100 units/mL, glycerin 16 mg/mL and meta-cresol 2.5 mg/mL, endogenous zinc (approximately 0.015 mg/100 units) and water for injection. The pH is 7.0 to 7.8. The insulin was dialyzed against water for 24 hrs against water and lyophilized. The lyophilized insulin was reconstituted in dilute acid. The reconstituted insulin was then processed to prepare microparticles according to the procedure mentioned under Example 3. The microparticle insulin was then lyophilized after washing with cold isopropanol. The lyophilized insulin (dosage mentioned under Table 12) was then suspended in 500 µL of Vitamin E (Sigma Chemical Company). The samples were then stored at 4° C. until further use.

Pharmacokinetic analysis was conducted in New Zealand White male Rabbits weighing 1.5 kg for 2 days. Experimental design is shown in Table 12. Rabbits were maintained on a diet containing sodium bicarbonate (20 gms regular diet+3 gms sodium bicarbonate–pellets/diet balls were prepared by adding water). The animals were maintained on the above diet from day −3 to 0 days before dosing and followed by regular normal diet only during the experimental period. Oral delivery of insulin was done through a G-tube which can reach up to stomach. The G-tube was then flushed with 10 mL of coconut oil to remove any sample sticking to the tube wall. Plasma samples collected at different time points were analyzed by ELISA. Briefly, MAXISORP NUNC immuno plates were coated with 2 µg/mL anti-insulin coating antibody (Crystal Chem) in Sodium carbonate buffer of pH 9.6, overnight at 4° C. The coated plates were washed with washing buffer (PBS+ 0.01% Tween 20). Post-wash, plates were blocked with blocking buffer (PBS+1% BSA) for 3 hours at RT. Plasma samples to be analyzed were diluted in PBS and incubated with coating antibody for an hour followed by wash and addition of Goat Anti-Human IgG (Fc specific)—Peroxidase capture antibody (Sigma). Detection was done using TMB substrate at 450 nm.

Figure 22:
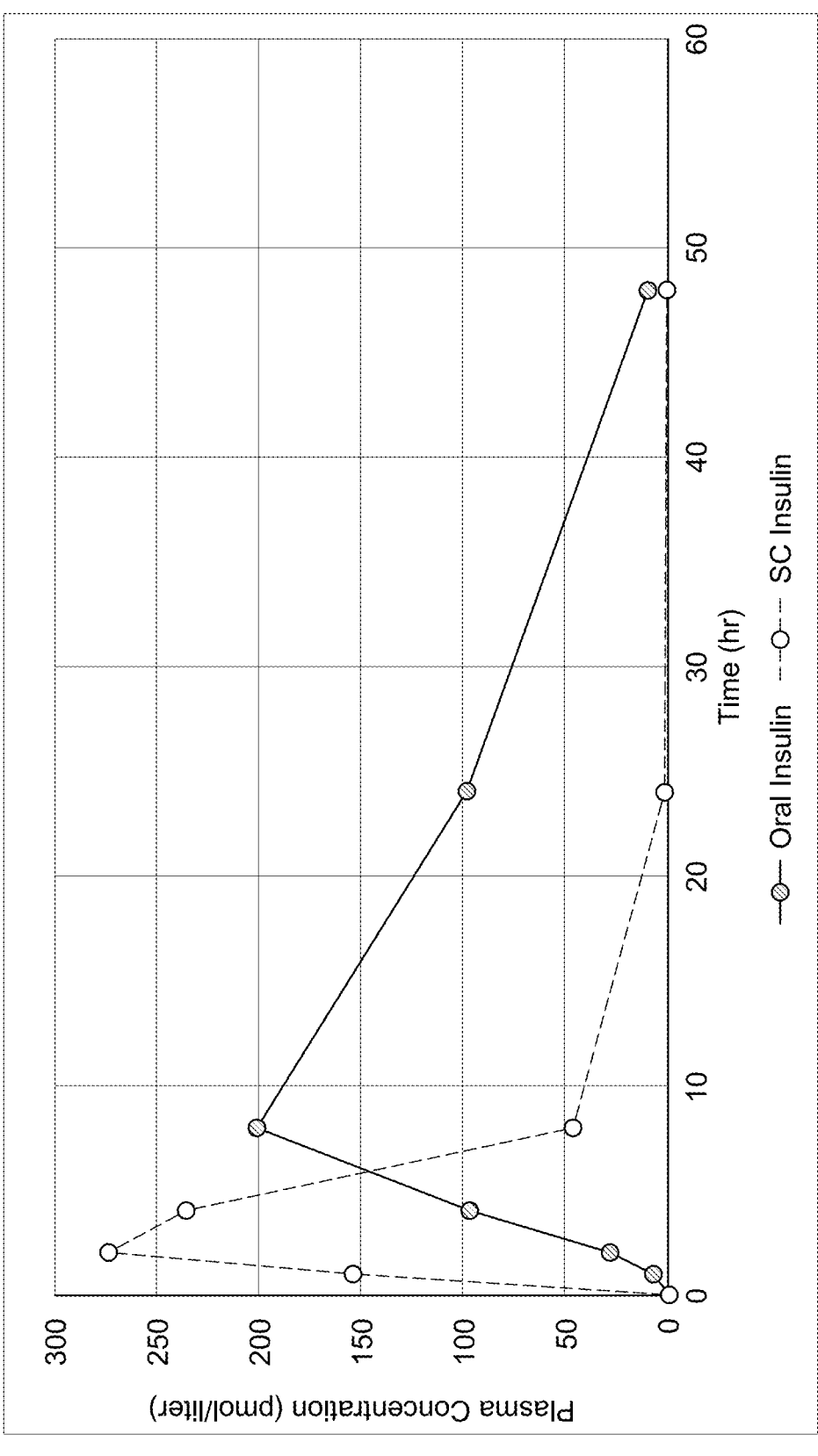
FIG. 22 is a graph showing plasma concentration of insulin over time following subcutaneous administration of a standard of care formulation of insulin or following oral administration of a formation as provided herein.

The data in Table 13 and FIG. 22 demonstrate average plasma concentration of Insulin at different time points. Orally administered Insulin formulation showed 4% bioavailability when compared to SC. Insulin was analyzed in plasma using a specific enzyme-linked immunosorbent assay (ELISA). Pharmacokinetic endpoints were determined using non-compartmental methods using PK Solutions software. AUC was approximated using the trapezoidal rule on the observed concentrations. $C_{max}$ for each Insulin dose was derived as the maximum of all valid concentrations, and $t_{max}$ was then determined as the corresponding time point to $C_{max}$. The terminal elimination rate constant ($\lambda_z$) was estimated by log-linear regression on the terminal part of the concentration-time curve, and $t_{1/2}$ was then calculated as $t_{1/2}=\ln 2/\lambda_z$.

TABLE 12

| Experimental Design for Pharmacokinetic Analysis | | |
|---|---|---|
| | SC (Marketed Formulation) | Oral (Vitamin E Formulation) |
| No. of New Zealand White Rabbits | 2 | 2 |
| Sex | Male | Male |
| Body Weight | ~1.5 kg | ~1.5 kg |
| Group | 1 | 2 |
| Test Item | Insulin | Insulin |
| Dose (mg) (3.5 mg/mL solution) | 0.3 | 3 |
| Formulation | Liquid | Suspension Formulation in Vitamin E |
| Route | SC | PO |
| Feeding status | Fed | Fed |
| Blood/Plasma Sample Collection Time | 0, 1, 2, 4, 8, 24 and 48 hr post dose | 0, 1, 2, 4, 8, 24 and 48 hr post dose |
| Analysis | Insulin ELISA Kit (Crystal Chem) | |

TABLE 13

| Pharmacokinetic Properties | | |
|---|---|---|
| | SC (Marketed Formulation), 0.3 mg | Oral (Vitamin E Formulation), 1.5 mg |
| $C_{max}$ (pmol/L) | 273.71 | 201.44 |
| $T_{max}$ (hrs) | 2.00 | 8.00 |
| $AUC_{0-t}$ (pmole · hrs/L) | 136300 | 51663 |

Example 10

Pharmacokinetics Study of Trastuzumab Formulation in New Zealand White Rabbits

The present Example demonstrates that oral formulations of trastuzumab have distinct properties for oral administration when formulated with vitamin E as compared to formulation with other similar pharmaceutically acceptable carriers. The present example demonstrates a trastuzumab suspension formulation of vitamin E, demonstrating that enteric formulation is not required for advantageous application of formulations of the present disclosure.

The present Example includes an oral formulation of crystallized polypeptide prepared as follows: Commercially obtained Trastuzumab, HERCEPTIN® (lyophilized powder contains 440 mg trastuzumab, 9.9 mg of L-Histidine.HCl, 6.4 mg of L-Histidine, 400 mg of α,α-Trehalose dihydrate, and 1.8 mg Polysorbate 20, USP; and 20 mL of water for injection for reconstitution) was reconstituted in 6 mL of water for injection. The reconstituted trastuzumab was then processed to prepare microparticles as set forth in above Examples. Microparticle trastuzumab was then washed with cold isopropanol. Samples of microparticle trastuzumab were suspended at 21 mg/mL in each of the following pharmaceutically acceptable carriers for oral formulation: Vitamin E, Coconut oil, Cod liver oil, and Ghee.

Pharmacokinetic analysis was conducted in New Zealand White male Rabbits weighing 1.5 kg for 14 days. Experimental design is shown in Table 14. Each oral formulation was orally administered as shown in Table 14. A control standard-of-care formulation (which included no microparticles or suspension) was also administered by subcutaneous injection as shown in Table 14 (Reconstituted Herclon (Roche) vial contains 21 mg/mL Trastuzumab, L-Histidibe hydrochloride, L-Histidine, α,α-Trehalose dihydrate, Polysorbate 20 and water for injection). Rabbits were maintained on a diet containing sodium bicarbonate (20 gm regular diet+3 gm sodium bicarbonate–pellets/diet balls were prepared by adding water). The animals were maintained on the above diet from day –3 to 0 days before dosing and followed by regular normal diet only during the experimental period. Oral dosing of animals was carried out using a G tube. The suspended formulations were passed through the G tube using a syringe. Administration was followed by washing of the tube with 5 mL of coconut oil and then with 5 mL of water.

Plasma samples collected at different time points were analyzed by ELISA. Briefly, MAXISORP NUNC immuno plates were coated with 2 µg/mL anti-trastuzumab coating antibody (Abcam) in Sodium carbonate buffer of pH 9.6, overnight at 4° C. The coated plates were washed with washing buffer (PBS+0.01% Tween 20). Post-wash, plates were blocked with blocking buffer (PBS+1% BSA) for 3 hours at RT. Plasma samples to be analyzed were diluted in PBS and incubated with coating antibody for an hour followed by wash and addition of Goat Anti-Human IgG (Fc specific)—Peroxidase capture antibody (Sigma). Detection was done using TMB substrate at 450 nm.

TABLE 14

| Experimental Design for Pharmacokinetic Analysis | | |
|---|---|---|
| | SC (Marketed Formulation) | Oral (Vitamin E or Coconut Oil or Cod Liver Oil or Ghee Formulation) |
| No. of New Zealand White Rabbits | 1 | 1 |
| Sex | Male | Male |
| Body Weight | ~1.5 kg | ~1.5 kg |
| Group | 1 | 2 |
| Test Item | Trastuzumab | Trastuzumab |
| Dose (mg) (21 mg/mL solution) | 8 mg/kg | 8 mg/kg |
| Formulation | Liquid | Suspension Formulation |
| Route | SC | PO |
| Feeding status | Fed | Fed |
| Blood/Plasma Sample Collection Time | 0, 1, 2, 4, 6, 8, 24, 168, 336 hr post dose | 0, 1, 2, 4, 6, 8, 24, 168, 336 hr post dose |
| Analysis | Trastuzumab ELISA Kit (Abcam) | |

Results

Figure 23:
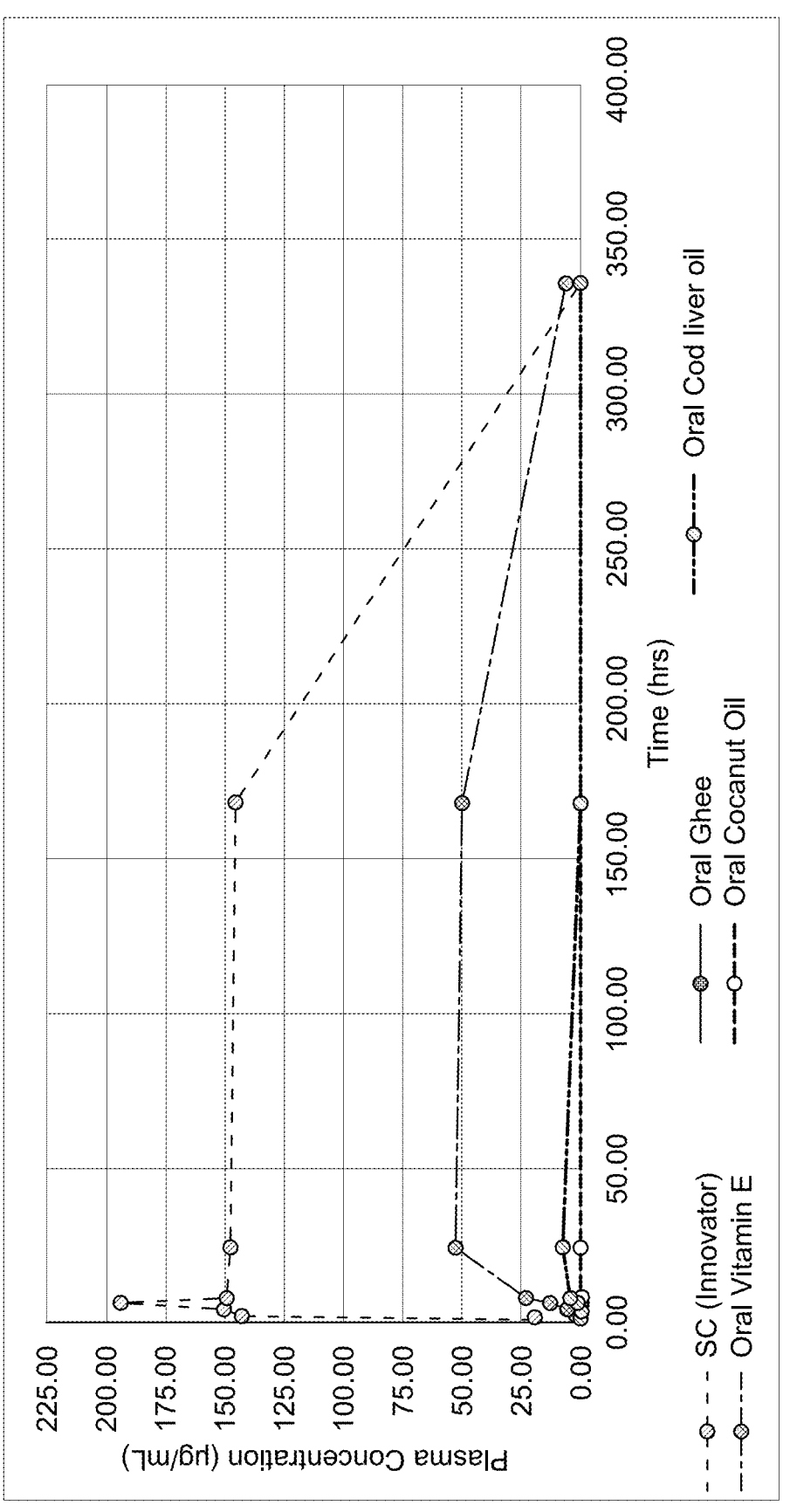
FIG. 23 is a graph showing plasma concentration of trastuzumab over time following subcutaneous administration of a standard of care formulation of trastuzumab or following oral administration of formulations including vitamin E, coconut oil, cod liver oil, or ghee.

The data in FIG. 23 demonstrates the average plasma concentration of trastuzumab at different time points. None of coconut oil, ghee, or cod liver oil demonstrated significant plasma concentration above zero at any time point, while commercial "innovator" formulation administered subcutaneously and oral vitamin E formulation both produced substantial plasma concentrations (e.g., about 50 µg/mL at 100 hours for vitamin E oral formulation and about 150 µg/mL at 100 hours for commercial "innovator" formulation administered subcutaneously). These data surprisingly and unexpectedly demonstrate that administration of a vitamin E oral formulation of the present disclosure, unlike various other similar formulations, is therapeutically and commercially viable.

Example 11

Pharmacokinetics Study of Liraglutide Formulation (Amorphous) Containing Vitamin E in New Zealand White Rabbits The present Example demonstrates that oral formulations that include amorphous liraglutide and are exemplary of oral formulations of the present disclosure have therapeutically effective pharmacokinetic profiles, e.g., with advantageous properties as compared to parenteral administration of the same polypeptide.

The present Example includes an oral formulation of amorphous liraglutide prepared as follows: Commercially available lyophilized drug substance, liraglutide, which is in the amorphous form, was powdered and passed through 25 micron sieve to obtain particle sizes which is less than 25 microns. The lyophilized liraglutide (dosage mentioned under Table 15) was then transferred to size 00 enteric coated capsules containing 100 µL of Vitamin E (Sigma Chemical Company) and 50 µL of wheat germ oil. The capsules were then stored at 4° C. until further use.

Pharmacokinetic analysis was conducted in New Zealand White male Rabbits weighing 1.5 kg for 5 days. Experimental design is shown in Table 15. Rabbits were maintained on a normal diet. Plasma samples collected at different time points were analyzed by liraglutide (LRT) ELISA kit according to ABBEXA protocol. This kit is based on competitive enzyme-linked immuno-sorbent assay technology. An antibody, anti-liraglutide, was pre-coated onto a 96-well plate. Standards, test samples, and biotin-conjugated reagent were added to the wells and incubated. A competitive inhibition reaction takes place between the biotin-labelled LRT and the unlabelled-LRT on the pre-coated antibody. The HRP-conjugated reagent was then added, and the whole plate was incubated. Unbound conjugates were removed using wash buffer at each stage. TMB substrate was used to quantify the HRP enzymatic reaction. After TMB substrate was added, only wells that contain sufficient LRT will produce a blue colored product, which then changes to yellow after adding the acidic stop solution. The intensity of the color yellow is inversely proportional to the LRT amount bound on the plate. The OD was measured spectrophotometrically at 450 nm in a microplate reader, from which the concentration of LRT can be calculated.

TABLE 15

| Experimental Design for Pharmacokinetic Analysis | | | |
|---|---|---|---|
| | IV (Marketed Formulation) | SC (Marketed Formulation) | Oral (Vitamin E Formulation) |
| No. of New Zealand White Rabbits | 8 | 8 | 8 |
| Sex | Male | Male | Male |
| Body Weight | ~1.5 kg | ~1.5 kg | ~1.5 kg |
| Group | 1 | 2 | 3 |
| Test Item | Liraglutide | Liraglutide | Liraglutide |
| Dose (mg) (6 mg/mL solution) | 0.15 (25 µl) | 0.15 (25 µl) | 1.5 |
| Formulation | Liquid | Liquid | Capsule (Lyophilized and Formulated in Vitamin E Formulation) |

TABLE 15-continued

Experimental Design for Pharmacokinetic Analysis

| | IV (Marketed Formulation) | SC (Marketed Formulation) | Oral (Vitamin E Formulation) |
|---|---|---|---|
| Route | IV (intravenous) | SC (subcutaneous) | PO (oral) |
| Feeding status | Fed | Fed | Fed |
| Blood/Plasma Sample | 0, 0.25, 0.5, | 0, 0.25, 0.5, | 0, 0.25, 0.5, |
| Collection Time | 1, 2, 6, 12, | 1, 2, 6, 12, | 1, 2, 6, 12, 24, |
| | 24, 48, 72, 96, | 24, 48, 72, 96, | 48, 72, 96, 120 |
| | 120 post dose | 120 post dose | hr post dose |
| Analysis | Liraglutide LRT ELISA Kit (ABBEXA) | | |

The liraglutide ELISA protocol of the present Example is set forth below. Reagents as follows were brought to room temperature prior to use: (1) Detection Reagent A and B: Detection Reagent A and B was diluted to a ratio of 1:100 using Assay Diluent A and B respectively; (2) Wash Buffer (30×): Dilution: To make wash buffer (1×), add 20 ml of wash buffer (30×) to 580 ml of DI water. This is the working solution; (3) Standard Liraglutide (1 ml): Standard vial was briefly centrifuged and 1 ml of sample diluent was added to the vial to obtain 1000 pg/ml and further serially diluted to obtain 333.33 pg/ml, 111.1 pg/ml, 37.03 pg/ml, 12.34 pg/ml; and (4) TMB Substrate Solution. Once thawed, reagent was aliquoted appropriately and not freeze-thawed for more than 2 times. All reagents were diluted immediately before use. Where applicable for low volumes, vials were quick spun down for its settlements at the bottom of the vial provided, before dilution. ELISA was carried out according to the following steps: (1) To each predesignated wells, 50 μl of Standard, Blank, or Sample was added; (2) Immediately, 50 μl of Detection Reagent A working solution was added to each well and covered with a plate sealer. Plate was gently agitated to ensure thorough mixing, and incubated for 1 hour at 37° C.; (3) Liquid from each well was aspirated and washed 3 times by adding approximately 350 μl of Wash Buffer using multi-channel pipette; (4) Each wash was allowed to sit for 1-2 minutes before completely aspirating; (5) After the last wash, any remaining Wash Buffer was aspirated then plates were blotted on to the clean absorbent paper; (6) To all the wells, 100 μl of Detection Reagent B working solution was added and gently agitated to ensure thorough mixing, and plate was covered with a new plate sealer and incubated for 30 minutes at 37° C.; (7) Liquid from each well was aspirated and washed 3 times by adding approximately 350 μl of Wash Buffer using multi-channel pipette; (8) 90 μl of TMB Substrate solution to each well was added and plate was incubated at 37° C. for 10-20 mins in dark; (9) Post incubation, 50 μl of Stop Solution to each well was added in the same order and timing as the TMB Substrate solution and plate was gently agitated; (10) Optical density (OD value) of each well immediately read using a microplate reader set to 450 nm. Results are provided in Tables 16-27.

TABLE 16

Pharmacokinetics of Oral Liraglutide Formulation in New Zealand White Rabbits

| Time | Abs (450 nm) | B/Bo | logit B/Bo | Conc. ng/ml | Mean Conc. ng/ml |
|---|---|---|---|---|---|
| 0 min | 0.9893 | 0.631 | 0.538 | 147.08 | 285.53 |
| | 0.7612 | 0.486 | −0.057 | 368.41 | |
| | 0.8864 | 0.566 | 0.265 | 224.42 | |
| | 0.7931 | 0.506 | 0.025 | 324.89 | |
| | 0.7578 | 0.484 | −0.065 | 373.39 | |

TABLE 16-continued

Pharmacokinetics of Oral Liraglutide Formulation in New Zealand White Rabbits

| Time | Abs (450 nm) | B/Bo | logit B/Bo | Conc. ng/ml | Mean Conc. ng/ml |
|---|---|---|---|---|---|
| | 0.8058 | 0.514 | 0.057 | 309.03 | |
| | 0.7595 | 0.485 | −0.061 | 370.89 | |
| | 0.9602 | 0.613 | 0.459 | 166.15 | |
| 15 mins | 0.62 | 0.396 | −0.424 | 649.05 | 416.89 |
| | 0.754 | 0.481 | −0.074 | 378.58 | |
| | 0.67 | 0.427 | −0.292 | 530 | |
| | 0.809 | 0.516 | 0.064 | 305.64 | |
| | 0.794 | 0.507 | 0.027 | 323.74 | |
| | 0.733 | 0.468 | −0.128 | 411.65 | |
| | 0.706 | 0.45 | −0.199 | 458.91 | |
| 30 mins | 0.833 | 0.532 | 0.127 | 277.56 | 514.52 |
| | 0.631 | 0.403 | −0.393 | 619.62 | |
| | 0.788 | 0.503 | 0.012 | 331.36 | |
| | 0.8 | 0.511 | 0.044 | 315.68 | |
| | 0.625 | 0.399 | −0.41 | 636.1 | |
| | 0.626 | 0.4 | −0.406 | 632.19 | |
| | 0.644 | 0.411 | −0.359 | 587.84 | |
| | 0.591 | 0.377 | −0.501 | 730.94 | |
| | 0.847 | 0.541 | 0.163 | 262.48 | |
| 1 hr | 0.426 | 0.272 | −0.986 | 1546.73 | 762.78 |
| | 0.66 | 0.421 | −0.318 | 551.59 | |
| | 0.674 | 0.43 | −0.28 | 520.29 | |
| | 0.572 | 0.365 | −0.552 | 791.62 | |
| | 0.557 | 0.356 | −0.594 | 844.73 | |
| | 0.723 | 0.461 | −0.154 | 428.45 | |
| | 0.517 | 0.33 | −0.708 | 1006.21 | |
| | 0.733 | 0.468 | −0.13 | 412.63 | |
| 2 hr | 0.52 | 0.332 | −0.698 | 992 | 937.54 |
| | 0.472 | 0.301 | −0.842 | 1237.79 | |
| | 0.615 | 0.393 | −0.436 | 661.21 | |
| | 0.385 | 0.245 | −1.123 | 1909.69 | |
| | 0.618 | 0.394 | −0.429 | 654.69 | |
| | 0.522 | 0.333 | −0.695 | 987.16 | |
| | 0.577 | 0.369 | −0.538 | 775.01 | |
| | 0.828 | 0.529 | 0.115 | 282.76 | |
| 6 hr | 0.309 | 0.197 | −1.405 | 2953.08 | 2461.91 |
| | 0.419 | 0.268 | −1.007 | 1597.86 | |
| | 0.38 | 0.242 | −1.14 | 1961.38 | |
| | 0.371 | 0.237 | −1.169 | 2051.39 | |
| | 0.228 | 0.145 | −1.771 | 5193.42 | |
| | 0.368 | 0.235 | −1.182 | 2091.01 | |
| | 0.378 | 0.241 | −1.146 | 1980.45 | |
| | 0.389 | 0.248 | −1.108 | 1866.68 | |
| 12 hrs | 0.197 | 0.126 | −1.941 | 6748.72 | 3641.79 |
| | 0.38 | 0.243 | −1.137 | 1952.99 | |
| | 0.312 | 0.199 | −1.392 | 2891.47 | |
| | 0.228 | 0.146 | −1.769 | 5172.89 | |
| | 0.335 | 0.214 | −1.302 | 2516.48 | |
| | 0.339 | 0.216 | −1.287 | 2458.45 | |
| | 0.303 | 0.193 | −1.428 | 3056.69 | |
| | 0.252 | 0.161 | −1.654 | 4336.61 | |
| 24 hrs | 0.253 | 0.161 | −1.647 | 4289.43 | 4349.39 |
| | 0.275 | 0.175 | −1.549 | 3684.52 | |
| | 0.298 | 0.19 | −1.45 | 3165.45 | |
| | 0.223 | 0.142 | −1.798 | 5414.11 | |
| | 0.304 | 0.194 | −1.422 | 3031.75 | |
| | 0.144 | 0.092 | −2.293 | 11616.45 | |
| | 0.379 | 0.242 | −1.143 | 1968.77 | |
| | 0.416 | 0.265 | −1.018 | 1624.65 | |
| 48 hr | 0.431 | 0.275 | −0.97 | 1507.36 | 1148.89 |
| | 0.469 | 0.299 | −0.852 | 1256.51 | |
| | 0.517 | 0.33 | −0.71 | 1009.36 | |
| | 0.494 | 0.315 | −0.775 | 1117.13 | |
| | 0.508 | 0.324 | −0.735 | 1049.92 | |
| | 0.46 | 0.294 | −0.878 | 1307.98 | |
| | 0.546 | 0.348 | −0.626 | 887.75 | |
| | 0.507 | 0.323 | −0.738 | 1055.13 | |
| 72 hrs | 0.559 | 0.357 | −0.59 | 838.59 | 1121.81 |
| | 0.481 | 0.307 | −0.814 | 1185.9 | |
| | 0.512 | 0.327 | −0.723 | 1030.31 | |
| | 0.625 | 0.399 | −0.409 | 634.79 | |
| | 0.595 | 0.38 | −0.491 | 720.3 | |
| | 0.565 | 0.361 | −0.572 | 815.92 | |

US 12,636,257 B2

61

62

TABLE 16-continued

Pharmacokinetics of Oral Liraglutide Formulation
in New Zealand White Rabbits

| Time | Abs (450 nm) | B/Bo | logit B/Bo | Conc. ng/ml | Mean Conc. ng/ml |
|---|---|---|---|---|---|
| | 0.486 | 0.31 | −0.801 | 1161.52 | |
| | 0.33 | 0.211 | −1.32 | 2587.1 | |
| 96 hr | 0.5103 | 0.326 | −0.728 | 1037.73 | 1068.02 |
| | 0.5681 | 0.363 | −0.564 | 806.23 | |
| | 0.5362 | 0.342 | −0.653 | 925.27 | |
| | 0.5757 | 0.367 | −0.543 | 780.61 | |
| | 0.4916 | 0.314 | −0.783 | 1129.44 | |
| | 0.4857 | 0.31 | −0.8 | 1160.45 | |
| | 0.4106 | 0.262 | −1.035 | 1668.08 | |
| | 0.5106 | 0.326 | −0.727 | 1036.33 | |
| 120 hr | 0.366 | 0.234 | −1.187 | 2108.3 | 1028.16 |
| | 0.628 | 0.401 | −0.402 | 628.05 | |
| | 0.553 | 0.353 | −0.607 | 862.01 | |
| | 0.513 | 0.328 | −0.719 | 1024.8 | |
| | 0.474 | 0.303 | −0.834 | 1223.42 | |
| | 0.459 | 0.293 | −0.882 | 1316.09 | |
| | 0.749 | 0.478 | −0.089 | 387.04 | |
| | 0.61 | 0.389 | −0.449 | 675.58 | |

TABLE 17

Pharmacokinetics of Oral Liraglutide Formulation
in New Zealand White Rabbits

| | Liraglutide (Conc. ng/ml) | |
|---|---|---|
| Time (Hrs) | Mean | ±SEM |
| 0 | 285.533 | 33.040 |
| 0.25 | 416.891 | 44.405 |
| 0.5 | 514.525 | 63.877 |
| 1 | 762.781 | 134.906 |
| 2 | 937.540 | 171.764 |
| 6 | 2461.909 | 413.861 |
| 12 | 3641.788 | 581.010 |
| 24 | 4349.392 | 1122.965 |
| 48 | 1148.890 | 69.777 |
| 72 | 1121.805 | 220.928 |
| 96 | 1068.017 | 98.726 |
| 120 | 1028.160 | 189.491 |

TABLE 18

Summary Table of Pharmacokinetics of Oral Liraglutide
Formulation in New Zealand White Rabbits

| Time | Conc | ln(C) | AUC | AUMC | R | R_adj |
|---|---|---|---|---|---|---|
| 0 | 285.533 | 5.65435761 | 0 | 0 | | |
| 0.25 | 416.891 | 6.0328248 | 87.803 | 13.0278438 | | |
| 0.5 | 514.525 | 6.24324414 | 204.23 | 58.2135 | | |
| 1 | 762.781 | 6.63697097 | 523.5565 | 313.224375 | | |
| 2 | 937.54 | 6.84325942 | 1373.717 | 1632.15488 | | |
| 6 | 2461.909 | 7.80869234 | 8172.615 | 34925.2229 | | |
| 12 | 3641.788 | 8.20023005 | 26483.706 | 210343.953 | | |
| 24 | 4349.392 | 8.37779134 | 74430.786 | 1098865.14 | −0.7541283 | 0.42494599 |
| 48 | 1148.89 | 7.04655154 | 140410.17 | 3013250.67 | −0.9921251 | 0.97646838 |
| 72 | 1121.805 | 7.02269427 | 167658.51 | 4644250.83 | −0.9973071 | 0.98924303 |
| 96 | 1068.017 | 6.97355894 | 193936.374 | 6843845.94 | | |
| 120 | 1028.16 | 6.93552608 | 219090.498 | 9554751.92 | | |

Figure 24:
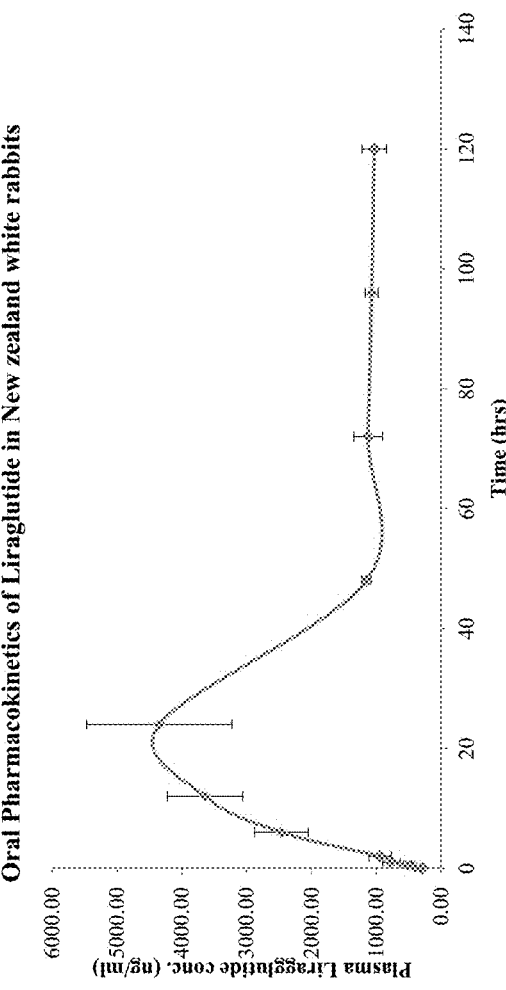
FIG. 24 is a graph showing plasma concentration of liraglutide following administration of an oral liraglutide formulation to New Zealand White Rabbits.

Concentration of liraglutide following administration of the oral formulation to New Zealand White Rabbits is graphed in FIG. 24.

TABLE 19

Pharmacokinetics of Oral Liraglutide Formulation
in New Zealand White Rabbits

| Parameter | Unit | Value |
|---|---|---|
| R | | −0.997307131 |
| R_adjusted | | 0.989243025 |
| NumRegPoints | | 3 |
| TimeRegStart | h | 72 |
| TimeRegEnd | h | 120 |
| Lambda_z | 1/h | 0.001816004 |
| t½ | h | 381.6881079 |
| Tmax | h | 24 |
| Cmax | ng/ml | 4349.392 |
| C0 | ng/ml | 416.891 |
| Tlast | h | 120 |
| Clast_obs | ng/ml | 1028.16 |
| Clast_obs/Cmax | | 0.236391661 |
| AUC 0-t | ng/ml*h | 219106.9178 |
| AUC t-inf_obs | ng/ml*h | 566166.1132 |
| AUC 0-inf_obs | ng/ml*h | 785273.0309 |
| AUC 0-t/0-inf_obs | | 0.279020047 |
| AUC 0-inf/D_obs | ng/ml*h/(µg) | 7852.730309 |
| AUMC 0-t | ng/ml*h^2 | 9554751.921 |
| AUMC t-inf_obs | ng/ml*h^2 | 379704705.3 |
| AUMC 0-inf_obs | ng/ml*h^2 | 389259457.2 |
| AUMC 0-t/0-inf_obs | | 0.024545972 |
| MRT 0-t | h | 43.60771453 |
| MRT 0-inf_obs | h | 495.6995107 |
| Vz_obs | (µg)/(ng/ml) | 0.070123323 |
| Cl_obs | (µg)/(ng/ml)/h | 0.000127344 |
| Vss_obs | (µg)/(ng/ml) | 0.063124479 |
| Clast_pred | ng/ml | 1026.259239 |
| Clast_pred/Cmax | | 0.235954644 |
| AUC t-inf_pred | ng/ml*h | 565119.4409 |
| AUC 0-inf_pred | ng/ml*h | 784226.3586 |
| AUC 0-t/0-inf_pred | | 0.279392442 |
| AUC 0-inf/D_pred | ng/ml*h/(µg) | 7842.263586 |
| AUMC t-inf_pred | ng/ml*h^2 | 379002744.6 |
| AUMC 0-inf_pred | ng/ml*h^2 | 388557496.5 |
| AUMC 0-t/0-inf_pred | | 0.024590317 |
| MRT 0-inf_pred | h | 495.4659993 |
| Vz_pred | (µg)/(ng/ml) | 0.070216913 |
| Cl_pred | (µg)/(ng/ml)/h | 0.000127514 |
| Vss_pred | (µg)/(ng/ml) | 0.063178953 |

TABLE 20

Pharmacokinetics of Intravenous (IV) Liraglutide
Formulation in New Zealand White Rabbits

| Time | Abs (450 nm) | B/Bo | logit B/Bo | Conc. ng/ml | Mean Conc. ng/ml |
|---|---|---|---|---|---|
| 0 | 0.338 | 0.216 | −1.290 | 2472.78 | 2730.55 |
| | 0.307 | 0.196 | −1.413 | 2988.31 | |
| 0.25 | 0.397 | 0.253 | −1.081 | 1789.08 | 2230.36 |
| | 0.325 | 0.207 | −1.340 | 2671.65 | |
| 0.5 | 0.394 | 0.251 | −1.092 | 1822.07 | 2196.20 |
| | 0.332 | 0.212 | −1.315 | 2570.33 | |
| 1 | 0.399 | 0.254 | −1.076 | 1775.17 | 2157.70 |
| | 0.334 | 0.213 | −1.308 | 2540.22 | |
| 2 | 0.397 | 0.253 | −1.082 | 1791.87 | 2063.13 |
| | 0.348 | 0.222 | −1.253 | 2334.39 | |
| 6 | 0.409 | 0.261 | −1.041 | 1684.32 | 1974.81 |
| | 0.353 | 0.226 | −1.233 | 2265.30 | |
| 12 | 0.479 | 0.306 | −0.819 | 1194.73 | 1550.18 |
| | 0.385 | 0.246 | −1.121 | 1905.64 | |
| 24 | 0.509 | 0.325 | −0.732 | 1045.21 | 1177.53 |
| | 0.460 | 0.293 | −0.879 | 1309.85 | |
| 48 | 0.603 | 0.385 | −0.468 | 694.92 | 717.41 |
| | 0.588 | 0.376 | −0.508 | 739.89 | |
| 72 | 0.695 | 0.444 | −0.226 | 478.26 | 599.66 |
| | 0.595 | 0.379 | −0.492 | 721.06 | |
| 96 | 1.192 | 0.761 | 1.156 | 56.75 | 105.47 |
| | 0.978 | 0.624 | 0.508 | 154.19 | |
| 120 | 1.292 | 0.824 | 1.546 | 31.06 | 65.30 |
| | 1.078 | 0.688 | 0.791 | 99.54 | |

TABLE 21

Pharmacokinetics of Intravenous (IV) Liraglutide
Formulation in New Zealand White Rabbits

| | Liraglutide (Conc. ng/ml) | |
|---|---|---|
| Time (Hrs) | Mean | ±SEM |
| 0 | 2730.55 | 257.76 |
| 0.25 | 2230.36 | 441.29 |
| 0.5 | 2196.20 | 374.13 |
| 1 | 2157.70 | 382.52 |
| 2 | 2063.13 | 271.26 |
| 6 | 1974.81 | 290.49 |
| 12 | 1550.18 | 355.45 |
| 24 | 1177.53 | 132.32 |
| 48 | 717.41 | 22.48 |
| 72 | 599.66 | 121.40 |
| 96 | 105.47 | 48.72 |
| 120 | 65.30 | 34.24 |

TABLE 22

Summary Table of Pharmacokinetics of Intravenous (IV)
Liraglutide Formulation in New Zealand White Rabbits

| Time | Conc | ln(C) | AUC | AUMC | R | R_adj |
|---|---|---|---|---|---|---|
| 0 | 2730.55 | 7.91225833 | 0 | 0 | −0.978987 | 0.9542571 |
| 0.25 | 2230.36 | 7.70991829 | 620.11375 | 69.69875 | −0.9780188 | 0.95168984 |
| 0.5 | 2196.2 | 7.69448387 | 1173.43375 | 276.66 | −0.9766572 | 0.94809166 |
| 1 | 2157.7 | 7.67679812 | 2261.90875 | 1090.61 | −0.9748587 | 0.9432566 |
| 2 | 2063.13 | 7.63197953 | 4372.32375 | 4232.59 | −0.9723249 | 0.93631843 |
| 6 | 1974.81 | 7.58822747 | 12448.2038 | 36182.83 | −0.9688755 | 0.92646361 |
| 12 | 1550.18 | 7.34612633 | 23023.1738 | 127535.89 | −0.961934 | 0.90664632 |
| 24 | 1177.53 | 7.0711743 | 39389.4338 | 408713.17 | −0.9551783 | 0.88315421 |
| 48 | 717.41 | 6.5756475 | 62128.7138 | 1161069.97 | −0.9512084 | 0.85719608 |
| 72 | 599.66 | 6.39636283 | 77933.5538 | 2092404.37 | −0.9502816 | 0.80607027 |
| 96 | 105.47 | 4.65842655 | 86395.1138 | 2732012.05 | | |
| 120 | 65.3 | 4.17899204 | 88444.3538 | 2947545.49 | | |

Figure 25:
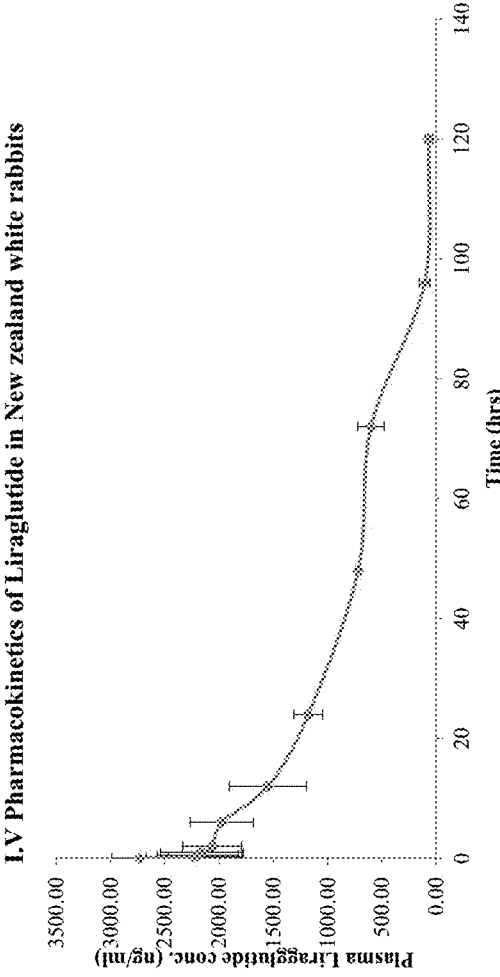
FIG. 25 is a graph showing plasma concentration of liraglutide following administration of an intravenous liraglutide formulation to New Zealand White Rabbits.

Concentration of liraglutide following administration of the intravenous formulation to New Zealand White Rabbits is graphed in FIG. 25.

TABLE 23

Pharmacokinetics of Intravenous (IV) Liraglutide
Formulation in New Zealand White Rabbits

| Parameter | Unit | Value |
|---|---|---|
| R | | 0.978018843 |
| R_adjusted | | 0.951689842 |
| NumRegPoints | | 11 |
| TimeRegStart | h | 0.25 |
| TimeRegEnd | h | 120 |
| Lambda_z | 1/h | 0.028442046 |
| t½ | h | 24.37051033 |
| Tmax | h | 0.25 |
| Cmax | ng/ml | 2230.36 |
| C0 | ng/ml | 2265.051329 |
| Tlast | h | 120 |
| Clast_obs | ng/ml | 65.3 |
| Clast_obs/Cmax | | 0.029277785 |
| AUC 0-t | ng/ml*h | 88386.16642 |
| AUC t-inf_obs | ng/ml*h | 2295.8967 |
| AUC 0-inf_obs | ng/ml*h | 90682.06312 |
| AUC 0-t/0-inf_obs | | 0.974681909 |
| AUC 0-inf/D_obs | ng/ml*h/(µg) | 906.8206312 |
| AUMC 0-t | ng/ml*h^2 | 2947545.49 |
| AUMC t-inf_obs | ng/ml*h^2 | 356229.5283 |
| AUMC 0-inf_obs | ng/ml*h^2 | 3303775.018 |
| AUMC 0-t/0-inf_obs | | 0.892175004 |
| MRT 0-t | h | 33.34849343 |
| MRT 0-inf_obs | h | 36.43250831 |
| Vz_obs | (µg)/(ng/ml) | 0.038771961 |
| Cl_obs | (µg)/(ng/ml)/h | 0.001102754 |
| Vss_obs | (µg)/(ng/ml) | 0.040176091 |
| Clast_pred | ng/ml | 77.42485926 |
| Clast_pred/Cmax | | 0.034714064 |
| AUC t-inf_pred | ng/ml*h | 2722.197226 |
| AUC 0-inf_pred | ng/ml*h | 91108.36364 |
| AUC 0-t/0-inf_pred | | 0.970121325 |
| AUC 0-inf/D_pred | ng/ml*h/(µg) | 911.0836364 |
| AUMC t-inf_pred | ng/ml*h^2 | 422373.9831 |
| AUMC 0-inf_pred | ng/ml*h^2 | 3369919.473 |
| AUMC 0-t/0-inf_pred | | 0.874663479 |
| MRT 0-inf_pred | h | 36.98803643 |
| Vz_pred | (µg)/(ng/ml) | 0.038590545 |
| Cl_pred | (µg)/(ng/ml)/h | 0.001097594 |
| Vss_pred | (µg)/(ng/ml) | 0.04059785 |

TABLE 24

Pharmacokinetics of Subcutaneous (S.C) Liraglutide
Formulation in New Zealand White Rabbits

| Time | Abs (450 nm) | B/Bo | logit B/Bo | Conc. ng/ml | Mean Conc. ng/ml |
|---|---|---|---|---|---|
| 0 | 0.888 | 0.567 | 0.268 | 223.34 | 213.38 |
| | 0.911 | 0.581 | 0.328 | 203.42 | |
| 0.25 | 0.628 | 0.401 | −0.401 | 627.02 | 651.86 |
| | 0.610 | 0.389 | −0.451 | 676.70 | |
| 0.5 | 0.432 | 0.276 | −0.966 | 1498.45 | 975.42 |
| | 0.709 | 0.453 | −0.190 | 452.39 | |
| 1 | 0.362 | 0.231 | −1.202 | 2158.95 | 2034.83 |
| | 0.385 | 0.245 | −1.123 | 1910.71 | |
| 2 | 0.316 | 0.201 | −1.377 | 2828.16 | 2625.63 |
| | 0.342 | 0.218 | −1.277 | 2423.10 | |
| 6 | 0.326 | 0.208 | −1.335 | 2650.95 | 2734.37 |
| | 0.316 | 0.202 | −1.375 | 2817.79 | |
| 12 | 0.456 | 0.291 | −0.891 | 1334.40 | 1351.23 |
| | 0.451 | 0.288 | −0.907 | 1368.06 | |
| 24 | 0.709 | 0.453 | −0.190 | 452.39 | 975.42 |
| | 0.432 | 0.276 | −0.966 | 1498.45 | |
| 48 | 0.585 | 0.373 | −0.519 | 752.12 | 914.69 |
| | 0.502 | 0.320 | −0.752 | 1077.26 | |
| 72 | 0.685 | 0.437 | −0.254 | 499.43 | 599.21 |
| | 0.602 | 0.384 | −0.472 | 698.98 | |
| 96 | 0.619 | 0.395 | −0.425 | 650.66 | 562.69 |
| | 0.697 | 0.445 | −0.221 | 474.72 | |
| 120 | 0.756 | 0.482 | −0.070 | 376.20 | 380.10 |
| | 0.751 | 0.479 | −0.083 | 384.00 | |

TABLE 25

Pharmacokinetics of Subcutaneous (S.C) Liraglutide
Formulation in New Zealand White Rabbits

| | Liraglutide (Conc. ng/ml) | |
|---|---|---|
| Time (Hrs) | Mean | ±SEM |
| 0 | 213.38 | 9.96 |
| 0.25 | 651.86 | 24.84 |
| 0.5 | 975.42 | 523.03 |
| 1 | 2034.83 | 124.12 |
| 2 | 2625.63 | 202.53 |
| 6 | 2734.37 | 83.42 |
| 12 | 1351.23 | 16.83 |
| 24 | 975.42 | 523.03 |
| 48 | 914.69 | 162.57 |
| 72 | 599.21 | 99.78 |
| 96 | 562.69 | 87.97 |
| 120 | 380.10 | 3.90 |

TABLE 26

Summary Table of Pharmacokinetics of Subcutaneous (S.C)
Liraglutide Formulation in New Zealand White Rabbits

| Time | Conc | ln(C) | AUC | AUMC | R | R_adj |
|---|---|---|---|---|---|---|
| 0 | 213.380334 | 5.36307618 | 0 | 0 | | |
| 0.25 | 651.864316 | 6.47983644 | 108.155581 | 20.3707599 | | |
| 0.5 | 975.42167 | 6.88286986 | 311.566329 | 101.705374 | | |
| 1 | 2034.83113 | 7.61816811 | 1064.12953 | 732.340864 | | |
| 2 | 2625.63085 | 7.87307647 | 3394.36052 | 4375.38728 | | |
| 6 | 2734.37132 | 7.91365682 | 14114.3649 | 47690.3666 | −0.9210214 | 0.81793651 |
| 12 | 1351.23036 | 7.20877084 | 26371.1699 | 145553.343 | −0.977909 | 0.94538256 |
| 24 | 975.42167 | 6.88286986 | 40331.0821 | 383302.65 | −0.9705114 | 0.92252323 |
| 48 | 914.689407 | 6.81858456 | 63012.4151 | 1191085.19 | −0.9685535 | 0.90714372 |
| 72 | 599.208721 | 6.39560999 | 81179.1926 | 2235662.62 | −0.9226965 | 0.70273772 |
| 96 | 562.687963 | 6.33272523 | 95121.9528 | 3401595.49 | | |
| 120 | 380.095842 | 5.94042344 | 106435.358 | 4597150.04 | | |

Figure 26:
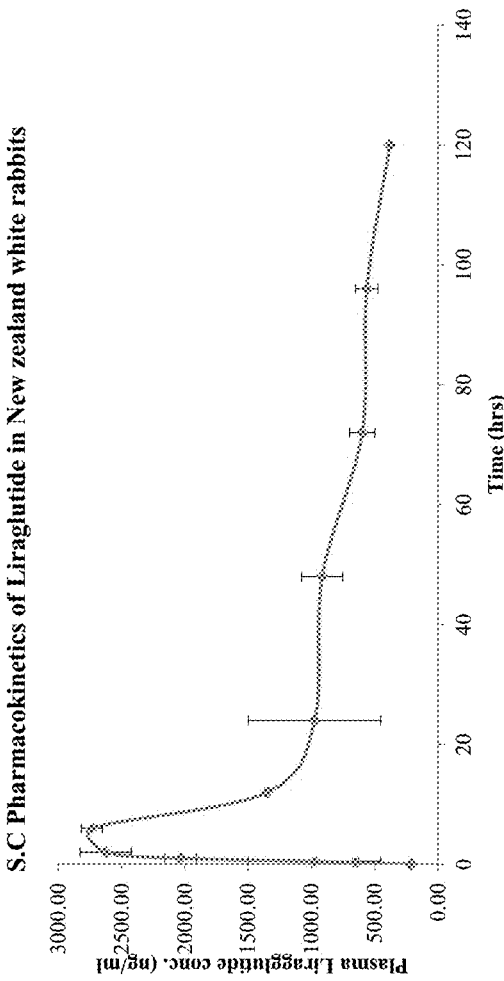
FIG. 26 is a graph showing plasma concentration of liraglutide following administration of a subcutaneous liraglutide formulation to New Zealand White Rabbits.

Concentration of liraglutide following administration of the subcutaneous formulation to New Zealand White Rabbits is graphed in FIG. 26.

TABLE 27

Pharmacokinetics of Subcutaneous (S.C) Liraglutide
Formulation in New Zealand White Rabbits

| Parameter | Unit | Value |
|---|---|---|
| R | | −0.977909017 |
| R_adjusted | | 0.945382557 |
| NumRegPoints | | 6 |
| TimeRegStart | h | 12 |
| TimeRegEnd | h | 120 |
| Lambda_z | 1/h | 0.010688866 |
| $t^{1/2}$ | h | 64.84759024 |
| Tmax | h | 6 |
| Cmax | ng/ml | 2734.371323 |
| Tlag | h | 0 |
| Tlast | h | 120 |
| Clast_obs | ng/ml | 380.0958421 |
| Clast_obs/Cmax | | 0.139006666 |
| AUC 0-t | ng/ml*h | 106435.3585 |
| AUC t-inf_obs | ng/ml*h | 35559.97934 |
| AUC 0-inf_obs | ng/ml*h | 141995.3378 |
| AUC 0-t/0-inf_obs | | 0.749569388 |
| AUC 0-inf/D_obs | ng/ml*h/(μg) | 946.6355854 |
| AUMC 0-t | ng/ml*h^2 | 4597150.037 |
| AUMC t-inf_obs | ng/ml*h^2 | 7594021.944 |
| AUMC 0-inf_obs | ng/ml*h^2 | 12191171.98 |
| AUMC 0-t/0-inf_obs | | 0.377088441 |
| MRT 0-t | h | 43.19194395 |
| MRT 0-inf_obs | h | 85.85614267 |
| Vz/F_obs | (μg)/(ng/ml) | 0.098829263 |
| Cl/F_obs | (μg)/(ng/ml)/h | 0.001056373 |
| Clast_pred | ng/ml | 394.0757348 |
| Clast_pred/Cmax | | 0.14411932 |
| AUC t-inf_pred | ng/ml*h | 36867.87235 |
| AUC 0-inf_pred | ng/ml*h | 143303.2308 |
| AUC 0-t/0-inf_pred | | 0.742728254 |
| AUC 0-inf/D_pred | ng/ml*h/(μg) | 955.3548721 |
| AUMC t-inf_pred | ng/ml*h^2 | 7873329.425 |
| AUMC 0-inf_pred | ng/ml*h^2 | 12470479.46 |
| AUMC 0-t/0-inf_pred | | 0.368642605 |
| MRT 0-inf_pred | h | 87.02162115 |
| Vz/F_pred | (μg)/(ng/ml) | 0.097927272 |
| Cl/F_pred | (μg)/(ng/ml)/h | 0.001046731 |

Other Embodiments

While we have described a number of embodiments, it is apparent that our basic disclosure and examples may provide other embodiments that utilize or are encompassed by the compositions and methods described herein. Therefore, it will be appreciated that the scope of is to be defined by that which may be understood from the disclosure and the appended claims rather than by the specific embodiments that have been represented by way of example.

All references cited herein are hereby incorporated by reference.

What is claimed is:

1. A liquid polypeptide formulation for oral delivery comprising a polypeptide component that consists of the polypeptide in a solid form, wherein the solid form is a crystallized form or an amorphous form; wherein:
  (a) the polypeptide component:
    (i) is chosen from a GLP-1 receptor agonist, trastuzumab, or insulin, and wherein the GLP-1 receptor agonist is at least 94% homologous to human GLP-1, and (ii) is suspended in a pharmaceutically acceptable liquid carrier consisting of vitamin E, optionally combined with wheat germ oil; and
  (b) the polypeptide formulation:
    (i) consists of about 0.05 mg/kg to about 220 mg/kg of the polypeptide component, and
    (ii) has a pH within a range of about 4.5 to 7.5; and
  wherein the weight percent ratio of polypeptide:vitamin E and optionally wheat germ oil is within a range of about 6:1 to 1:300.

2. The polypeptide formulation of claim 1, wherein the polypeptide formulation is disposed within a pharmaceutically acceptable capsule, so that the solid polypeptide component suspended in the liquid carrier forms a core inside the capsule.

3. The polypeptide formulation of claim 1, wherein the polypeptide formulation comprises about 1 μg to about 2,000 mg of the polypeptide.

4. The polypeptide formulation of claim 1, wherein the polypeptide formulation comprises about 1 mg to about 2,000 mg of the vitamin E.

5. The polypeptide formulation of claim 1, wherein the polypeptide formulation comprises a molar excess or excess by weight of the vitamin E relative to the amount of polypeptide in the polypeptide formulation.

6. The polypeptide formulation claim 1, wherein the crystallized polypeptide composition comprises crystals of polypeptide having an average particle size of less than 25 microns.

7. The polypeptide formulation of claim 1, wherein the amorphous polypeptide composition comprises particles of polypeptide having an average particle size of less than 25 microns.

8. The polypeptide formulation of claim 1, wherein the polypeptide composition comprises a lyophilized polypeptide.

9. The polypeptide formulation of claim 1, wherein the polypeptide composition comprises microcrystals of polypeptide.

10. The polypeptide formulation of claim 1, wherein the polypeptide composition comprises a powder comprising crystallized polypeptide.

11. The polypeptide formulation of claim 2, wherein the capsule is a hard-shell capsule or soft-shell capsule.

12. The polypeptide formulation of claim 2, wherein the capsule is formulated for delivery to the gut.

13. The polypeptide formulation of claim 2, wherein the capsule comprises an enteric coating.

14. The polypeptide formulation of claim 1, wherein the polypeptide formulation comprises about 1 μg to about 10 mg of the polypeptide.

15. The polypeptide formulation of claim 1, wherein the polypeptide is insulin.

16. The polypeptide formulation of claim 1, wherein the polypeptide is trastuzumab or an analog or derivative thereof.

17. The polypeptide formulation of claim 1, wherein the polypeptide is liraglutide or an analog or derivative thereof.

18. The polypeptide formulation of claim 1, wherein the polypeptide is a therapeutic polypeptide.

\* \* \* \* \*